United States Patent [19]
Skates et al.

[11] Patent Number: 6,030,341
[45] Date of Patent: Feb. 29, 2000

[54] ROC METHOD FOR EARLY DETECTION OF DISEASE

[75] Inventors: Steven J. Skates, Cambridge, Mass.; Ian Jacobs, Bromley, United Kingdom; Robert Knapp, Chestnut Hill, Mass.

[73] Assignee: The General Hospital Corporation, Boston, Mass.

[21] Appl. No.: 09/139,088

[22] Filed: Aug. 24, 1998

Related U.S. Application Data

[62] Division of application No. 08/552,823, Nov. 3, 1995, Pat. No. 5,800,347.
[60] Provisional application No. 60/003,601, Sep. 12, 1995.
[51] Int. Cl.[7] .................................................. A61B 5/00
[52] U.S. Cl. ............................................ 600/300; 128/923
[58] Field of Search .......................... 600/300; 705/2–3; 395/22; 128/920–924

[56] References Cited

U.S. PATENT DOCUMENTS

| | | | |
|---|---|---|---|
| 4,852,570 | 8/1989 | Levine | 128/630 |
| 5,356,817 | 10/1994 | Cole | 436/64 |
| 5,396,886 | 3/1995 | Caypers | 600/300 |
| 5,733,721 | 3/1998 | Hemstreet, III et al. | 435/6 |
| 5,790,761 | 8/1998 | Heseltine et al. | 395/22 |

FOREIGN PATENT DOCUMENTS

| | | |
|---|---|---|
| 0288082 | 10/1988 | European Pat. Off. . |
| 0590200 | 4/1994 | European Pat. Off. . |
| WO88/03954 | 6/1988 | WIPO . |
| WO92/01936 | 2/1992 | WIPO . |
| WO92/12430 | 7/1992 | WIPO . |
| WO93/02358 | 2/1993 | WIPO . |

OTHER PUBLICATIONS

Cronin, K.A. et al., "Using the Gibbs Sampler to Detect Changepoints: Application to PSA as a Longitudinal Marker for Prostate Cancer", *Computing Sci. and Statistics,26th Symp. on the Interferace*, Research Triangle Park, NC (Jun. 1994).

Jacobs, I. and Oram, D. (Study Directors), "Randomised Trial of Screening for Ovarian Cancer", *Ovarian Cancer Screening Unit, The Royal Hospitals Trust, St. Bartholomew's Hospital*, London EC1A 7BE.

Wilding, P. et al., "Application of bBckpropagation Neural Networks to Diagnosis of Breast and Ovarian Cancer", *Cancer Letters*, pp: 145–153 (1994).

*Primary Examiner*—Francis J. Jaworski
*Attorney, Agent, or Firm*—Hamilton, Brook, Smith and Reynolds, P.C.

[57] ABSTRACT

A method of assessing risk of an individual for a disease is disclosed. A level of a marker for the disease is detected, and the risk of disease is computed from a statistical analysis of the marker level distributions for tested normal and diseased populations, using multivariate distributions. The computed risk is compared to thresholds to triage the individual into a normal, borderline, or elevated risk group, and a course of action based on the risk group is determined. Memory storing a program for execution on a data processing system, as well as a computer system comprising said memory is also disclosed, the memory comprising a receiver for signals representative of levels of a marker for the disease; a central processing unit for computing risk of disease from one or more levels of the marker, and for comparing the computed risk to thresholds to triage the individual; and storage medium for the marker levels for subsequent computations of risk of disease.

19 Claims, 9 Drawing Sheets

ROC METHOD FOR EARLY DETECTION OF DISEASE

RELATED APPLICATION

This application is a Divisional of U.S. Ser. No.: 08/552,823, filed Nov. 3, 1995 and was U.S. Pat. No. 5,800,347 which claims priority to provisional application No. 60/003,601, filed Sep. 12, 1995, the entire teachings of which are incorporated herein by reference.

GOVERNMENT FUNDING

This invention was made with Government support under contract number CA 56793 awarded by the National Institutes of Health. The United States Government has certain rights to this invention.

BACKGROUND OF THE INVENTION

Ovarian cancer is the leading cause of death from gynecologic malignancy among women in the United States, and at most ages is responsible for more deaths than all other gynecologic cancers combined (Cramer, D., "Epidemiology of Gynecologic Cancer", p. 80, in *Gynecologic Oncology*, 2d ed., (R. C. Knapp and R. S. Berkowitz, eds.), McGraw Hill, New York, 1993)). Annual U.S. incidence and mortality are 26,600 and 14,800, respectively (Silverberg, CA: *A cancer journal for physicians* 44:4–8 (1994)). The age specific incidence rises sharply after 50 years of age (Cramer, D., p. 80 of *Gynecologic Oncology*, 2d ed., (R. C. Knapp and R. S. Berkowitz, eds.), McGraw Hill, New York, 1993)). More than 70% of cases present in late state (Piver, M. S. et al., "Ovarian Cancer", p. 253, in *Gynecologic Oncology*, 2d ed., (R. C. Knapp and R. S. Berkowitz, eds.), McGraw Hill, New York, 1993)) and consequently have poor prognosis. In such cases most women die of the disease. Therapeutic advances have had negligible impact on the overall survival rate during the past thirty years. However, if cancer is detected in early stage before dissemination of the disease, the five year survival rate is over 90% (Yound, R. C. et al., *N. Engl. J. Med.* 322:1070–1073 (1990)). Furthermore, recent genetic research on ovarian cancer provides evidence of a unifocal origin (Mok, C. H. et al., *Cancer Research* 52:5119–5122 (1992)). These observations make early detection of ovarian cancer through a mass screening program of postmenopausal woman an attractive method for reducing mortality due to ovarian cancer.

Invasive surgery is the only definitive method of diagnosis for ovarian cancer. Nevertheless, most epithelial ovarian malignancies shed an antigenic determinant into the blood that is detectable using the CA125 radioimmunoassay (RIA) (Bast, R. C. Jr. et al., *N. Engl. J. Med* 309:883–887 (1983); Klug, T. L. et al., *Cancer Res.* 44:883–887 (1984)). In normal populations, CA125 levels are rarely elevated (Jacobs, I. et at., submitted 1992; Zurawski, V. R. Jr., *Obstet Gynecol.* 69:606–611 (1987)); however CA 125 levels have been elevated prior to clinical detection of ovarian cancer (Bast, R. C. Jr. et al., *Gynecol. Oncol.* 22:115–120 (1984); Zurawski, V. R. Jr., *Int. J. Cancer* 42: 677–680 (1988)). CA125 levels correlate with tumor volume (Zurawski, V. R. et al., *Gynecol. Oncol.* 30:7–14 (1988)). Progressively higher levels of CA125 are associated with more advanced disease, and subsequent lower levels with absence of the disease post-operatively. A level of 35 U/ml CA125 has been used to evaluate patients with demonstrable cancer (Bast, R. C. Jr. et al., *Engl. J. Med.* 309:169–171 (1983)). Levels of 30 U/ml to 35 U/ml have been used in retrospective and prospective studies of the incidence of ovarian cancer (Zurawski, V. R. Jr. et al. *Gynecol. Oncol* 36:299–305 (1990); Einhorn, N. et al., *Obstet. Gynecol.* 80:14–18 (1992)). Due to the low rate of occurrence of ovarian cancer, the positive predictive value of these CA125 reference levels for the presence of ovarian cancer are less than 2%. However, a high positive predictive value is necessary for an early detection program of ovarian cancer, because of the invasive nature of the surgery necessary for biopsy or removal of an ovary. Literature has suggested a minimum required positive predictive value of 10% (Jacobs, I. and Best, R., *Human Reproduction,* 4:1–12 (1989)). Thus, early detection of ovarian cancer with the CA125 assay has been criticized as ineffective. A need remains for an effective method for evaluating individuals at risk for ovarian cancer, in order to detect the disease in its early stages and reduce the rate of mortality due to ovarian cancer.

SUMMARY OF THE INVENTION

In accordance with the present invention a method of assessing the risk of an individual for a disease includes detecting a level of one or more markers for the disease in a sample from the individual, and computing risk of disease from detected levels of the markers. The risk of disease is computed based on a statistical analysis of multivariate marker level distributions for tested normal and diseased populations. The marker is a marker for which the level changes exponentially over time, so that the multivariate distributions can be determined from the slope and intercept of the log of detected marker levels. Random draws using Gibbs' sampling can be used to compute average densities in the multivariate distributions. Risk of disease is the product of an odds factor (computed as the ratio of the density from the disease population distribution to the density from the normal population distribution) and an estimate of prior odds of disease. A time correlation component can be added to a linear regression model of marker levels in calculation of the risk of disease.

The method is iterative in that the risk is recomputed with each serial test of a marker level. A course of action is determined for the individual, based on the computed or recomputed risk. The computed or recomputed risk is compared to thresholds to triage the individual into a normal, borderline, or elevated risk group, and a course of action based on the risk group is determined. Individuals triaged into the "normal" risk group are subjected to retesting at a routine screening interval. Individuals triaged into the "borderline" risk group are subjected to more frequent marker level measurements, at a retest interval that is less than that for those in the normal risk group; the interval between marker level measurements is inversely related to the computed risk. Individuals triaged into the "elevated" risk group are subjected to a secondary test, using a second line early detection modality which is usually more expensive that the first line modality test. Those triaged into the "elevated" risk group can also be subjected to retesting of the marker level. If results of a secondary test are normal, the future course of action is based on the recomputed risk; if the results of the secondary test are abnormal, the future course of action is surgery; and if the results of the secondary test are equivocal, the secondary test is repeated and a course of action is determined based on the results of the repeated secondary test or on the recomputed risk.

In a preferred embodiment, the individual is a postmenopausal woman, the disease is ovarian cancer, the marker is CA125, and the secondary test is an ultrasonographic test. In this embodiment, the "normal" risk group includes those with a calculated risk of ovarian cancer (ROC) less than or equal to 0.05%; the "borderline" risk group includes those with a calculated ROC greater than 0.05% but less than 4.0%; and the "elevated" risk group includes those with a calculated ROC greater than or equal to 4.0%.

In accordance with one embodiment of the current invention, memory storing a program for execution on a data processing system is provided, the memory comprising a receiver for signals representative of marker levels for a disease, a central processing unit (CPU) for computing the risk of disease based on one or more levels of the marker or markers and for comparing the computed risk to thresholds to triage the individual into risk groups, and a storage medium for the marker levels, to facilitate iterative computation of the risk. The memory can create a bar graph display indicating the computed risk, showing green when the risk is less than the normal threshold, yellow if the risk is between the borderline thresholds, and red when the risk is greater than the elevated threshold. In accordance with another embodiment, a computer system is provided which comprises an input device for receiving marker levels, a display for displaying risk of disease and courses of action, and memory as described above.

In the current invention, a marker level corresponding to the lowest borderline risk can be set much lower than a standard reference level, since the course of action for an individual with borderline risk is a cost-effective retest of a marker level, rather than a more expensive second line modality. The methods of the current invention have an increased the positive predictive value, compared to previous methods. For ovarian cancer, the positive predictive value of the current method is approximately 16%, which is an eightfold increase over previous methods. The increased positive predictive value of the methods of the invention render feasible the widescale screening of individuals for disease, thereby increasing the early detection of disease and reducing mortality due to the disease.

Figure 1:
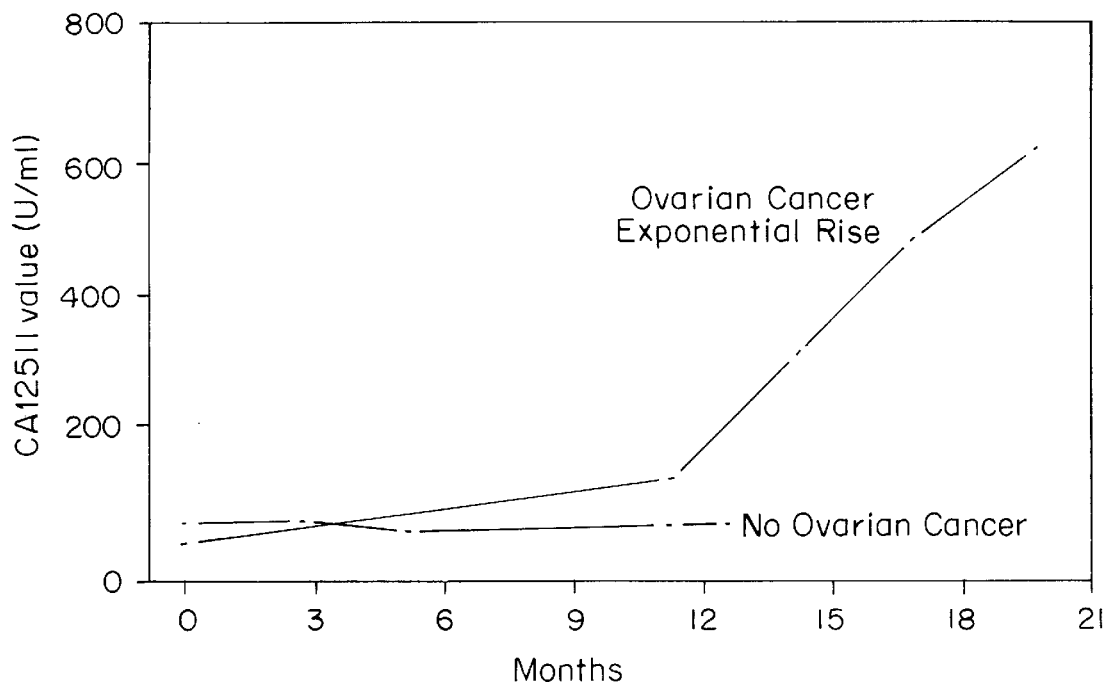
FIG. 1 is a graphic depiction of representative CA125 marker levels for an individual in the "normal" population (no ovarian cancer) and an individual in the "diseased" population (ovarian cancer).

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The risk of ovarian cancer (ROC) is assessed for a woman in the target population, using statistical analysis of detected levels of one or more markers for the woman. The target population is post-menopausal women over approximately 50 years of age, because of the increasing incidence of ovarian cancer between the ages of 50 and 75 years, and the physical changes associated with menopause. The term, "marker," as used herein, refers to a qualifiable physical characteristic which correlates with a disease state. The marker is a biochemical marker, such as a peptide, glycoprotein, carbohydrate, saccharide, or antibody. For ovarian cancer, one appropriate marker is CA125. A second appropriate marker is OVX1. The level (concentration or amount) of the marker(s) in a sample is detected (measured), using standard techniques known in the art. The sample is a physical specimen in which the marker can be detected, such as tissue, blood or serum. In a preferred embodiment, the level of CA125 in a serum sample is measured using the CA125II RIA test (Centocor, Malvern, Pa.). The level of the marker(s) is detected either once, or a plurality of times (i.e., the woman undergoes a retest for the level of the marker, usually at a subsequent date). If the marker level is detected a plurality of times, the length of time between each retest is recorded. The length of time between each retest varies from approximately 1 month to approximately 12 months.

The "risk of cancer" (ROC), or the risk of disease if the target disease is other than cancer, for the individual is computed using statistical analysis of the detected level (or levels) of the marker (or markers), relative to marker level distributions for tested normal and diseased populations. The ROC is defined as the probability that the woman has ovarian cancer, given the marker measurements, and summarizes all the marker levels (levels of a single or of multiple markers, measured once of a multitude of times) in one interpretable number. The interpretation is that, for example, among a group of women each with an ROC of 20%, it is expected that 1 woman in 5 will have ovarian cancer.

In one embodiment, the ovarian cancer marker CA125 is used. Pre-clinical (pre-symptomatic) marker level distributions for the ovarian cancer marker CA125 were obtained from normal and diseased populations. Data used to determine the pre-clinical marker level distributions included data from the Stockholm screening trial for ovarian cancer (Einhorn, N. et al., *Obstet. Gynecol.* 80:14–18 (1992)), and data from a screening trial with CA125 performed in Britain (Jacobs, I, et al., *British Medical Journal* (1993)). In a "normal" populations of postmenopausal women, the CA125 marker levels are approximately 5 to 40 U/ml, and remain relatively constant over time, as shown in FIG. 1. In contrast, in a "diseased" population (women having ovarian cancer), the marker levels are approximately 5 to 1000 U/ml, and increase over time (FIG. 1). In most cases of ovarian cancer where serum levels of the marker have been measured serially before clinical detection of disease, the rise in marker levels over time has been exponential.

Figure 2:
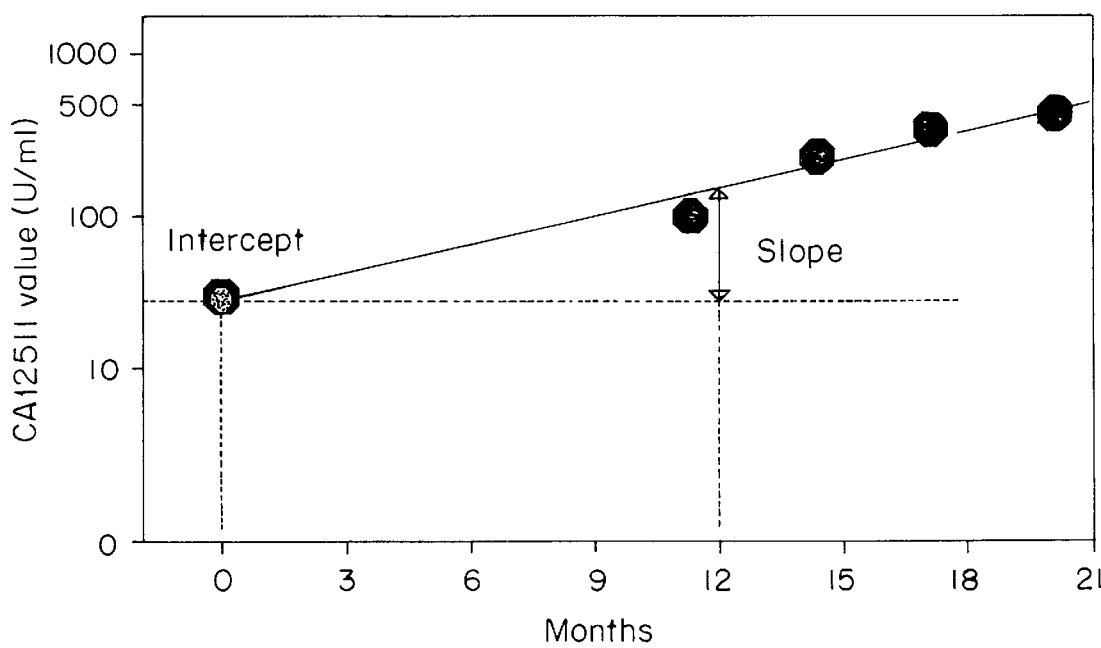
FIG. 2 is a graphic representation of a linear regression of the log(CA125) level over time for an individual in the "diseased" population (ovarian cancer).
Figure 3A:
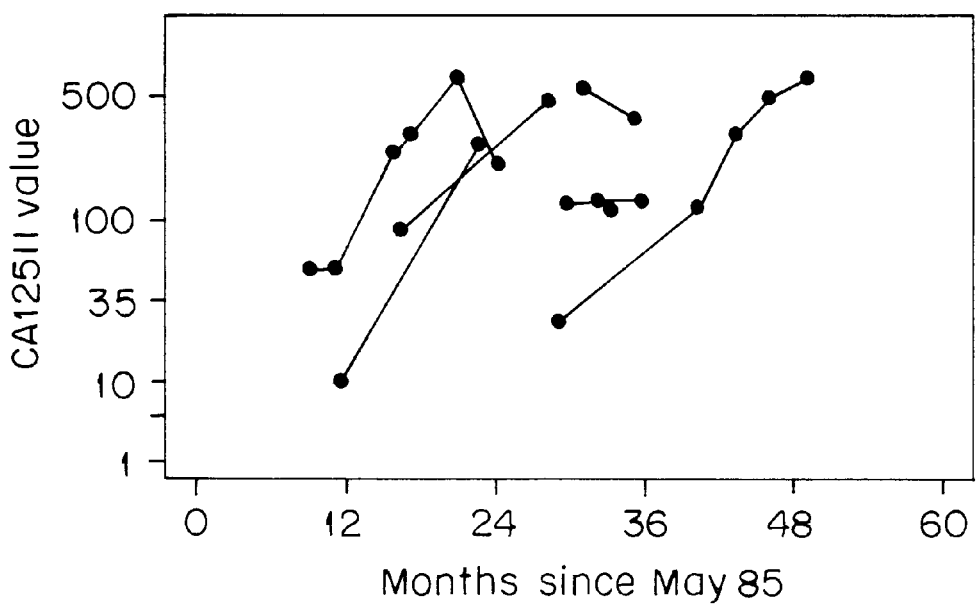
FIGS. 3A, 3B, 3C and 3D are a series of graphs, individually labelled as 3A, 3B, 3C and 3D, depicting CA125 levels in women with ovarian cancer (3A), other gynecological cancer (3B), breast cancer (3C), and other cancer (3D). CA125 levels were plotted on a logarithmic scale, and the time axis was specified in months.
Figure 3B:
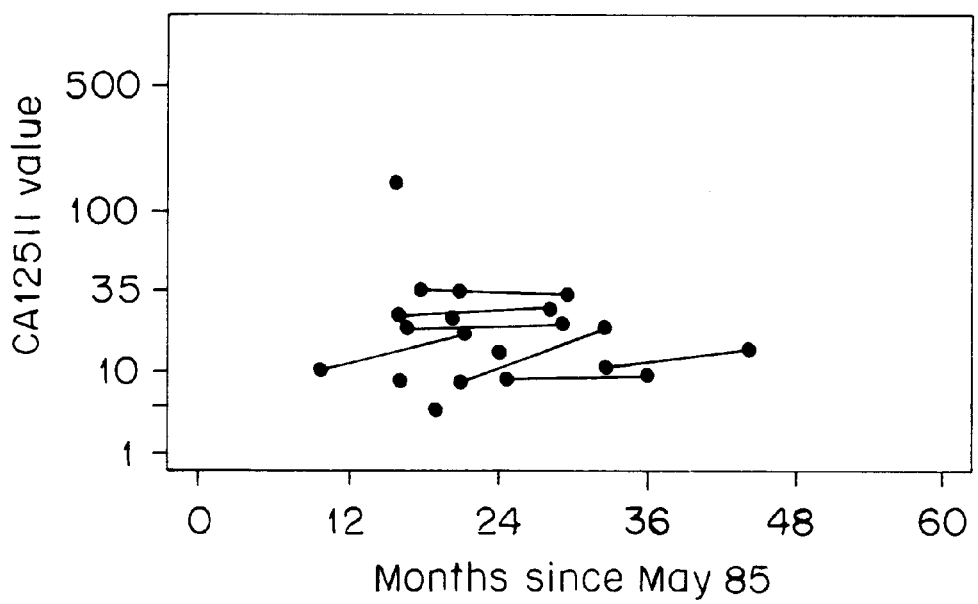
Figure 3C:
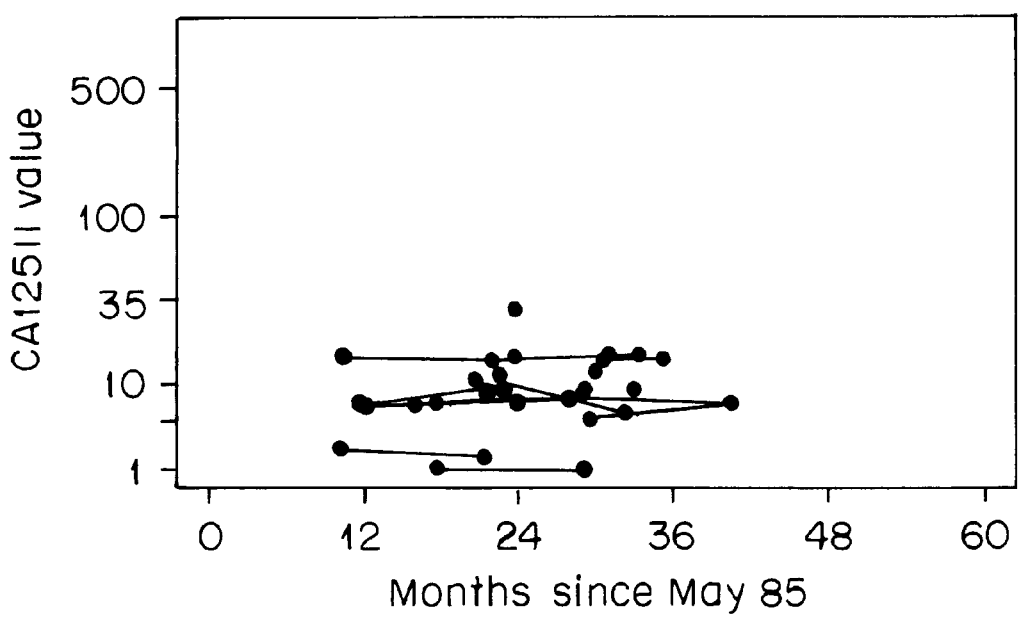
Figure 3D:
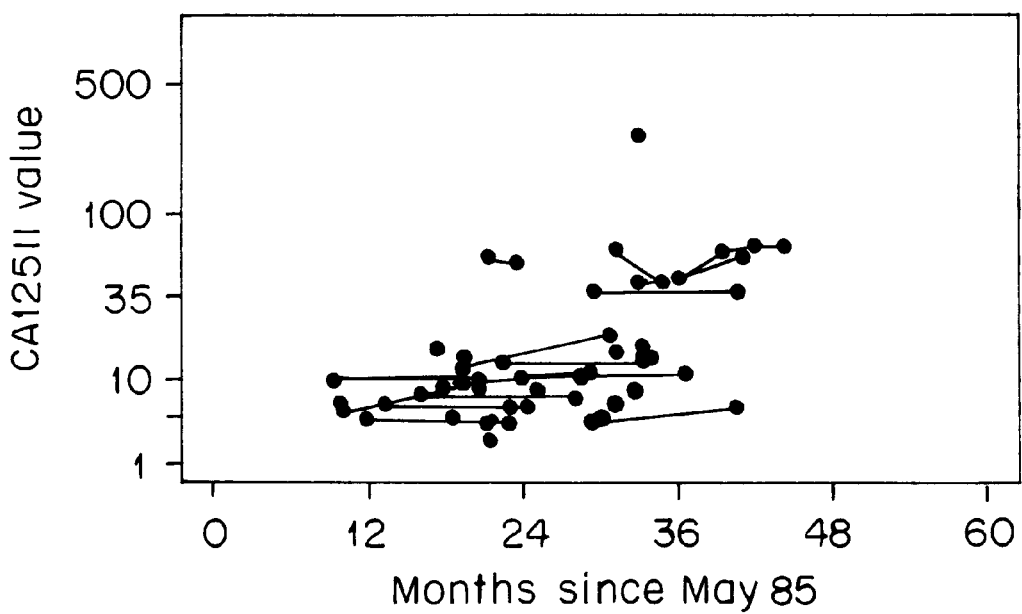
Figure 4A:
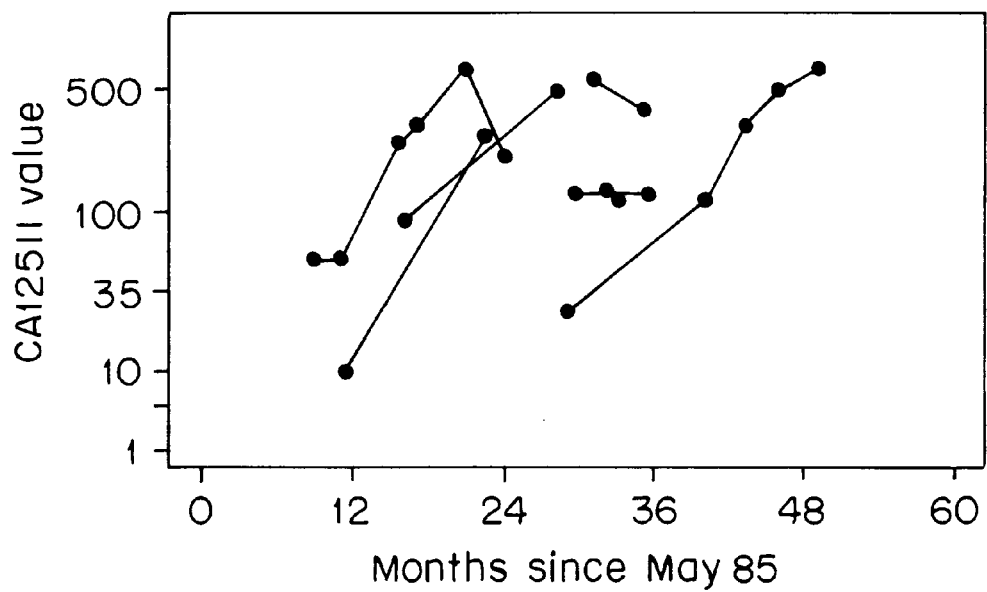
FIGS. 4A, 4B, 4C and 4D are a series of graphs, individually labelled a 4A, 4B, 4C and 4D, depicting CA125 levels in women with ovarian cancer (4A), benign gynecologic disease (4B), non-gynecologic disease (4C), or no disease (4D). CA125 levels were plotted on a logarithmic scale, and the time axis was specified in months.
Figure 4B:
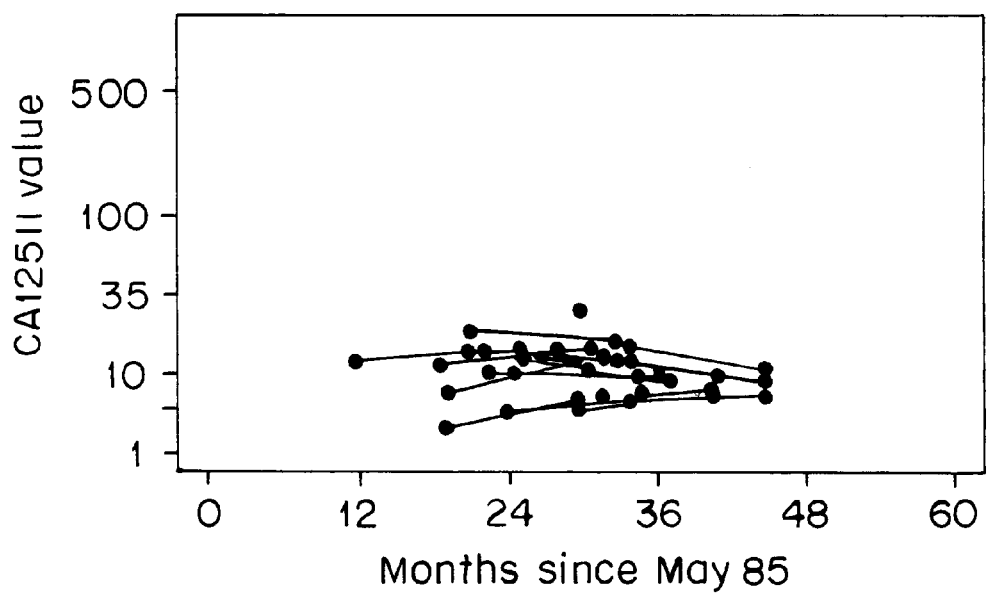
Figure 4C:
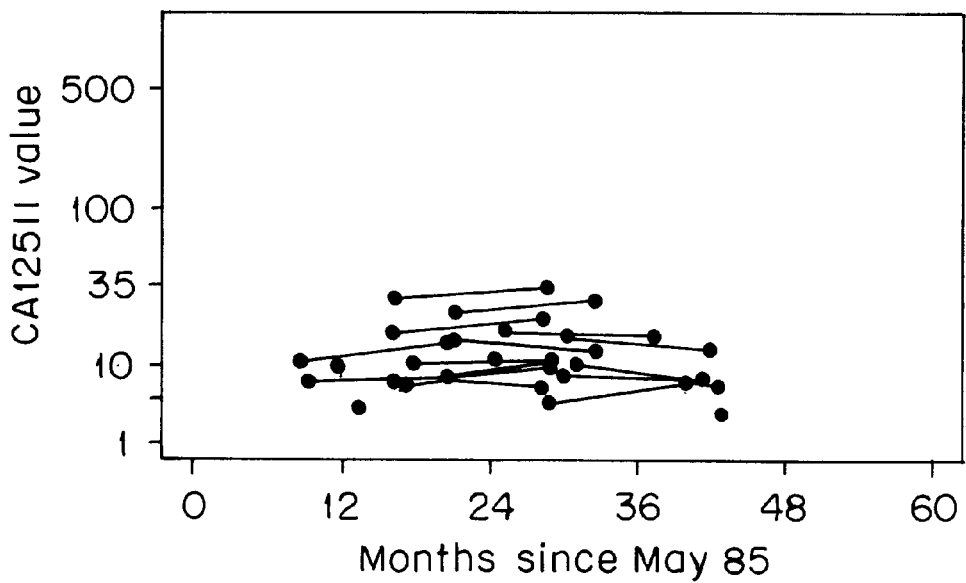
Figure 4D:
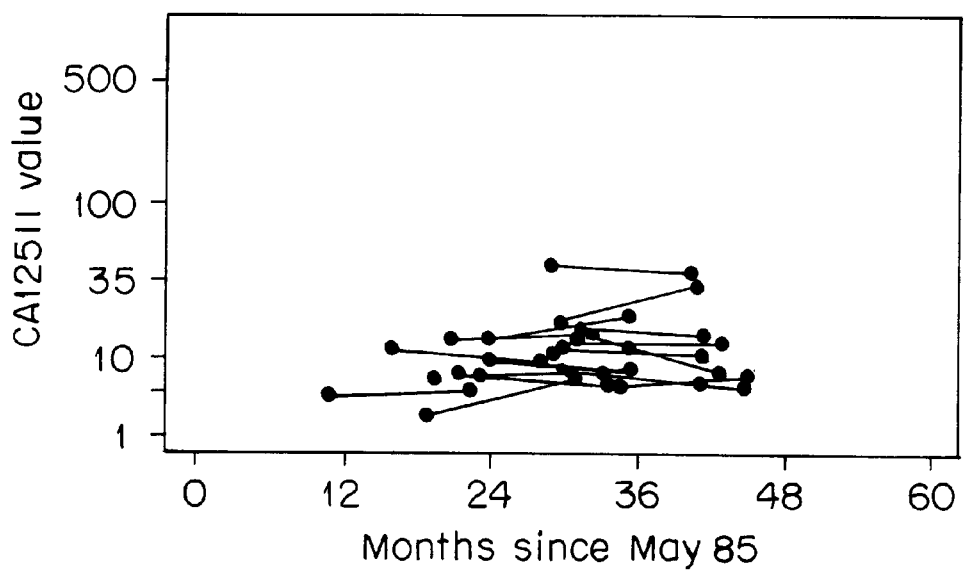

Because an exponential rise of CA125 over times corresponds to a linear increase of log(CA125) over time, a linear regression is fitted to each woman's log (CA125), and the slope and intercept are calculated. A representative linear regression of the log(CA125) over time is shown in FIG. 2. The intercept is the best estimate of the log(CA125) level at the time of the first serum sample, and the slope is the change from the intercept of log(CA125) within one year. Log(CA125) levels plotted against time for seven subgroups of women in the Stockholm study (ovarian cancer, other gynecological cancer, breast cancer, other cancer, benign gynecologic disease, non-gynecologic disease, and no apparent disease) verify the differential longitudinal behavior of CA125. As shown in FIGS. 3 and 4, the CA125 levels for individuals with ovarian cancer either increase sharply over time (slope) or have very high initial levels (intercept) or moderate values of both. In contrast, for those with other malignancies (FIG. 3), or benign disease or no disease (FIG. 4), most women have very low levels, or if the initial level is elevated either the level falls or remains constant over time. Very few women without ovarian cancer have rising levels over time, which enables the screening strategy based on this observation to have a very high positive predictive value.

Figure 5:
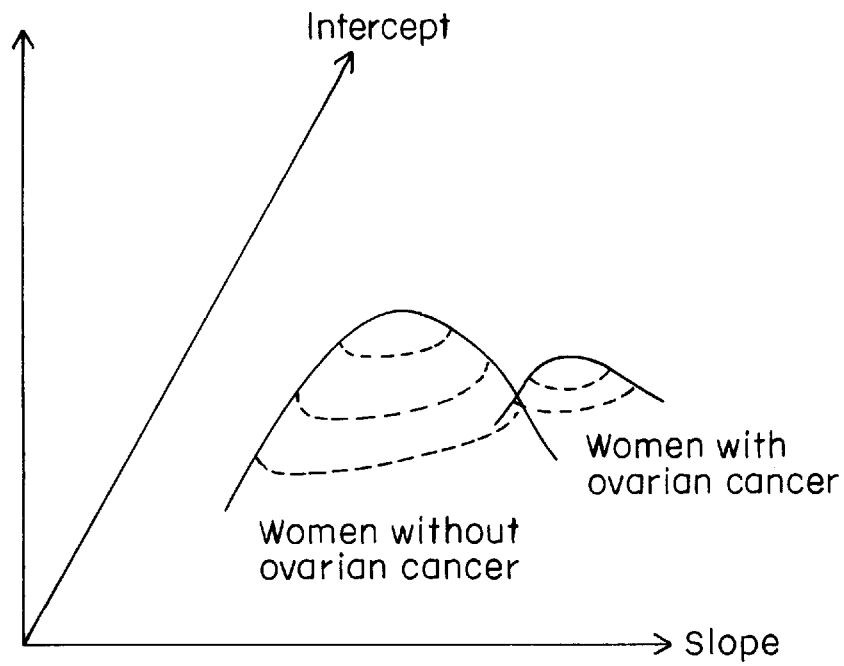
FIG. 5 is a graphic representation of a multivariate distribution of data points for slope and intercept calculated for individuals in normal (women without ovarian cancer) and diseased (women with ovarian cancer) populations.

After calculation of the slope and intercept of the log of detected marker levels over time for the individuals within the normal and diseased populations, the slopes and intercepts are plotted as points on a bivariate graph, as shown in FIG. 5. A bivariate distribution is fitted to these points, and the height of the distribution at any given location is the density of individuals in the population having that particular slope and intercept.

The distribution of slopes and intercepts is used to calculate the probability of ovarian cancer. The probability of ovarian cancer algorithm was developed by application of Bayes' Theorem (Press, S. J., *Bayesian Statistics*, Wiley, New York, 1993), assuming: (i) a bivariate Normal distribution for the slope and intercept in women without ovarian cancer (the "normal" population), (ii) a separate bivariate Normal distribution for the slope and intercept in woman with ovarian cancer (the "diseased" population), and (iii) a prior probability of ovarian cancer based on the known incidence at a given age.

To determine the probability of ovarian cancer for a woman of unknown status, the marker level for the woman is detected, and the slope and intercept for her detected marker level is computed and plotted as the test value. The "odds factor" for woman of unknown status determines how likely the test value (i.e., the estimated slope and intercept of a woman of unknown status) belongs to the group represented in the multivariate scatter plot of slope versus intercept by the cluster of points from the normal population, or from the diseased population. The "odds factor" is thus calculated as the ratio of height of distribution from the normal population, divided by the height of the distribution from the diseased population, for the test value.

The odds factor for an individual i at time t is:

$$[C_{ti}|V=v, X_i, \beta_{vi}] \sim N(X_i\beta_{vi}, \sigma^2) \quad (1)$$

$$[\beta_{iv}|\beta_{v0}, E_{98}] \sim N(\beta_{v0}, E_v) \quad (2)$$

Where V: indicator for ovarian cancer (V=0: no cancer V=1: has cancer); $C_{ti}$:CA125 levels (log); and $X_i$:time (months).

Because the distribution representing the disease population is much smaller than the distribution representing the normal population, an adjustment to the odds factor is made by calculating the "posterior odds". The odds of ovarian cancer, also known as the "posterior odds" (posterior to measurement of the marker level) is calculated as the product of the odds factor and the prior odds. The "prior odds" for the woman of unknown status is determined based on well known epidemiological data of the risk of ovarian cancer for a particular age. Family history of ovarian cancer, as well as other extrinsic risk factors, can also be factored into the prior odds.

The posterior odds are then readily converted to the risk of ovarian cancer, using the formula relating probability (measured in percent) and odds:

$$ROC=100*posterior\ odds/(posterior\ odds+1) \quad (3)$$

Thus, calculation of the ROC can be summarized by the following formula:

$$ROC=100*P[V=1|C_t, A] \quad (4)$$

where V: indicator for ovarian cancer (v=0: no cancer, v=1: has cancer); C:CA125 levels (vector-log of levels); t: times of sample (vector); and A: current age.

The calculation of the risk of cancer described above uses a multivariate distribution based on two factors: slope and intercept, calculated from levels of the marker and time. Additional factors can be brought into the calculation. For example, higher order multivariate distributions can be generated by detection of plural markers (for example, CA125 and OVX1 for ovarian cancer would result in a four-variate distribution).

To account for further sources of uncertainty, other elements can be factored into the calculation of the ROC. For example, the uncertainty in the means and standard deviations for the distributions representing the normal and diseased populations can be factored into the calculation of the odds factor. Accounting for this uncertainty will more accurately triage the individuals tested. To account for the uncertainty in the parameters of the distributions, random draws from the posterior distribution of the parameters can be obtained by Gibbs' sampling, a technique well known in the art (Gelfand, A. E., and A. F. M. Smith, *J. Am. Statistical Assoc.* 85(410):398(1990)). Random draws used are listed in Table 2 below. Each row describes a distribution for the normal and the disease populations. Each row consists of five values: an intercept from the normal population (first column); an slope from the normal population (second column); and intercept form the disease population (third column); an slope form the disease population (fourth column); and the variance about the regression line ($\sigma^2$) (fifth column). Given the serum levels of the marker(s) and the time intervals between measurements for an individual whose risk is being evaluated, the density specified by a row is calculated for both the diseased and normal populations.

The densities over the rows are averaged, and the ratio of the average density for the normal population to the average density for the diseased population gives the final odds factor.

Using these random draws, the odds factor for an individual, given new data $C_{it}^*$ are thus calculated as follows:

Each draw of $\sigma^2$, $(\beta_{0\upsilon}, E_\upsilon \upsilon=0,1)$: One draw $$\beta_{i\upsilon}^* \sim N(B_{0\upsilon}, E\upsilon), \upsilon=0,1 \quad (5)$$

$$\text{Sum likelihood } L_\upsilon \text{ of } C_{it}^* \sim N(X_i^* \beta_\upsilon^*, \sigma^2) \quad (6)$$

$$\text{Odds Factor} = L_0/L_1 \quad (7)$$

Alternatively or in addition, a linear regression model can be expanded to include time correlation between residuals of the serum levels with a person (Jones, R. H., *Longitudinal Data with Serial Correlation* (Chapman and Hall, 1993)), or a skewed bivariated distribution could be used to account for a skewed distribution of the slope and intercept. This generalizes the bivariate normal distribution and allows for skewness in the distributions of the slope and intercept.

Figure 6:
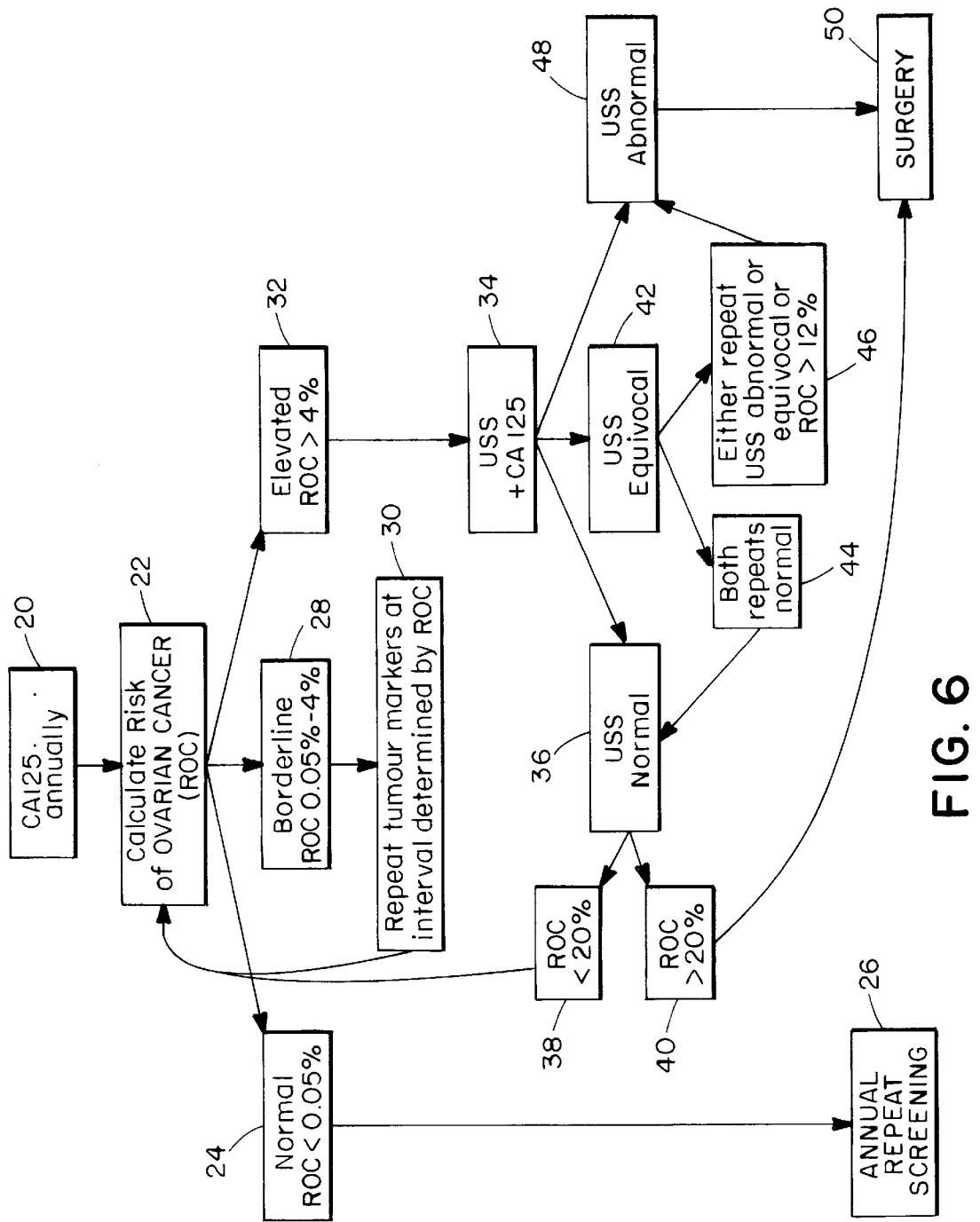
FIG. 6 is a flow chart of the appropriate courses of action based on the assessment of the risk of ovarian cancer.

FIG. 6 sets forth a flow chart of the appropriate courses of action based on the assessment of the risk of ovarian cancer. Once a marker level is determined at 20, the ROC is calculated (22). The individual is then triaged into one of three risk groups: normal, borderline, and elevated. Triage is based on threshold ROC values. Thresholds for ovarian cancer are set forth in Table 1.

TABLE 1

Risk Group Thresholds

| Risk Group | Threshold |
| --- | --- |
| Normal | ROC ≤ 0.05 |
| Borderline | 0.05 < ROC < 4.0 |
| Elevated | 4.0 ≤ ROC |

Women with a computed ROC that is less than or equal to 0.05% are triaged into the "normal" risk group (24); those with a computed ROC that is greater than 0.05% but less than 4.0% are triaged into the "borderline" risk group (28); and those with a computed ROC that is greater than or equal to 4.0% are triaged into the "elevated" risk group (32).

Once an individual is triaged into a particular risk group, a course of action can be determined. For individuals triaged into the "normal" risk group, the course of action is a retest of the level of the marker at a routine screening interval (26). A "routine screening interval" is the conventional length of time between examination and/or testing. For ovarian cancer, the measurement of the marker level can be performed concurrently with and annual gynecologic exam; thus, the "routine screening interval" is typically one year. Alternatively, the routine screening interval can be set for a shorter time interval (e.g., biannually), or a longer time interval. Longer time intervals may also result from individual delay in seeking routine examination.

Figure 7:
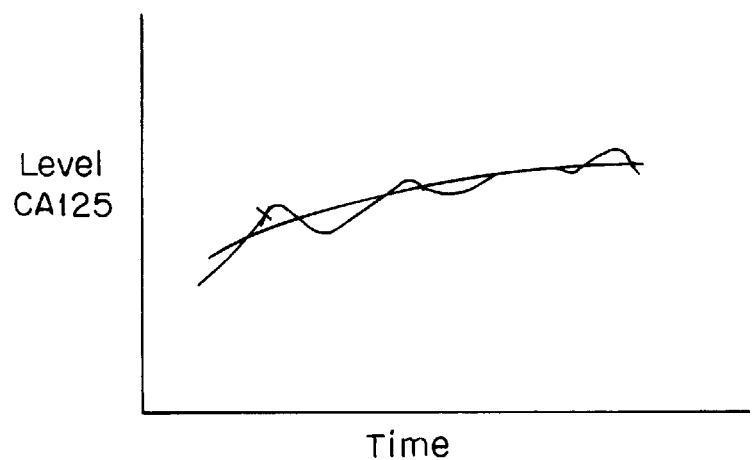
FIG. 7 is a graphic representation of the variability in marker levels as a function of time. The high slope at point X is due to short term and assay fluctuation.

For individuals triaged into the "borderline" risk group, the course of action is a retest (30) at a "retest interval," which is an interval that is substantially less than a routine screening interval. The threshold between "normal" and "borderline" (here, greater than 0.05%) is set to statistically require between 5% and 25%, preferably 15%, of a tested population to retest, as this was determined by clinical experience to be a reasonable but small fraction of the screened population to request returning for a subsequent sample before the routing screening interval. Preferably, the length of the retest interval is inversely related to the ROC, and varies between one and six months. For an ROC of 4%, the corresponding retest interval is one month; for an ROC of 0.05%, the corresponding retest interval is six months. ROC levels between these two threshold are linearly interpolated on the log(ROC) scale. The method of calculating risk utilizing the slope and intercept does not account for the interaction between time span and the variability of the assay measurement, in that high slopes can be generated over short periods of time simply by assay fluctuation. As shown in FIG. 7, the slope can vary considerably over a short time frame, yet remain relatively constant over a longer time frame. Thus, it is important to set the retests interval to a large enough interval (for example, one month for an ROC of 4%) to minimize the possibility that a high slope is due simply to individual variation. At the same time, the aim of screening is to detect the disease in the early stage, so the retest interval should be a short enough interval (for example, six months for an ROC of 0.05%) to detect a high proportion of disease in early stage. The current method approximates the optimal balance between these two competing aims.

Upon retesting of the individual, the ROC is again calculated (22), and the individual is again triaged into one of the three risk groups. The course of action for an individual triaged into the borderline group depends on whether the ROC upon retesting increases or decreases past the threshold for the group. If the ROC decreases such that the individual is triaged into the normal risk group upon retesting (24), then the course of action is the same as that for any individual triaged into the "normal" risk group: a retest of the level of the marker at the routine screening interval (26). If the ROC increases such that the individual is triaged into the "elevated" risk group upon retesting (32), then the course of action is the same as that for an individual triaged into the "elevated" risk group. If the ROC remains sufficiently constant such that the individual is triaged again into the "borderline" risk group (28), the retest interval is recalculated and the individual subjected to another retest of the marker level at the recomputed interval (30). The number of iterations wherein an individual is triaged into the "borderline" risk group is preferably limited to five, to avoid anxiety associated with repeat testing. After the fifth iteration with a borderline ROC level, the individual is treated as if she were triaged into the "elevated" risk group.

For individuals triaged into the "elevated" risk group (32), the course of action is subjecting the woman to a second line early detection modality to determine likelihood of presence of the disease (34). The threshold between "borderline" and "elevated" (here, greater than 4%) is set to statistically require between 0.5% and 2.5%, preferably 1.5%, of a tested population to undergo a test using a second line early detection modality, as this was determined by clinical experience to be a reasonable but small fraction of the screened population to subject to the second line early detection modality. It is relatively small yet balances the cost of the second line early detection modality and sensitivity. The thresholds between "normal" and "borderline", and between "borderline" and "elevated", can be lowered to improve the sensitivity of the screening program, or raised to reduce the cost associated with subsequent testing, as the discretion of an implementer of this approach to screening.

Appropriate second line early detection modalities (herein referred to a "secondary tests") for ovarian cancer include pelvic ultrasonographic examination, by transvaginal sonography (TVS); transabdominal sonography (TAS); and magnetic resonance imaging (MRI). TVS is the preferred second line modality for ovarian cancer. At the time of the secondary test, a retest of the marker level can also be conducted. Based upon the results of the secondary test and the retest of the marker level, the individual is again triaged into one of the three risk groups. If the results of the secondary test is normal (36), and the ROC is less than 20% (38), then course of action is retest of the marker level (30), recalculation of the ROC and triage of the individual into one of the three risk categories (22), as above. If the result of the secondary test is normal (36), yet the recalculated ROC as greater than 20% (40), then the appropriate course of action is surgery (50). If the result of the secondary test is abnormal (48) (for example, examination by ultrasound reveals an enlarged ovarian volume), the appropriate course of action is surgery (50). If the result of the secondary test is equivocal (42) (for example, examination by ultrasound reveals that the ovary volume is not abnormal, yet has suspicious morphology), then two subsequent repeats of the secondary test are performed, at intervals of approximately six weeks. If both of the repeat secondary tests are normal (44), the appropriate course of action is the same as if the original secondary test result was normal (36), as above. If the recalculated ROC is greater than 12% (46), or either of the repeat secondary tests is equivocal or abnormal (46), then the appropriate future action is surgery (50).

Previous approaches to early detection of ovarian cancer based on marker level measurements specify a single reference level, above which women are called screen positive. When the marker exceeds the reference level, a more expensive, second line screening modality (such as ultrasound) is used; for this reason, the references level is relatively high. In contrast, in the current method the subsequent action can be the less expensive, first line modality of further measurement of the marker level, with a rise in the marker level indicating the higher risk. Because the method of the invention utilizes iterative marker level measurement, the borderline level for a further measurement of the marker level can be set lower than previously used reference levels. Thus, the iterative method of the current invention allows earlier detection of cancer.

Figure 8A:
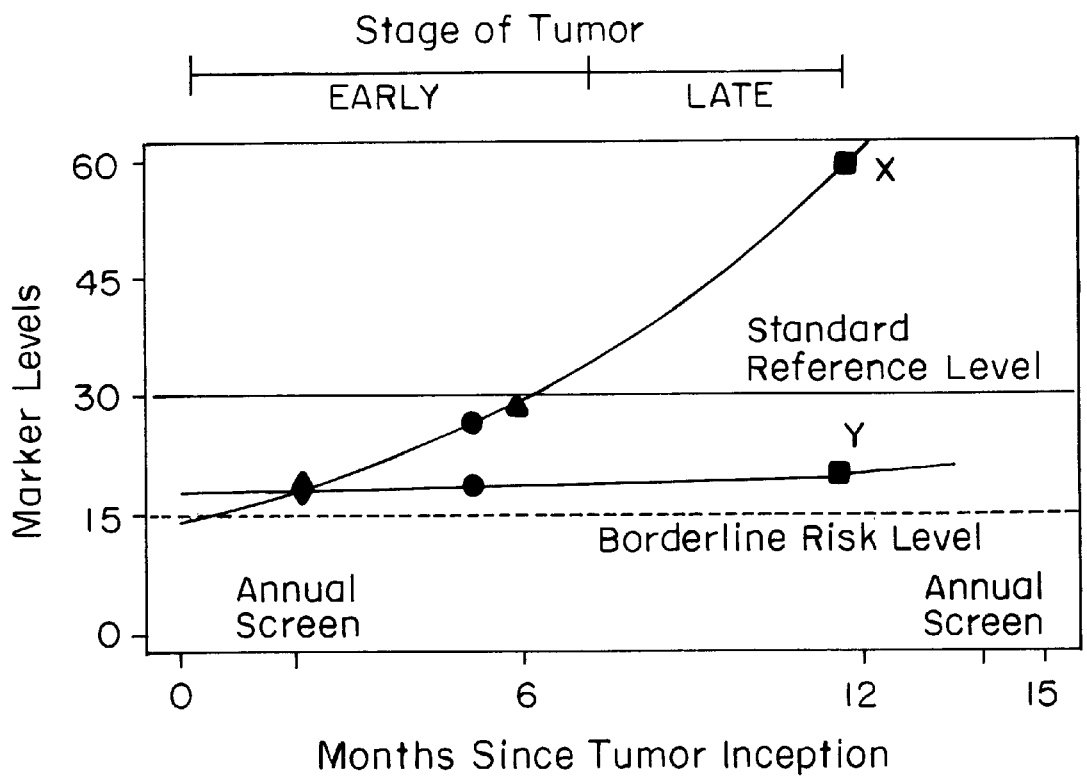
FIG. 8A is a graphic representation of the early detection of disease in the method of the invention, as compared with previous methods.
Figure 8B:
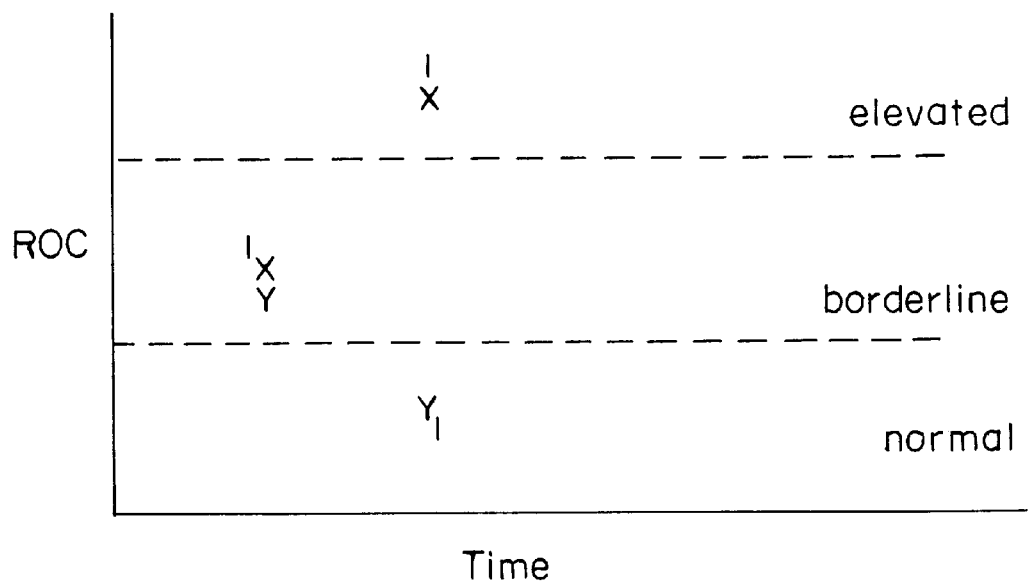
FIG. 8B is a graphic representation of the change in ROC status for the individuals depicted in FIG. 8A.

For example, FIG. 8A demonstrates that two individuals with the same initial marker level may have different disease outcomes. At an initial annual screening, individuals X and Y both have a marker level that is above the lower reference level of the current invention, yet below the standard reference level (diamond). If the standard reference level is used, individuals X and Y would both be retested at a second annual screening (squares). At that time, Y remains disease-free; however, individual X would have late-stage disease. In contrast, in the current method, both individuals X and Y are placed in the "borderline" risk group (FIG. 8B), with the resulting course of action that each is retested at the retest interval (FIG. 8A, circles). At that time, it would be noted that individual X has an increasing marker level, thereby resulting in an increased ROC (FIG. 8B), whereas individual Y has a constant or decreasing marker, resulting in a constant or lower ROC (FIG. 8B). Individual X has been triaged into the "elevated" risk group, and is referred to a second line early detection modality (FIG. 8A, triangle). Ultimately, her cancer is detected at an early stage. The method of the current invention thus detects all cases of ovarian cancer which previous approaches would detect (i.e., detection of the late-stage cancer of individual X at the second annual screening), and in addition detects those cases which are in early stage (i.e., detection of early-stage cancer of individual X at the retest interval). Thus, the sensitivity for detection in early stage disease is increased, and mortality due to the disease is reduced.

Figure 9:
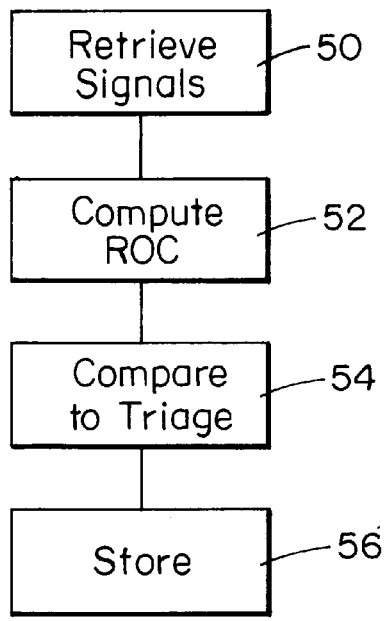
FIG. 9 is a flow chart for the program stored in memory for execution on a data processing system, for assessing the risk of a woman for ovarian cancer.

In accordance with another embodiment of the current invention, memory storing a program for execution on a data processing system is available for assessing the risk of a woman for ovarian cancer. As shown in FIG. 9, the memory includes a receiver for signals representative of levels of a marker for ovarian cancer (50); central processing unit for computing the ROC from one or more levels of the marker (52) and for comparing the computed ROC to thresholds to triage the woman into normal, borderline or elevated risk groups (54); and a storage medium for the marker levels (56), for subsequent computations of ROC. The memory can further comprise a means for creating a bar graph display indicating the computed risk, the display being green when the risk is less than the normal threshold, yellow when the risk is between the borderline thresholds, and red when the risk is greater than the elevated threshold.

Figure 10:
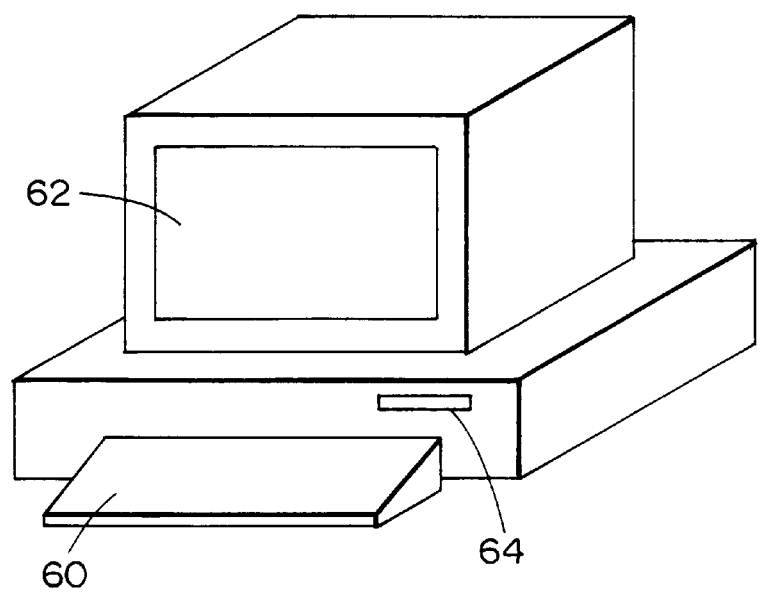
FIG. 10 is a diagram for the computer system, comprising memory storing a program for execution, for assessing the risk of a woman for ovarian cancer.

A computer system is also available, as shown in FIG. 10, comprising a keyboard input device (60) for receiving marker levels, a display (62) for displaying risk of ovarian cancer and courses of action based on the ROC, and a memory (64) as described above.

While the above discussion pertains to assessing the risk of an individual for ovarian cancer, the methods described herein are applicable to any disease for which a biological marker correlating with a disease sate is available, and can be used as a diagnostic indicator for any such disease. The thresholds for the risk group will vary, depending on the disease and the marker or markers used.

TABLE 2

| | | | | | | | | | |
|---|---|---|---|---|---|---|---|---|---|
| 1.0099 | 0.4795 | 2.6374 | 0.0067 | 0.0269 | 4.9954 | 1.9448 | 2.6165 | 0.0123 | 0.0305 |
| 0.8238 | 0.3206 | 2.6359 | 0.0085 | 0.0285 | 4.1167 | 1.6259 | 2.6557 | 0.0155 | 0.0291 |
| 1.7236 | 0.3530 | 2.6622 | 0.0007 | 0.0291 | 1.8513 | 0.9700 | 2.6432 | 0.0119 | 0.0280 |
| 2.9772 | 0.9660 | 2.6441 | 0.0025 | 0.0302 | 0.4507 | −0.2813 | 2.6559 | 0.0101 | 0.0267 |
| 1.7073 | 0.1026 | 2.6770 | −0.0015 | 0.0296 | −1.4399 | −0.3394 | 2.6509 | 0.0090 | 0.0268 |
| 2.5688 | 0.4641 | 2.6652 | 0.0062 | 0.0281 | −2.7688 | 1.1192 | 2.6542 | 0.0044 | 0.0284 |
| 1.7270 | −0.1553 | 2.6381 | 0.0063 | 0.0284 | 1.8855 | 0.6877 | 2.6276 | 0.0129 | 0.0279 |
| 2.4494 | −0.0452 | 2.6254 | 0.0152 | 0.0283 | 2.5110 | 0.3957 | 2.6481 | 0.0154 | 0.0273 |
| 2.3503 | 0.7394 | 2.6424 | 0.0077 | 0.0282 | 2.7140 | 0.3824 | 2.6473 | 0.0099 | 0.0284 |
| 1.4795 | 0.3209 | 2.6555 | 0.0128 | 0.0274 | 2.2289 | 0.2939 | 2.6727 | 0.0111 | 0.0275 |
| 3.9082 | 0.6031 | 2.6515 | 0.0128 | 0.0269 | 2.4482 | 0.0187 | 2.6591 | 0.0078 | 0.0281 |
| 1.4847 | 2.2387 | 2.6552 | 0.0107 | 0.0260 | 1.6324 | −0.6386 | 2.6560 | 0.0098 | 0.0279 |
| −2.1320 | 0.5757 | 2.6429 | 0.0058 | 0.0270 | 2.7759 | 0.2501 | 2.6485 | 0.0088 | 0.0280 |
| −0.8840 | 0.5316 | 2.6611 | 0.0186 | 0.0281 | 5.3864 | 0.9579 | 2.6542 | 0.0132 | 0.0278 |
| 0.4636 | 1.0452 | 2.6475 | 0.0152 | 0.0278 | 4.0161 | 0.6088 | 2.6424 | 0.0131 | 0.0293 |
| −1.4354 | 0.7765 | −2.6378 | 0.0244 | 0.0283 | 5.1315 | 0.0116 | 2.6677 | 0.0169 | 0.0291 |
| 1.8580 | 0.6886 | 2.6596 | 0.0177 | 0.0271 | 4.2429 | −0.4001 | 2.6518 | 0.0231 | 0.0286 |

TABLE 2-continued

| | | | | | | | | | |
|---|---|---|---|---|---|---|---|---|---|
| 3.0502 | 0.2413 | 2.6517 | 0.0136 | 0.0274 | 0.9617 | 0.2084 | 2.6367 | 0.0193 | 0.0293 |
| 0.2088 | −0.1445 | 2.6409 | 0.0067 | 0.0276 | 0.9306 | 0.8899 | 2.6500 | 0.0070 | 0.0286 |
| 1.8926 | −1.1937 | 2.6429 | −0.0017 | 0.0274 | 1.2297 | 0.2313 | 2.6634 | −0.0036 | 0.0290 |
| 2.6553 | 0.5389 | 2.6468 | 0.0032 | 0.0282 | 0.4932 | 1.4498 | 2.6585 | 0.0041 | 0.0293 |
| 1.1740 | 0.2920 | 2.6517 | 0.0134 | 0.0280 | 1.3441 | −0.1340 | 2.6459 | 0.0115 | 0.0295 |
| 2.6419 | 0.2983 | 2.6602 | 0.0192 | 0.0274 | 2.3298 | 0.0466 | 2.6647 | 0.0151 | 0.0287 |
| 3.1075 | 0.4384 | 2.6562 | 0.0072 | 0.0283 | 2.6455 | −0.7596 | 2.6525 | 0.0171 | 0.0290 |
| 4.6214 | 0.5384 | 2.6461 | 0.0036 | 0.0283 | 1.2596 | −0.3879 | 2.6617 | 0.0081 | 0.0290 |
| 5.3071 | 0.0029 | 2.6673 | 0.0060 | 0.0294 | 2.7172 | 1.3295 | 2.6743 | 0.0068 | 0.0284 |
| 6.3176 | 0.2133 | 3.6488 | −0.0033 | 0.0297 | 2.1809 | 1.0482 | 2.6481 | 0.0134 | 0.0281 |
| 2.0984 | 0.9646 | 2.6577 | 0.0078 | 0.0293 | 3.3893 | −0.0240 | 2.6376 | 0.0119 | 0.0283 |
| 5.4400 | 0.0767 | 2.6563 | 0.0046 | 0.0296 | 1.4319 | 0.3274 | 2.6449 | 0.0107 | 0.0289 |
| 2.2919 | 0.9984 | 2.6468 | 0.0010 | 0.0297 | 0.9632 | 0.7925 | 2.6561 | 0.0080 | 0.0283 |
| 0.0624 | 0.7756 | 2.6316 | 0.0050 | 0.0279 | −0.0517 | 0.8222 | 2.6550 | 0.0049 | 0.0293 |
| 0.0903 | 0.6841 | 2.6554 | 0.0049 | 0.0281 | 3.4388 | 1.1389 | 2.6751 | 0.0103 | 0.0292 |
| 1.4539 | 0.7637 | 2.6626 | 0.0036 | 0.0270 | 1.4772 | 1.4330 | 2.6483 | 0.0078 | 0.0294 |
| 1.7765 | 0.3648 | 2.6580 | 0.0147 | 0.0275 | 1.5651 | 2.6823 | 2.6431 | −0.0009 | 0.0288 |
| 2.8074 | 0.1563 | 2.6773 | 0.0142 | 0.0272 | 2.2576 | 1.4773 | 2.6658 | 0.0054 | 0.0303 |
| 2.2494 | −0.1657 | 2.6674 | 0.0120 | 0.0264 | 5.1376 | 1.5096 | 2.6515 | −0.0030 | 0.0296 |
| 1.9571 | 0.3216 | 2.6597 | 0.0165 | 0.0273 | 0.2110 | 0.5084 | 2.6397 | 0.0070 | 0.0290 |
| 3.2765 | 0.8656 | 2.6476 | 0.0178 | 0.0275 | 1.2172 | −0.0667 | 2.6375 | 0.0022 | 0.0288 |
| 2.8438 | −0.5374 | 2.6353 | 0.0217 | 0.0279 | 2.4474 | −0.1737 | 2.6542 | 0.0004 | 0.0282 |
| 4.2653 | 0.1520 | 2.6354 | 0.0262 | 0.0310 | 1.6769 | 0.7392 | 2.6566 | −0.0015 | 0.0298 |
| 3.0546 | 0.0148 | 2.6548 | 0.0159 | 0.0323 | 3.4623 | 0.7399 | 2.6395 | 0.0083 | 0.0292 |
| 3.3524 | 0.2952 | 2.6576 | 0.0108 | 0.0328 | 1.2033 | 0.2894 | 2.6432 | 0.0116 | 0.0287 |
| 0.7209 | 0.8763 | 2.6491 | 0.0141 | 0.0332 | 2.6478 | −0.4033 | 2.6713 | 0.0133 | 0.0283 |
| 2.0480 | 0.4667 | 2.6483 | 0.0070 | 0.0308 | 2.7645 | 0.8763 | 2.6569 | 0.0076 | 0.0266 |
| −2.5065 | 0.7837 | 2.6843 | 0.0032 | 0.0300 | 4.0696 | 0.1331 | 2.6518 | 0.0129 | 0.0269 |
| 1.1399 | 1.2462 | 2.6490 | 0.0037 | 0.0305 | 3.6954 | 0.0114 | 2.6587 | 0.0153 | 0.0269 |
| 1.7324 | 0.5309 | 2.6466 | 0.0021 | 0.0289 | 2.5230 | −0.4317 | 2.6570 | 0.0175 | 0.0273 |
| 3.5020 | 0.0241 | 2.6211 | 0.0071 | 0.0294 | 3.3542 | 0.7178 | 2.6593 | 0.0206 | 0.0268 |
| 0.5020 | 0.1637 | 2.6475 | 0.0069 | 0.0284 | 1.3306 | 0.7408 | 2.6479 | 0.0186 | 0.0266 |
| 1.1781 | −0.1946 | 2.6388 | 0.0098 | 0.0281 | 1.2436 | 1.4600 | 2.6311 | 0.0252 | 0.0267 |
| 4.3701 | 2.0096 | 2.6506 | 0.0108 | 0.0287 | 1.9078 | 1.4190 | 2.6502 | 0.0190 | 0.0255 |
| 5.3849 | 0.5420 | 2.6339 | 0.0211 | 0.0274 | 0.7855 | 1.0496 | 2.6676 | 0.0001 | 0.0247 |
| 4.0916 | −0.3529 | 2.6531 | 0.0135 | 0.0285 | −0.2603 | 1.4978 | 2.6420 | 0.0075 | 0.0238 |
| 5.7893 | −0.4638 | 2.6348 | 0.0093 | 0.0268 | 2.6686 | 0.0423 | 2.6473 | 0.0139 | 0.0253 |
| 2.2090 | −0.4400 | 2.6421 | 0.0098 | 0.0265 | 2.6686 | 0.5288 | 2.6571 | 0.0100 | 0.0252 |
| 1.6812 | 0.1691 | 2.6313 | 0.0113 | 0.0271 | 1.8062 | 2.1412 | 2.6542 | 0.0138 | 0.0280 |
| 2.9033 | −0.4850 | 2.6392 | 0.0069 | 0.0271 | 3.5645 | 0.7435 | 2.6354 | 0.0223 | 0.0273 |
| 1.8555 | −0.2973 | 2.6419 | 0.0106 | 0.0272 | 4.8631 | 0.9560 | 2.6426 | 0.0096 | 0.0266 |
| 1.3720 | 0.3154 | 2.6411 | 0.0091 | 0.0262 | 4.1168 | −0.2003 | 2.6621 | 0.0048 | 0.0266 |
| 0.6551 | 0.6433 | 2.6377 | 0.0053 | 0.0266 | 2.3478 | 1.6221 | 2.6429 | 0.0100 | 0.0278 |
| 0.9892 | 0.4938 | 2.6553 | 0.0133 | 0.0253 | 3.2414 | 1.9463 | 2.6707 | 0.0052 | 0.0292 |
| 1.2561 | 0.4499 | 2.6580 | 0.0138 | 0.0263 | 3.5835 | 1.0479 | 2.6556 | 0.0087 | 0.0277 |
| 4.2230 | 1.6353 | 2.6326 | 0.0203 | 0.0257 | 4.2748 | −1.0994 | 2.6608 | 0.0102 | 0.0271 |
| 3.4926 | 1.2350 | 2.6442 | 0.0396 | 0.0277 | 4.2617 | −0.5831 | 2.6541 | 0.0116 | 0.0273 |
| 4.0477 | 1.2611 | 2.6328 | 0.0189 | 0.0269 | 2.2422 | 0.3819 | 2.6680 | 0.0066 | 0.0277 |
| 2.3172 | −0.1990 | 2.6287 | 0.0189 | 0.0270 | 0.6645 | 0.7555 | 2.6597 | 0.0099 | 0.0290 |
| 1.7433 | 0.3250 | 2.6448 | 0.0204 | 0.0285 | 5.4454 | 0.2669 | 2.6626 | 0.0153 | 0.0284 |
| 1.0381 | −0.7542 | 2.6333 | 0.0281 | 0.0281 | 2.0754 | −0.1687 | 2.6377 | 0.0130 | 0.0295 |
| 0.0082 | −0.6177 | 2.6549 | 0.0220 | 0.0282 | 1.9459 | −0.6060 | 2.6358 | 0.0089 | 0.0289 |
| 3.5856 | −0.0326 | 2.6608 | 0.0120 | 0.0266 | 1.2459 | 0.3690 | 2.6375 | 0.0189 | 0.0289 |
| 1.8890 | −0.0064 | 2.6425 | 0.0123 | 0.0262 | 2.9208 | −0.6669 | 2.6569 | 0.0168 | 0.0280 |
| 1.8989 | 0.3023 | 2.6335 | 0.0224 | 0.0265 | 2.6819 | −0.6204 | 2.6631 | 0.0172 | 0.0265 |
| 1.4821 | −0.0517 | 2.6531 | 0.0203 | 0.0271 | 6.2859 | 0.4990 | 2.6715 | 0.0042 | 0.0269 |
| 0.3669 | 0.6792 | 2.6428 | 0.0192 | 0.0265 | 2.7920 | 0.3397 | 2.6665 | 0.0035 | 0.0266 |
| 3.7105 | −0.1628 | 2.6423 | 0.0077 | 0.0276 | 3.2285 | 0.8799 | 2.6462 | 0.0140 | 0.0263 |
| 2.8831 | −0.3025 | 2.6526 | 0.0086 | 0.0267 | 5.0736 | 0.6056 | 2.6537 | 0.0153 | 0.0271 |
| 2.5319 | −0.4989 | 2.6439 | −0.0002 | 0.0264 | 3.4753 | −0.1649 | 2.6475 | 0.0206 | 0.0273 |
| 4.0352 | 0.2628 | 2.6598 | 0.0072 | 0.0258 | 4.5882 | −0.8294 | 2.6525 | 0.0272 | 0.0270 |
| 0.5929 | −0.2826 | 2.6475 | 0.0146 | 0.0269 | 3.3924 | −0.0552 | 2.6758 | 0.0199 | 0.0261 |
| 0.0431 | 0.8334 | 2.6469 | 0.0146 | 0.0250 | 1.9251 | −0.7361 | 2.6480 | 0.0199 | 0.0273 |
| −0.6452 | 0.6260 | 2.6509 | 0.0110 | 0.0257 | −1.3261 | −0.3767 | 2.6635 | 0.0237 | 0.0270 |
| 3.6289 | 0.2880 | 2.6506 | 0.0172 | 0.0349 | 1.8159 | −0.1598 | 2.6504 | 0.0164 | 0.0284 |
| 3.1801 | −0.5438 | 2.6472 | 0.0080 | 0.0251 | 4.8621 | 0.0865 | 2.6449 | 0.0207 | 0.0286 |
| 3.9453 | −0.1008 | 2.6442 | 0.0176 | 0.0253 | 1.8508 | 0.8240 | 2.6530 | 0.0113 | 0.0293 |
| 2.7131 | 0.1908 | 2.6486 | 0.0129 | 0.0247 | 4.6145 | 0.2686 | 2.6420 | 0.0115 | 0.0280 |
| 2.0232 | −0.2053 | 2.6390 | 0.0142 | 0.0255 | 2.1998 | 0.2466 | 2.6359 | 0.0215 | 0.0379 |
| 3.3969 | −0.1773 | 2.6299 | 0.0229 | 0.0259 | 0.5857 | 0.0532 | 2.6520 | 0.0172 | 0.0278 |
| 1.3822 | −0.4637 | 2.6452 | 0.0241 | 0.0276 | 1.4458 | 0.9532 | 3.6698 | 0.0157 | 0.0284 |
| 2.7488 | −0.1874 | 2.6344 | 0.0116 | 0.0274 | 1.0942 | −0.4146 | 2.6411 | 0.0238 | 0.0270 |
| 5.0651 | −0.5417 | 3.6620 | 0.0059 | 0.0282 | 3.1185 | −0.6195 | 2.6355 | 0.0190 | 0.0270 |
| 3.8201 | −0.1818 | 2.6567 | 0.0064 | 0.0289 | 4.3734 | 0.9311 | 2.6432 | 0.0270 | 0.0263 |
| 7.0122 | 1.2360 | 2.6603 | 0.0100 | 0.0282 | 2.0681 | 0.1833 | 2.6563 | 0.0125 | 0.0280 |
| 0.0248 | 0.5870 | 2.6399 | 0.0221 | 0.0272 | 4.6253 | 0.1007 | 2.6508 | 0.0224 | 0.0280 |
| 2.9624 | 0.7575 | 2.6348 | 0.0255 | 0.0285 | 4.6844 | −0.1010 | 2.6379 | 0.0165 | 0.0278 |
| 0.5051 | 0.2710 | 2.6454 | 0.0177 | 0.0288 | 5.6332 | 0.1337 | 2.6377 | 0.0090 | 0.0286 |
| 0.9839 | −0.4375 | 2.6197 | 0.0129 | 0.0284 | 1.4749 | 0.4333 | 2.6651 | 0.0005 | 0.0378 |

TABLE 2-continued

| | | | | | | | | | |
|---|---|---|---|---|---|---|---|---|---|
| 4.6789 | −0.8653 | 2.6598 | 0.0052 | 0.0272 | 1.0641 | 2.0429 | 2.6611 | 0.0066 | 0.0289 |
| 3.2420 | 0.9746 | 2.6565 | 0.0070 | 0.0280 | 0.4856 | 0.4429 | 2.6540 | 0.0127 | 0.0274 |
| 3.2979 | 0.6786 | 2.6366 | 0.0131 | 0.0283 | 1.3801 | 0.2372 | 2.6421 | 0.0155 | 0.0269 |
| 2.2344 | 1.0049 | 2.6438 | 0.0133 | 0.0202 | 3.3259 | −0.6361 | 2.6342 | 0.0122 | 0.0277 |
| 3.2143 | 2.1972 | 2.6580 | 0.0202 | 0.0281 | 1.3237 | 0.0111 | 2.6116 | 0.0201 | 0.0277 |
| 3.4499 | 1.8662 | 2.6447 | 0.0180 | 0.0289 | −0.0109 | 0.4826 | 2.6522 | 0.0159 | 0.0273 |
| 3.0171 | 2.4353 | 2.6393 | 0.0173 | 0.0281 | 2.3904 | 1.5241 | 2.6460 | 0.0177 | 0.0274 |
| 3.1228 | 2.0886 | 2.6438 | 0.0140 | 0.0282 | 4.2128 | 2.2542 | 2.6543 | 0.0192 | 0.0268 |
| 2.3351 | −0.5662 | 2.6399 | 0.0076 | 0.0283 | 5.3789 | 1.2913 | 2.6427 | 0.0195 | 0.0279 |
| 1.4037 | −0.7996 | 2.6501 | 0.0047 | 0.0279 | 1.0288 | 0.3169 | 2.6447 | 0.0242 | 0.0268 |
| 6.1289 | 0.4750 | 2.6498 | 0.0113 | 0.0293 | 5.8788 | 1.4641 | 2.6556 | 0.0306 | 0.0276 |
| 3.2978 | 0.3765 | 3.6397 | 0.0254 | 0.0287 | 6.4206 | 0.7133 | 2.6488 | 0.0397 | 0.0279 |
| 2.8824 | 0.9049 | 2.6161 | 0.0271 | 0.0286 | 5.6105 | 0.4041 | 2.6477 | 0.0233 | 0.0285 |
| 2.2219 | 0.3404 | 2.6649 | 0.0203 | 0.0274 | 4.1774 | 0.1554 | 2.6651 | 0.0272 | 0.0282 |
| 2.1229 | 0.3822 | 2.6562 | 0.0213 | 0.0279 | 3.1435 | 0.4356 | 2.6643 | 0.0283 | 0.0281 |
| 3.2567 | −0.6389 | 2.6457 | 0.0175 | 0.0270 | 3.0936 | −0.8610 | 2.6291 | 0.0325 | 0.0276 |
| 3.8677 | −0.4193 | 2.6460 | 0.0147 | 0.0273 | −0.3288 | 0.4535 | 2.6334 | 0.0292 | 0.0279 |
| 1.3385 | −0.4066 | 2.6378 | 0.0131 | 0.0264 | 3.7979 | 0.7429 | 2.6457 | 0.0268 | 0.0260 |
| 0.9525 | 1.1426 | 2.6501 | 0.0244 | 0.0265 | 3.5172 | 0.9505 | 2.6584 | 0.0212 | 0.0259 |
| 1.2131 | 1.5904 | 2.6407 | 0.0159 | 0.0261 | 7.2051 | 1.4102 | 2.6511 | 0.0118 | 0.0265 |
| 1.2481 | 1.5795 | 2.6437 | 0.0213 | 0.0281 | 2.9198 | 0.4142 | 2.6627 | 0.0168 | 0.0256 |
| 4.3241 | 0.9650 | 2.6151 | 0.0331 | 0.0263 | 2.8920 | 0.5096 | 2.6511 | 0.0133 | 0.0266 |
| 4.4874 | −0.4599 | 2.6432 | 0.0297 | 0.0263 | 2.8603 | 0.3942 | 2.6403 | 0.0193 | 0.0275 |
| 5.2774 | 0.2012 | 2.6544 | 0.0227 | 0.0283 | −3.8882 | 0.5734 | 2.6482 | 0.0100 | 0.0268 |
| 3.4734 | 0.8459 | 2.6559 | 0.0165 | 0.0276 | 0.4462 | 0.2610 | 2.6598 | 0.0129 | 0.0252 |
| 1.5196 | 0.1079 | 2.6403 | 0.0034 | 0.0264 | 2.0422 | −0.0808 | 2.6427 | 0.0110 | 0.0272 |
| 1.4573 | −0.1556 | 2.6529 | 0.0161 | 0.0277 | 3.7280 | 1.0772 | 2.6304 | 0.0147 | 0.0278 |
| 4.0734 | −0.0146 | 2.6502 | 0.0168 | 0.0282 | 2.9593 | 0.5719 | 2.6495 | 0.0091 | 0.0278 |
| 5.1582 | −0.1321 | 2.6504 | 0.0154 | 0.0276 | 2.9387 | 0.6617 | 2.6403 | 0.0049 | 0.0281 |
| 1.6174 | −0.6162 | 2.6634 | 0.0190 | 0.0297 | 2.2359 | 0.5467 | 2.6424 | 0.0155 | 0.0271 |
| 4.0999 | 1.6757 | 2.6351 | 0.0164 | 0.0306 | 3.4838 | 0.3673 | 2.6402 | 0.0278 | 0.0277 |
| 4.6223 | 1.8929 | 2.6524 | 0.0149 | 0.0305 | 4.7579 | 1.7166 | 2.6621 | 0.0162 | 0.0201 |
| 3.0558 | 0.2319 | 2.6617 | 0.0224 | 0.0275 | 0.9775 | 0.1679 | 2.6546 | 0.0051 | 0.0267 |
| 4.2514 | −1.0392 | 2.6753 | 0.0238 | 0.0260 | 3.4743 | −0.0970 | 2.6514 | 0.0213 | 0.0267 |
| 2.4499 | 0.1913 | 2.6491 | 0.0250 | 0.0260 | 2.6520 | −0.3729 | 2.6555 | 0.0200 | 0.0268 |
| 4.7913 | 0.5536 | 2.6457 | 0.0249 | 0.0263 | 3.4109 | 0.1177 | 2.6377 | 0.0144 | 0.0256 |
| 3.4071 | 1.2304 | 2.6545 | 0.0244 | 0.0277 | 2.2971 | 1.3729 | 2.6635 | −0.0008 | 0.0263 |
| 1.2402 | 1.1786 | 2.6454 | 0.0178 | 0.0272 | 3.7685 | −0.1694 | 2.6511 | −0.0029 | 0.0269 |
| 0.9684 | 1.0373 | 2.6476 | 0.0189 | 0.0270 | 2.8279 | −0.4604 | 2.6609 | −0.0085 | 0.0270 |
| 3.4595 | 1.3686 | 2.6494 | 0.0205 | 0.0290 | 3.5623 | −0.5980 | 2.6673 | −0.0045 | 0.0268 |
| 2.3979 | 1.5256 | 2.6625 | 0.0167 | 0.0287 | 2.6882 | 0.0639 | 2.6459 | 0.0009 | 0.0261 |
| 1.8274 | −1.2548 | 2.6360 | 0.0126 | 0.0275 | 4.5225 | −0.3085 | 2.6536 | 0.0014 | 0.0254 |
| 3.0529 | −0.1015 | 2.6466 | 0.0248 | 0.0274 | 3.6526 | 1.8264 | 2.6636 | −0.0006 | 0.0265 |
| 4.2845 | −0.9405 | 2.6409 | 0.0185 | 0.0267 | 4.6967 | 1.1367 | 2.6495 | 0.0121 | 0.0266 |
| 4.2576 | −1.2961 | 2.6384 | 0.0098 | 0.0263 | 2.1301 | −0.7044 | 2.6529 | 0.0166 | 0.0259 |
| 1.8532 | 0.2340 | 2.6502 | 0.0112 | 0.0268 | 4.2762 | 0.2028 | 2.6259 | 0.0287 | 0.0256 |
| 2.3658 | 0.4556 | 2.6503 | 0.0138 | 0.0268 | 4.3573 | −0.7058 | 2.6623 | −0.0235 | 0.0241 |
| −0.0765 | 0.5799 | 2.6412 | 0.0098 | 0.0276 | 3.2484 | −0.6068 | 2.6604 | 0.0263 | 0.0256 |
| 0.6068 | 1.9138 | 2.6670 | 0.0159 | 0.0272 | 2.3150 | 0.3838 | 2.6359 | 0.0189 | 0.0256 |
| 0.7795 | 3.0143 | 2.6633 | 0.0085 | 0.0268 | 2.4674 | 0.0767 | 2.6533 | 0.0100 | 0.0262 |
| 2.6302 | 0.5857 | 2.6441 | 0.0132 | 0.0268 | 3.6872 | −0.3802 | 2.6633 | −0.0017 | 0.0270 |
| 2.3896 | −0.1482 | 2.6484 | 0.0136 | 0.0259 | 4.2593 | 0.3231 | 2.6709 | 0.0046 | 0.0280 |
| 0.9996 | 0.8614 | 2.6424 | 0.0143 | 0.0269 | 2.3995 | 1.0908 | 2.6628 | 0.0104 | 0.0273 |
| 0.3206 | 1.7205 | 2.6221 | 0.0283 | 0.0283 | 1.0033 | 0.0602 | 2.6500 | 0.0035 | 0.0263 |
| −0.9574 | 1.5233 | 2.6500 | 0.0266 | 0.0290 | 0.9218 | 1.9083 | 2.6392 | 0.0146 | 0.0275 |
| 0.3145 | 1.0702 | 2.6471 | 0.0271 | 0.0278 | −1.4739 | 0.8555 | 2.6547 | 0.0068 | 0.0366 |
| 0.9822 | 0.0562 | 2.6508 | 0.0245 | 0.0287 | 4.1403 | −0.5153 | 2.6518 | 0.0097 | 0.0265 |
| 1.0848 | 0.8120 | 2.6585 | 0.0344 | 0.6304 | 2.3858 | 0.3037 | 2.6584 | −0.0047 | 0.0262 |
| 2.5617 | 0.9379 | 2.6477 | 0.0240 | 0.0288 | 3.3598 | 3.9377 | 2.6676 | 0.0058 | 0.0266 |
| 1.8837 | −0.3464 | 2.6472 | 0.0170 | 0.0299 | 1.4439 | 1.4509 | 2.6513 | 0.0050 | 0.0266 |
| 2.8369 | 0.1251 | 2.6482 | 0.0144 | 0.0284 | 1.3224 | 0.3870 | 2.6727 | −0.0039 | 0.0269 |
| 2.4522 | 0.9358 | 2.6453 | 0.0235 | 0.0280 | 2.5823 | 1.9315 | 2.6450 | 0.0079 | 0.0279 |
| 1.9589 | −1.3417 | 2.6415 | 0.0240 | 0.0277 | 3.2087 | 0.7643 | 2.6466 | 0.0055 | 0.0272 |
| 1.3455 | 0.6804 | 2.6231 | 0.0233 | 0.0279 | 2.8025 | −0.0533 | 2.6661 | 0.0052 | 0.0274 |
| 2.5731 | 0.6440 | 2.6563 | 0.0205 | 0.0284 | 3.4046 | −0.5692 | 2.6662 | 1.0054 | 0.0260 |
| 2.3715 | 1.0267 | 2.6350 | 0.0190 | 0.0265 | 1.9658 | −0.2587 | 2.6588 | 0.0142 | 0.0267 |
| 0.8248 | 0.0342 | 2.6443 | 0.0188 | 0.0255 | 0.9427 | 0.0930 | 2.6652 | 0.0080 | 0.0274 |
| 4.0151 | 1.4206 | 2.6550 | 0.0107 | 0.0253 | 2.8967 | −0.6680 | 2.6548 | 0.0182 | 0.0274 |
| 2.3502 | 0.9319 | 2.6543 | 0.0155 | 0.0267 | 5.4560 | 0.3104 | 2.6515 | 0.0132 | 0.0266 |
| 2.7333 | 0.7978 | 2.6222 | 0.0166 | 0.0272 | 3.7057 | −0.8309 | 2.6644 | 0.0078 | 0.0269 |
| 2.6753 | 0.3975 | 2.6486 | 0.0264 | 0.0273 | 3.6215 | −1.2732 | 2.6478 | 0.0118 | 0.0266 |
| 1.9267 | −0.2385 | 2.6543 | 0.0234 | 0.0272 | 2.8189 | 0.3384 | 2.6340 | 0.0238 | 0.0268 |
| 1.1337 | 0.5564 | 2.6713 | 0.0188 | 0.0277 | 3.2183 | 1.2530 | 2.6493 | 0.0178 | 0.0269 |
| 2.7561 | −0.5895 | 2.6696 | 0.0150 | 0.0268 | 2.5761 | 0.7542 | 2.6567 | 0.0173 | 0.0266 |
| 2.7175 | −0.6888 | 2.6656 | 0.0085 | 0.0278 | 4.0201 | 1.2854 | 2.6544 | 0.0083 | 0.0256 |
| 2.4440 | 0.5642 | 2.6626 | 0.0045 | 0.0282 | 3.8720 | 0.1014 | 2.6478 | 0.0094 | 0.0263 |
| 2.8028 | −0.2576 | 2.6617 | 0.0184 | 0.0289 | 3.0358 | 0.1117 | 2.6610 | 0.0040 | 0.0276 |
| 6.3446 | 0.3900 | 2.6728 | 0.0234 | 0.0286 | 2.7408 | 0.1807 | 2.6403 | 0.0144 | 0.0275 |
| 2.4150 | −0.0385 | 2.6543 | 0.0274 | 0.0278 | 2.7843 | 0.2746 | 2.6397 | 0.0152 | 0.0295 |

TABLE 2-continued

| | | | | | | | | | |
|---|---|---|---|---|---|---|---|---|---|
| 1.9136 | 0.1868 | 2.6491 | 0.0179 | 0.0277 | 4.4952 | −0.8797 | 2.6676 | 0.0180 | 0.0295 |
| 0.0907 | 1.2002 | 2.6507 | 0.0147 | 0.0273 | 1.6285 | 0.3092 | 2.6492 | 0.0146 | 0.0299 |
| 3.4023 | −0.1532 | 2.6522 | 0.0213 | 0.0262 | 1.5632 | 0.3186 | 2.6561 | 0.0135 | 0.0281 |
| 4.5587 | −0.3275 | 2.6518 | 0.0169 | 0.0273 | 3.2917 | 0.1881 | 2.6698 | 0.0162 | 0.0294 |
| 6.0413 | −0.3415 | 2.6657 | 0.0234 | 0.0271 | 5.2697 | 0.1221 | 2.6352 | 0.0161 | 0.0284 |
| 6.2663 | −0.6160 | 2.6260 | 0.0194 | 0.0275 | 2.5333 | −1.2059 | 2.6512 | 0.0189 | 0.0284 |
| 5.2508 | 1.0085 | 2.6420 | 0.0176 | 0.0278 | 1.6533 | 0.7955 | 2.6393 | 0.0242 | 0.0264 |
| 4.6750 | −0.2285 | 2.6368 | 0.0050 | 0.0278 | 1.6166 | −0.5779 | 2.6373 | 0.0194 | 0.0266 |
| 3.4859 | 0.3573 | 2.6514 | 0.0089 | 0.0273 | 2.4632 | 0.1684 | 2.6402 | 0.0137 | 0.0282 |
| 3.2865 | −0.4428 | 2.6438 | 0.0110 | 0.0272 | 2.0405 | 0.2591 | 2.6443 | 0.0082 | 0.0298 |
| 0.9737 | 0.2788 | 2.6436 | 0.0119 | 0.0266 | 1.6062 | −0.1324 | 2.6497 | 0.0129 | 0.0277 |
| 1.8191 | −0.3396 | 2.6394 | 0.0176 | 0.0269 | 1.4704 | 0.8413 | 2.6411 | 0.0071 | 0.0273 |
| 1.8988 | −0.7615 | 2.6696 | 0.0140 | 0.0262 | 1.1826 | 0.0579 | 2.6412 | 0.0115 | 0.0272 |
| 4.0011 | −0.3604 | 2.6313 | 0.0140 | 0.0269 | 1.5670 | 0.0932 | 2.6570 | 0.0071 | 0.0277 |
| 6.7076 | 0.4947 | 2.6647 | 0.0001 | 0.0266 | 0.3312 | 0.6677 | 2.6432 | 0.0047 | 0.0267 |
| 3.8433 | −0.4412 | 2.6527 | −0.0038 | 0.0267 | 1.5154 | 0.4973 | 2.6377 | 0.0112 | 0.0269 |
| 1.6209 | 1.3167 | 2.6587 | −0.0049 | 0.0270 | 1.3781 | 0.5339 | 2.6637 | 0.0154 | 0.0270 |
| 6.4491 | 0.0079 | 2.6328 | 0.0109 | 0.0295 | 3.0018 | 0.2049 | 2.6403 | 0.0053 | 0.0307 |
| 4.1060 | 0.9849 | 2.6575 | 0.0114 | 0.0276 | 0.9180 | 0.1477 | 2.6433 | 0.0111 | 0.0289 |
| 2.1733 | 1.8947 | 2.6559 | 0.0090 | 0.0265 | 5.1066 | −0.3883 | 2.6571 | 0.0036 | 0.0292 |
| 3.9780 | 1.3259 | 2.6587 | 0.0045 | 0.0253 | 2.6395 | 0.1034 | 2.6476 | 0.0000 | 0.0291 |
| 1.5406 | 0.9525 | 2.6446 | 0.0129 | 0.0263 | 0.6622 | 0.3279 | 2.6516 | 0.0083 | 0.0281 |
| 2.1788 | 0.4048 | 2.6615 | 0.0236 | 0.0261 | −0.1468 | 1.1264 | 2.6465 | 0.0151 | 0.0275 |
| 1.9404 | 0.0099 | 2.6283 | 0.0130 | 0.0271 | −0.0247 | 0.6362 | 2.6432 | 0.0015 | 0.0278 |
| 1.9549 | 0.4762 | 2.6221 | 0.0232 | 0.0295 | 1.7889 | 0.5632 | 2.6547 | 0.0071 | 0.0268 |
| 2.9398 | 0.9709 | 2.6359 | 0.0173 | 0.0277 | 0.5866 | 0.7823 | 2.6288 | 0.0100 | 0.0260 |
| 4.6992 | 0.8857 | 2.6581 | 0.0099 | 0.0276 | 0.9661 | 0.2051 | 2.6400 | 0.0117 | 0.0263 |
| 3.8413 | 1.2933 | 2.6491 | 0.0102 | 0.0279 | 4.8918 | −0.3495 | 2.6747 | 0.0099 | 0.0267 |
| 0.6524 | 0.5740 | 2.6492 | 0.0294 | 0.0280 | −1.0871 | 0.4289 | 2.6558 | 0.0135 | 0.0268 |
| 1.6230 | −0.5131 | 2.6233 | 0.0344 | 0.0285 | −0.3821 | 0.8696 | 2.6542 | 0.0153 | 0.0279 |
| 2.9979 | 0.6722 | 2.6589 | 0.0268 | 0.0295 | 1.6874 | 1.1765 | 2.6550 | 0.0132 | 0.0263 |
| 1.9096 | −0.2110 | 2.6480 | 0.0175 | 0.0291 | −2.1858 | 0.7562 | 2.6636 | 0.0090 | 0.0277 |
| 2.2477 | −0.0590 | 2.6504 | 0.0276 | 0.0288 | −2.6296 | 1.8506 | 2.6530 | 0.0141 | 0.0275 |
| 2.3825 | −0.5209 | 2.6227 | 0.0105 | 0.0273 | 3.7543 | −0.5411 | 2.6457 | 0.0121 | 0.0272 |
| 5.4062 | 0.6180 | 2.6520 | 0.0206 | 0.0294 | 3.5189 | 0.2600 | 2.6576 | 0.0053 | 0.0285 |
| 3.2851 | −1.2934 | 2.6382 | 0.0243 | 0.0301 | 4.2585 | 0.3335 | 2.6607 | 0.0087 | 0.0284 |
| 4.5516 | −1.0107 | 2.6595 | 0.0112 | 0.0291 | 6.4991 | −0.4479 | 2.6693 | −0.0018 | 0.0286 |
| 5.8935 | 0.0545 | 2.6474 | 0.0139 | 0.0287 | 3.1058 | −0.3772 | 2.6617 | 0.0055 | 0.0280 |
| 2.5191 | −0.9520 | 2.6533 | 0.0164 | 0.0296 | 4.8242 | −0.9876 | 2.6703 | 0.0025 | 0.0290 |
| 5.1104 | −0.4067 | 2.6471 | 0.0170 | 0.0282 | 5.9664 | −0.1147 | 2.1495 | 0.0045 | 0.0305 |
| 2.1961 | −0.4469 | 2.6241 | 0.0229 | 0.0297 | 1.0601 | 0.5997 | 2.6455 | 0.0084 | 0.0302 |
| 2.9077 | 0.0325 | 2.6495 | 0.0267 | 0.0280 | 3.4894 | 0.5805 | 2.6678 | 0.0032 | 0.0305 |
| 1.4894 | −0.0662 | 2.6326 | 0.0250 | 0.0289 | −1.6138 | 0.4367 | 2.6486 | 0.0101 | 0.0293 |
| 0.6220 | 0.7207 | 2.6556 | 0.0095 | 0.0291 | −0.5115 | 1.2861 | 2.6422 | 0.0079 | 0.0207 |
| 2.5373 | −0.5680 | 2.6398 | 0.0147 | 0.0285 | 0.7145 | 1.4908 | 2.6305 | 0.0072 | 0.0300 |
| 6.0188 | 0.0886 | 2.6532 | 0.0095 | 0.0280 | 3.9725 | 1.2765 | 2.6562 | 0.0091 | 0.0293 |
| 7.2506 | −0.2126 | 2.6417 | 0.0194 | 0.0279 | 5.4249 | −0.0816 | 2.6611 | 0.0114 | 0.0296 |
| 4.5667 | 1.7860 | 2.6374 | 0.0161 | 0.0290 | 3.2026 | −0.5673 | 2.6429 | 0.0200 | 0.0286 |
| 3.0172 | 0.1696 | 2.6497 | 0.0176 | 0.0274 | 2.0455 | 1.2745 | 2.6466 | 0.0145 | 0.0286 |
| 3.9111 | 1.1394 | 2.6477 | 0.0201 | 0.0293 | 2.4188 | 0.9620 | 2.6737 | −0.0002 | 0.0273 |
| 5.2551 | 1.5293 | 2.6447 | 0.0054 | 0.0295 | 3.3449 | −0.1141 | 2.6555 | 0.0067 | 0.0259 |
| 2.1325 | 0.4410 | 2.6588 | −0.0024 | 0.0287 | 4.3214 | −0.0793 | 2.6440 | 0.0160 | 0.0270 |
| 2.8354 | 1.5409 | 2.6727 | −0.0064 | 0.0288 | 2.7713 | −0.7040 | 2.6426 | 0.0079 | 0.0267 |
| 4.5979 | 0.6276 | 2.6510 | −0.0062 | 0.0282 | 0.9444 | 0.4459 | 2.6674 | 0.0153 | 0.0273 |
| 3.7213 | −0.1407 | 2.6586 | −0.0040 | 0.0274 | −0.0702 | 0.1260 | 2.6674 | 0.0110 | 0.0272 |
| 3.6221 | −0.4802 | 2.6571 | −0.0002 | 0.0279 | 0.9428 | −0.1744 | 2.6575 | 0.0133 | 0.0277 |
| 5.3641 | −0.9105 | 2.6667 | 0.0057 | 0.0286 | −0.1427 | 0.6357 | 2.6534 | 0.0190 | 0.0275 |
| 3.2189 | −0.1153 | 2.6427 | 0.0096 | 0.0299 | 0.8759 | −0.8342 | 2.6414 | 0.0150 | 0.0261 |
| 4.2735 | −0.7222 | 2.6465 | 0.0117 | 0.0205 | 1.9744 | 0.5733 | 2.6486 | 0.0100 | 0.0254 |
| 1.9177 | −0.5780 | 2.6568 | 0.0104 | 0.0288 | −0.3617 | 0.0682 | 2.6633 | 0.0020 | 0.0264 |
| 3.7664 | −0.5552 | 2.6418 | 0.0250 | 0.0282 | 1.7066 | 0.6479 | 2.6413 | 0.0091 | 0.0255 |
| 4.4524 | −0.1917 | 2.6546 | 0.0171 | 0.0270 | 1.1759 | 0.7844 | 2.6420 | 0.0204 | 0.0257 |
| 4.4813 | −0.5660 | 2.6697 | 0.0097 | 0.0275 | 2.4663 | −0.4456 | 2.6230 | 0.0119 | 0.0267 |
| 4.0185 | −0.5000 | 2.6584 | 0.0148 | 0.0268 | 3.7861 | 0.8542 | 2.6466 | 0.0061 | 0.0281 |
| 2.9151 | −0.6604 | 2.6482 | 0.0165 | 0.0280 | 4.5801 | −0.3225 | 2.6306 | 0.0053 | 0.0283 |
| 3.5152 | 1.8551 | 2.6349 | 0.0132 | 0.0282 | 0.6237 | 0.0838 | 2.6622 | 0.0098 | 0.0262 |
| 5.3728 | 0.2079 | 2.6492 | 0.0161 | 0.0280 | 2.3230 | −0.1853 | 2.6611 | 0.0057 | 0.0269 |
| 4.1296 | 0.7023 | 2.6557 | 0.0236 | 0.0274 | −0.1523 | 0.5918 | 2.6486 | 0.0133 | 0.0271 |
| 1.5990 | 1.2981 | 2.6521 | 0.0247 | 0.0288 | 0.9998 | −0.3891 | 2.6457 | 0.0100 | 0.0260 |
| 0.4781 | 0.4151 | 2.6531 | 0.0249 | 0.0280 | 3.8535 | −0.2113 | 2.6435 | 0.0158 | 0.0269 |
| 3.4751 | 1.5312 | 2.6590 | 0.0158 | 0.0201 | 2.4046 | 0.2231 | 2.6675 | 0.0095 | 0.0268 |
| 2.9099 | 1.9314 | 2.6745 | 0.0117 | 0.0283 | 3.4737 | −0.0573 | 2.6551 | 0.0146 | 0.0252 |
| 2.8016 | 0.1320 | 2.6374 | 0.0238 | 0.0271 | 1.5853 | 0.6534 | 2.6447 | 0.0088 | 0.0269 |
| 4.6220 | 0.1202 | 2.6498 | 0.0119 | 0.0265 | 1.0597 | 0.6710 | 2.6534 | 0.0100 | 0.0282 |
| 2.9798 | −0.4553 | 2.6474 | 0.0079 | 0.0273 | 3.2592 | 0.8020 | 2.6667 | 0.0158 | 0.0284 |
| 1.8883 | 0.1973 | 2.6459 | 0.0100 | 0.0274 | 3.4381 | −0.7192 | 2.6499 | 0.0178 | 0.0276 |
| 2.8240 | 0.9165 | 2.6527 | 0.0111 | 0.0272 | 1.0524 | 1.1456 | 2.6410 | 0.0379 | 0.0281 |
| 3.3219 | 0.3573 | 2.6707 | 0.0126 | 0.0270 | 3.1439 | 1.3877 | 2.6401 | 0.0210 | 0.0284 |
| 1.5746 | −0.2252 | 2.6516 | 0.0158 | 0.0267 | 2.6103 | 0.5433 | 2.6599 | 0.0178 | 0.0280 |

TABLE 2-continued

| | | | | | | | | | |
|---|---|---|---|---|---|---|---|---|---|
| −0.1013 | −0.2693 | 2.6331 | 0.0082 | 0.0256 | 0.7634 | −0.2882 | 2.6524 | 0.0155 | 0.0285 |
| 1.2971 | 0.6400 | 2.6450 | 0.0100 | 0.0260 | 5.7338 | 0.1642 | 2.6432 | 0.0120 | 0.0280 |
| 0.3191 | 1.3843 | 2.6353 | 0.0114 | 0.0291 | 1.2806 | −1.4453 | 2.6367 | 0.0135 | 0.0305 |
| 1.6723 | 0.6906 | 2.6447 | 0.0094 | 0.0292 | 3.9127 | 0.3174 | 2.6348 | 0.0205 | 0.0296 |
| −1.0777 | −0.4901 | 2.6449 | 0.0107 | 0.0303 | 4.8539 | 0.4825 | 2.6556 | 0.0244 | 0.0282 |
| −3.9291 | 0.5887 | 2.6684 | 0.0102 | 0.0285 | 3.8951 | −0.6716 | 2.6331 | 0.0290 | 0.0275 |
| 3.1698 | −0.9033 | 2.6637 | 0.0055 | 0.0278 | 3.7949 | −0.5472 | 2.6350 | 0.0226 | 0.0264 |
| 4.1814 | 0.4482 | 2.6610 | 0.0068 | 0.0294 | 4.1283 | −0.1432 | 2.6522 | 0.0194 | 0.0256 |
| 0.7354 | 0.5277 | 2.6647 | 0.0005 | 0.0278 | 2.7782 | 0.8330 | 2.6547 | 0.0195 | 0.0259 |
| 1.5022 | 0.5845 | 2.6555 | 0.0049 | 0.0291 | 2.7961 | 1.5846 | 2.6524 | 0.0105 | 0.0268 |
| 0.1747 | 0.8303 | 2.6671 | 0.0039 | 0.0289 | 4.1492 | 0.4320 | 2.6569 | 0.0070 | 0.0288 |
| 1.7663 | −0.3543 | 2.6516 | 0.0137 | 0.0279 | 1.5853 | −0.0143 | 2.6438 | 0.0054 | 0.0267 |
| 3.2598 | 0.3567 | 2.6312 | 0.0161 | 0.0293 | 3.5404 | 0.0249 | 2.6390 | 0.0030 | 0.0270 |
| 3.8279 | 0.0411 | 2.6401 | 0.0109 | 0.0289 | 2.1008 | 0.1933 | 2.6417 | 0.0149 | 0.0297 |
| 2.1005 | −0.0471 | 2.6496 | 0.0076 | 0.0288 | 3.5209 | 0.2009 | 2.6532 | 0.0136 | 0.0299 |
| 1.9924 | 0.5669 | 2.6461 | 0.0105 | 0.0290 | 2.1517 | 0.3993 | 2.6496 | 0.0111 | 0.0289 |
| 0.1109 | −0.3341 | 2.6477 | 0.0110 | 0.0286 | 2.8376 | 0.6066 | 2.6439 | 0.0089 | 0.0280 |
| 0.4289 | 0.1274 | 2.6616 | 0.0162 | 0.0301 | 4.9278 | 1.0406 | 2.6629 | 0.0037 | 0.0276 |
| 2.4044 | −0.0547 | 2.6493 | 0.0069 | 0.0294 | 1.0414 | 0.3193 | 2.6315 | 0.0115 | 0.0267 |
| 2.5409 | −0.4540 | 2.6388 | 0.0124 | 0.0292 | 2.5122 | −0.2957 | 2.6324 | 0.0094 | 0.0271 |
| 2.8323 | 0.0917 | 2.6474 | 0.0045 | 0.0282 | 2.5141 | 0.5100 | 2.6474 | −0.0031 | 0.0275 |
| 4.2888 | −1.0347 | 2.6476 | 0.0110 | 0.0287 | 3.3576 | 0.3773 | 2.6411 | 0.0029 | 0.0298 |
| 6.1028 | 0.0240 | 2.6362 | 0.0075 | 0.0283 | 4.9494 | 0.4993 | 2.6557 | 0.0024 | 0.0299 |
| 3.8667 | 0.0410 | 2.6496 | 0.0064 | 0.0288 | 1.8925 | −0.1692 | 2.6501 | 0.0116 | 0.0298 |
| 3.0977 | 0.7536 | 2.6560 | 0.0003 | 0.0280 | 2.7189 | 0.4081 | 2.6547 | 0.0134 | 0.0306 |
| 3.8780 | 0.4261 | 2.6433 | 0.0109 | 0.0270 | 1.4020 | −0.2088 | 2.6499 | 0.0119 | 0.0304 |
| 2.9133 | −0.5165 | 2.6393 | 0.0000 | 0.0297 | −0.0538 | −0.1441 | 2.6435 | 0.0110 | 0.0312 |
| −0.0911 | −0.1187 | 2.6596 | 0.0027 | 0.0300 | −0.8963 | 0.5918 | 2.6530 | 0.0208 | 0.0299 |
| 0.6107 | 0.9822 | 2.6700 | 0.0097 | 0.0283 | 2.5659 | 0.5307 | 2.6420 | 0.0162 | 0.0300 |
| 2.6790 | 1.2073 | 2.6627 | 0.0067 | 0.0272 | 1.8333 | 0.8272 | 2.6608 | 0.0041 | 0.0282 |
| −0.1156 | 1.3299 | 2.6492 | 0.0057 | 0.0263 | 2.7699 | 0.9731 | 2.6597 | −0.0030 | 0.0281 |
| 1.6220 | 0.3204 | 2.6622 | −0.0071 | 0.0272 | 3.2818 | 0.3193 | 2.6415 | 0.0074 | 0.0277 |
| 0.2752 | 1.0149 | 2.6339 | −0.0074 | 0.0283 | 1.8543 | 0.7124 | 2.6398 | 0.0095 | 0.0267 |
| 3.2701 | 0.2997 | 2.6651 | −0.0185 | 0.0290 | 1.5228 | −0.0338 | 2.6310 | 0.0225 | 0.0270 |
| 1.6401 | 0.8781 | 2.6409 | −0.0063 | 0.0278 | 2.6691 | −0.3775 | 2.6517 | 0.0216 | 0.0266 |
| 1.1425 | 1.2459 | 2.6266 | 0.0060 | 0.0284 | 3.4645 | −0.2822 | 2.6460 | 0.0244 | 0.0266 |
| 1.0338 | 1.4907 | 2.6520 | 0.0130 | 0.0274 | 4.4304 | 0.3474 | 2.6474 | 0.0225 | 0.0267 |
| 1.4116 | 1.7192 | 2.6528 | 0.0084 | 0.0263 | 2.2574 | 1.2972 | 2.6428 | 0.0175 | 0.0295 |
| 1.2370 | 1.2381 | 2.6368 | 0.0110 | 0.0259 | 2.1549 | −0.2944 | 2.6601 | 0.0214 | 0.0302 |
| 3.1371 | 0.3696 | 2.6395 | 0.0041 | 0.0264 | 3.6838 | −0.3037 | 2.6722 | 0.0154 | 0.0287 |
| 3.6616 | 0.5363 | 2.6498 | 0.0127 | 0.0253 | 1.9460 | 0.6013 | 2.6773 | 0.0118 | 0.0295 |
| 3.2428 | 0.0226 | 2.6381 | 0.0131 | 0.0249 | 1.5834 | 0.4680 | 2.6543 | 0.0063 | 0.0299 |
| 1.4966 | 0.8059 | 2.6598 | 0.0071 | 0.0267 | 2.4040 | −0.1473 | 2.6630 | 0.0042 | 0.0309 |
| 3.3710 | 0.1274 | 2.6446 | 0.0031 | 0.0259 | 2.4609 | −0.0096 | 2.6593 | 0.0013 | 0.0314 |
| 2.2512 | 1.2683 | 2.6330 | 0.0058 | 0.0263 | 1.2939 | 0.5399 | 2.6563 | −0.0020 | 0.0291 |
| 2.0922 | −1.2040 | 2.6365 | 0.0015 | 0.0257 | 0.2950 | 1.3836 | 2.6611 | 0.0085 | 0.0294 |
| 0.5129 | 1.2030 | 2.6625 | 0.0057 | 0.0283 | 0.4828 | −0.4701 | 2.6594 | 0.0100 | 0.0281 |
| 0.6839 | 0.2860 | 2.6772 | 0.0000 | 0.0282 | −0.9117 | 0.7955 | 2.6495 | 0.0074 | 0.0298 |
| 3.8595 | 0.7497 | 2.6423 | 0.0029 | 0.0275 | 2.6197 | 0.2072 | 2.6263 | 0.0141 | 0.0283 |
| 1.3922 | −1.0101 | 2.6687 | 0.0025 | 0.0275 | 2.3680 | 0.5693 | 2.6519 | 0.0225 | 0.0274 |
| 0.5921 | −0.2253 | 2.6437 | 0.0025 | 0.0280 | 5.2723 | −0.1830 | 2.6533 | 0.0122 | 0.0285 |
| 2.6396 | −0.6700 | 2.6697 | 0.0092 | 0.0271 | 2.7228 | 0.4345 | 2.6373 | 0.0168 | 0.0302 |
| 2.6209 | 0.3472 | 2.6499 | 0.0137 | 0.0283 | 3.7672 | 2.6780 | 2.6494 | 0.0154 | 0.0310 |
| 4.6424 | −0.5596 | 2.6508 | 0.0112 | 0.0295 | 0.8158 | 1.5049 | 2.6537 | 0.0134 | 0.0304 |
| 2.8564 | −0.9806 | 2.6726 | 0.0081 | 0.0277 | 2.8557 | 0.4694 | 2.6581 | 0.0111 | 0.0300 |
| 1.9971 | −0.2777 | 2.6572 | 0.0115 | 0.0291 | 3.3125 | 0.7627 | 2.6312 | 0.0081 | 0.0287 |
| 2.4162 | 0.0060 | 2.6575 | 0.0054 | 0.0275 | 2.1653 | 0.3396 | 2.6251 | 0.0145 | 0.0271 |
| 1.7996 | 0.2835 | 2.6738 | 0.0091 | 0.0267 | 4.0440 | −0.1704 | 2.6486 | 0.0093 | 0.0282 |
| 3.6385 | −0.6738 | 2.6611 | 0.0084 | 0.0282 | 3.1525 | 1.7506 | 2.6495 | 0.0062 | 0.0296 |
| 4.7833 | 0.1569 | 2.6577 | 0.0125 | 0.0285 | 2.6372 | 0.9261 | 2.6321 | 0.0137 | 0.0273 |
| 2.4901 | 0.3596 | 3.6559 | 0.0067 | 0.0279 | 3.8692 | 0.3528 | 2.6401 | 0.0107 | 0.0264 |
| 2.2168 | 0.2011 | 2.6372 | 0.0164 | 0.0287 | 0.4961 | 0.2141 | 2.6398 | 0.0145 | 0.0271 |
| 4.4380 | −0.5967 | 2.6624 | 0.0048 | 0.0306 | −2.0289 | 0.5504 | 2.6653 | 0.0086 | 0.0282 |
| 3.3658 | −1.0464 | 2.6435 | 0.0038 | 0.0311 | 0.3985 | 1.6094 | 2.6754 | 0.0117 | 0.0283 |
| 3.0643 | −0.4288 | 2.6456 | 0.0061 | 0.0309 | 2.7526 | 2.2494 | 2.6572 | 0.0092 | 0.0274 |
| 3.5938 | 0.5403 | 2.6347 | 0.0002 | 0.0304 | 0.8530 | 2.9245 | 2.6513 | 0.0096 | 0.0278 |
| 2.4859 | −0.4920 | 2.6633 | 0.0165 | 0.0274 | 1.6767 | 1.9616 | 2.6511 | 0.0235 | 0.0248 |
| 1.5234 | −0.4379 | 2.6661 | 0.0258 | 0.0277 | 1.3075 | 2.2255 | 2.6732 | 0.0202 | 0.0241 |
| 3.8672 | −0.0981 | 2.6523 | 0.0206 | 0.0273 | 2.0693 | 1.8574 | 2.6412 | 0.0187 | 0.0253 |
| 4.0436 | 0.5305 | 2.6686 | 0.0218 | 0.0296 | 1.0395 | 2.0545 | 2.6487 | 0.0156 | 0.0249 |
| 0.9796 | 0.6253 | 2.6591 | 0.0049 | 0.0297 | 2.4440 | 0.3822 | 2.6512 | 0.0160 | 0.0253 |
| −0.5808 | 1.1265 | 2.6465 | 0.0034 | 0.0286 | 2.0225 | 0.3172 | 2.6528 | 0.0088 | 0.0260 |
| 1.5748 | 0.8738 | 2.6514 | 0.0039 | 0.0278 | 1.9715 | 0.0421 | 2.6360 | 0.0161 | 0.0255 |
| 4.0370 | −0.7495 | 2.6529 | 0.0086 | 0.0271 | 2.5746 | −0.0536 | 2.6686 | 0.0071 | 0.0258 |
| 0.6101 | 0.2988 | 2.6368 | 0.0047 | 0.0255 | −0.6930 | 0.9567 | 2.6559 | −0.0057 | 0.0262 |
| 2.8700 | −0.1349 | 2.6603 | 0.0085 | 0.0256 | 1.4628 | −0.3478 | 2.6501 | 0.0076 | 0.0270 |
| −0.4733 | −0.0489 | 2.6587 | 0.0102 | 0.0261 | 1.0105 | −0.0304 | 2.6684 | 0.0161 | 0.0269 |
| 0.7370 | 0.9188 | 2.6538 | 0.0092 | 0.0254 | −3.2263 | 1.7481 | 2.6435 | 0.0063 | 0.0268 |
| 2.9300 | 0.3353 | 2.6462 | 0.0123 | 0.0256 | 1.9017 | 0.7542 | 2.6517 | 0.0098 | 0.0286 |

TABLE 2-continued

| | | | | | | | | | |
|---|---|---|---|---|---|---|---|---|---|
| 2.0886 | 1.3236 | 2.6357 | 0.0084 | 0.0265 | 4.0304 | 0.1766 | 2.6383 | 0.0132 | 0.0287 |
| 2.1879 | −0.7745 | 2.6446 | 0.0131 | 0.0277 | 2.4128 | 0.1159 | 2.6529 | 0.0164 | 0.0288 |
| 4.1685 | −0.6752 | 2.6428 | 0.0037 | 0.0277 | 0.0305 | −0.0196 | 2.6599 | 0.0181 | 0.0280 |
| 2.0410 | −0.3573 | 2.6473 | 0.0101 | 0.0285 | 3.2232 | −0.9333 | 2.6418 | 0.0167 | 0.0290 |
| −0.6869 | −0.0661 | 2.6559 | 0.0097 | 0.0279 | 1.1432 | 0.1834 | 2.6454 | 0.0072 | 0.0281 |
| 0.7397 | −0.4398 | 2.6338 | 0.0154 | 0.0260 | 2.2215 | −0.1014 | 2.6425 | 0.0104 | 0.0289 |
| 3.6310 | 0.1990 | 2.6586 | 0.0114 | 0.0263 | −0.2825 | 0.1978 | 2.6392 | 0.0148 | 0.0279 |
| 1.9068 | −0.2643 | 2.6450 | 0.0150 | 0.0274 | 3.0083 | 1.2311 | 2.6516 | 0.0137 | 0.0277 |
| 2.2251 | −0.8130 | 2.6657 | 0.0225 | 0.0288 | 4.3219 | 1.9201 | 2.6487 | 0.0107 | 0.0282 |
| 4.5440 | −0.7951 | 2.6656 | 0.0236 | 0.0290 | 3.1885 | 0.4025 | 2.6428 | 0.0144 | 0.0285 |
| 3.6395 | 0.0707 | 2.6593 | 0.0215 | 0.0283 | 2.2906 | 0.6217 | 2.6499 | 0.0147 | 0.0275 |
| 3.1062 | −0.1092 | 2.6534 | 0.0256 | 0.0291 | 1.6757 | 2.2050 | 2.6363 | 0.0159 | 0.0274 |
| 5.8110 | 1.1381 | 2.6480 | 0.0235 | 0.0274 | 0.8952 | 1.4799 | 2.6554 | 0.0043 | 0.0286 |
| 4.6908 | −0.5021 | 2.6532 | 0.0198 | 0.0278 | 2.5448 | −0.2973 | 2.6300 | 0.0210 | 0.0285 |
| 3.3988 | −1.0302 | 2.6438 | 0.0205 | 0.0277 | −0.2174 | 0.0775 | 2.6680 | 0.0275 | 0.0286 |
| 2.1869 | −0.3422 | 2.6431 | 0.0193 | 0.0267 | 0.2083 | 0.4909 | 2.6408 | 0.0320 | 0.0293 |
| 2.4650 | −0.0120 | 2.6280 | 0.0228 | 0.0268 | 2.8221 | 1.2709 | 2.6459 | 0.0317 | 0.0282 |
| 1.9170 | 1.0726 | 2.6483 | 0.0201 | 0.0252 | 2.6995 | 2.1093 | 2.6641 | 0.0205 | 0.0283 |
| 2.7506 | 1.1504 | 2.6275 | 0.0244 | 0.0257 | 2.3638 | 0.7217 | 2.6688 | 0.0101 | 0.0282 |
| 3.0049 | 0.6225 | 2.6525 | 0.0141 | 0.0270 | −1.3189 | 0.0573 | 2.6343 | 0.0140 | 0.0282 |
| 0.5434 | 2.3585 | 2.6478 | 0.0048 | 0.0266 | −0.6446 | 1.7212 | 2.6509 | 0.0045 | 0.0285 |
| 1.9139 | 0.1617 | 2.6423 | 0.0004 | 0.0282 | −3.4074 | 1.2886 | 2.6476 | 0.0058 | 0.0267 |
| 0.8917 | 0.6350 | 2.6599 | 0.0047 | 0.0282 | −1.1605 | 1.1116 | 2.6598 | −0.0004 | 0.0285 |
| 2.5632 | 0.4094 | 2.6625 | 0.0022 | 0.0278 | 2.0567 | 0.8284 | 2.6497 | 0.0098 | 0.0284 |
| 2.5362 | 0.6529 | 3.6759 | 0.0108 | 0.0275 | 4.7300 | −0.4794 | 2.6370 | 0.0110 | 0.0280 |
| 1.7303 | −0.0473 | 2.6527 | 0.0157 | 0.0280 | 2.2970 | −0.0991 | 2.6521 | 0.0149 | 0.0270 |
| 1.9303 | −0.0363 | 2.6395 | 0.0177 | 0.0286 | 3.4457 | −1.0124 | 2.6544 | 0.0210 | 0.0275 |
| 1.0476 | −1.1605 | 2.6387 | 0.0152 | 0.0283 | 1.5088 | −0.6729 | 2.6433 | 0.0082 | 0.0280 |
| 1.2120 | 1.0038 | 2.6646 | 0.0138 | 0.0278 | 1.6876 | −0.9120 | 2.6438 | 0.0075 | 0.0279 |
| −0.9859 | 0.7097 | 2.6552 | 0.0107 | 0.0298 | 2.5889 | 0.0662 | 2.6504 | 0.0088 | 0.0276 |
| 2.0854 | 0.7761 | 2.6404 | 0.0101 | 0.0288 | 1.5850 | 0.2148 | 2.6511 | 0.0166 | 0.0278 |
| −0.6495 | 1.2349 | 2.6366 | 0.0089 | 0.0290 | 0.0334 | 0.3286 | 2.6512 | 0.0046 | 0.0278 |
| 0.9019 | −0.0660 | 2.6482 | 0.0116 | 0.0297 | 1.2341 | 1.4716 | 2.6544 | 0.0102 | 0.0269 |
| 5.1570 | −0.0790 | 2.6551 | 0.0093 | 0.0288 | 2.5901 | 0.6790 | 2.6403 | 0.0153 | 0.0273 |
| 2.6019 | 0.5844 | 2.6532 | 0.0087 | 0.0284 | 4.1424 | 0.7296 | 2.6512 | 0.0194 | 0.0274 |
| 1.3537 | 0.3319 | 2.6628 | 0.0120 | 0.0285 | 1.0951 | 0.6219 | 2.6605 | 0.0161 | 0.0281 |
| 0.0301 | 1.6327 | 2.6433 | −0.0022 | 0.0265 | −0.4229 | 0.8707 | 2.6476 | 0.0097 | 0.0275 |
| 4.4572 | 2.8726 | 2.6463 | 0.0059 | 0.0268 | −0.5343 | 0.8659 | 2.6426 | 0.0043 | 0.0279 |
| 1.6601 | 1.2821 | 2.6494 | −0.0022 | 0.0274 | 2.4644 | 0.9262 | 2.6495 | −0.0003 | 0.0278 |
| −0.6070 | 0.2824 | 2.6562 | 0.0051 | 0.0283 | 2.3716 | 0.8363 | 2.6817 | 0.0010 | 0.0279 |
| 0.9233 | 0.0054 | 2.6434 | 0.0125 | 0.0285 | 0.5293 | −0.4723 | 2.6486 | 0.0047 | 0.0276 |
| 1.6990 | −0.2754 | 2.6555 | 0.0106 | 0.0288 | 1.1403 | −0.3955 | 2.6565 | 0.0061 | 0.0373 |
| 0.9473 | 1.1233 | 2.6369 | 0.0090 | 0.0291 | 0.2209 | 0.9781 | 2.6658 | 0.0093 | 0.0275 |
| 2.1586 | 1.1393 | 2.6536 | 0.0198 | 0.0280 | 2.1736 | −0.0985 | 2.6635 | 0.0026 | 0.0277 |
| 3.3017 | 0.4679 | 2.6401 | 0.0130 | 0.0272 | 2.6073 | −0.2020 | 2.6497 | 0.0048 | 0.0298 |
| 3.3170 | 1.2340 | 2.6372 | 0.0037 | 0.0281 | 2.0440 | 0.0734 | 2.6529 | 0.0082 | 0.0283 |
| 5.1318 | 1.0244 | 2.6369 | 0.0050 | 0.0279 | 1.3921 | −0.9175 | 1.6449 | 0.0092 | 0.0283 |
| −2.1840 | 0.1555 | 2.6394 | 0.0076 | 0.0284 | 2.8801 | −0.0183 | 2.6668 | 0.0141 | 0.0289 |
| 1.4641 | 0.1219 | 2.6534 | 0.0210 | 0.0298 | 1.8914 | −0.3138 | 2.6502 | 0.0149 | 0.0288 |
| 1.8987 | −0.2571 | 2.6623 | 0.0104 | 0.0305 | 1.5328 | 0.0073 | 2.6422 | 0.0159 | 0.0292 |
| 1.2267 | 0.3674 | 2.6374 | 0.0098 | 0.0301 | 2.2038 | 0.6103 | 2.6415 | 0.0166 | 0.0275 |
| 4.5438 | −0.5718 | 2.6563 | 0.0079 | 0.0274 | 0.1819 | 0.1265 | 2.6442 | 0.0122 | 0.0266 |
| 3.9378 | −0.0941 | 2.6522 | 0.0116 | 0.0289 | 2.5810 | 0.4495 | 2.6455 | 0.0159 | 0.0264 |
| 3.8107 | 0.4374 | 2.6447 | 0.0133 | 0.0265 | 4.9803 | 0.1533 | 2.6577 | 0.0088 | 0.0281 |
| 0.9219 | 1.0296 | 2.6593 | 0.0023 | 0.0267 | 1.9600 | −0.1685 | 2.6546 | 0.0094 | 0.0271 |
| −0.7946 | −0.1208 | 2.6684 | 0.0183 | 0.0259 | 4.3646 | 0.4360 | 2.6572 | 0.0151 | 0.0277 |
| 0.6349 | 0.7902 | 2.6466 | 0.0139 | 0.0262 | 5.2818 | −0.4535 | 2.6343 | 0.0140 | 0.0278 |
| 0.2548 | 0.6140 | 2.6594 | 0.0152 | 0.0254 | 5.3174 | −0.1191 | 2.6347 | 0.0096 | 0.0276 |
| 1.5266 | −0.0736 | 2.6209 | 0.9200 | 0.0259 | 3.3036 | −0.1611 | 2.6650 | 0.0040 | 0.0275 |
| 0.9587 | 0.5604 | 2.6546 | 0.0160 | 0.0261 | 1.5648 | −9.0127 | 2.6613 | 0.0024 | 0.0260 |
| 0.5502 | −0.0683 | 2.6519 | 0.0193 | 0.0280 | 3.0502 | −0.0797 | 2.6643 | 0.0045 | 0.0257 |
| −0.0524 | 0.4337 | 2.6446 | 0.0241 | 0.0282 | 0.0012 | 0.2290 | 2.6425 | 0.0105 | 0.0273 |
| 3.4571 | 0.6155 | 2.6454 | 0.0165 | 0.0276 | 0.4493 | 1.1653 | 2.6542 | 0.0065 | 0.0273 |
| 3.5822 | 1.0265 | 2.6705 | 0.0213 | 0.0272 | 2.3258 | −0.0671 | 2.6437 | 0.0065 | 0.0268 |
| −0.1879 | −0.5071 | 2.6524 | 0.0124 | 0.0261 | −0.6535 | 0.3324 | 2.6467 | 0.0069 | 0.0262 |
| 4.1596 | 0.4234 | 2.6602 | 0.0104 | 0.0265 | 1.6022 | 0.4215 | 2.6606 | 0.0018 | 0.0258 |
| 3.9447 | 0.5440 | 2.6517 | 0.0107 | 0.0276 | 5.4338 | −0.3640 | 2.6601 | −0.0052 | 0.0262 |
| 5.9727 | 0.0270 | 2.6431 | 0.0096 | 0.0281 | 3.0069 | −0.0380 | 2.6609 | −0.0004 | 0.0257 |
| 3.9769 | −0.6364 | 2.6692 | 0.0100 | 0.0267 | 4.6487 | −0.7413 | 2.6461 | −0.0082 | 0.0261 |
| 2.5700 | −0.1099 | 2.6669 | 0.0073 | 0.0265 | 2.3456 | 1.4983 | 2.6747 | −0.0128 | 0.0261 |
| 2.6408 | −0.0658 | 2.6480 | 0.0047 | 0.0262 | 0.9232 | 0.6104 | 2.6761 | −0.0015 | 0.0260 |
| 5.1297 | −0.2224 | 2.6402 | 0.0108 | 0.0277 | 3.6172 | −0.5355 | 2.6573 | 0.0134 | 0.0260 |
| 4.4384 | −0.3064 | 2.6710 | 0.0086 | 0.0269 | 3.0536 | 0.0784 | 2.6518 | 0.0162 | 0.0256 |
| 0.6683 | 0.0891 | 2.6660 | 0.0067 | 0.0280 | 2.0485 | −0.0320 | 2.6570 | 0.0220 | 0.0260 |
| 1.1178 | 0.5595 | 2.6713 | 0.0025 | 0.0271 | 0.7658 | 0.6243 | 2.6659 | 0.0206 | 0.0278 |
| 2.8530 | 0.1346 | 2.6392 | 0.0125 | 0.0268 | 2.1972 | 0.3205 | 2.6600 | 0.0195 | 0.0286 |
| 2.3643 | 0.9962 | 2.6663 | 0.0102 | 0.0268 | 4.3132 | 0.2104 | 2.6628 | 0.0035 | 0.0281 |
| 2.9706 | 1.0720 | 2.6506 | 0.9107 | 0.0262 | 3.7862 | 0.8854 | 2.6579 | 0.0044 | 0.0257 |
| 2.3584 | 1.3715 | 2.6710 | 0.0062 | 0.0265 | 0.8642 | −0.1307 | 2.6658 | 0.0130 | 0.0260 |

TABLE 2-continued

| | | | | | | | | | |
|---|---|---|---|---|---|---|---|---|---|
| 3.0730 | 0.2261 | 2.6625 | −0.0055 | 0.0271 | 2.4608 | −0.3940 | 2.6529 | 0.0223 | 0.0253 |
| 2.8465 | 0.9877 | 2.6729 | 0.0027 | 0.0268 | 4.7740 | −1.0357 | 2.6358 | 0.0272 | 0.0260 |
| 4.5659 | 0.9317 | 2.6660 | 0.0101 | 0.0269 | 2.2991 | −0.3983 | 2.6635 | 0.0187 | 0.0262 |
| 3.2618 | 0.3351 | 2.6549 | 0.0026 | 0.0284 | −1.0895 | 0.5343 | 2.6718 | 0.0236 | 0.0265 |
| 0.2888 | 0.4908 | 2.6363 | 0.0037 | 0.0286 | −3.2780 | 0.8399 | 2.6332 | 0.0272 | 0.0249 |
| 3.9037 | −0.0052 | 2.6558 | 0.0094 | 0.0283 | 1.5092 | −0.2351 | 2.6305 | 0.0232 | 0.0147 |
| 6.3764 | −0.0523 | 2.6490 | 0.0207 | 0.0286 | 3.6238 | −0.0202 | 2.6333 | 0.0269 | 0.0253 |
| 3.8420 | 0.7315 | 2.6564 | 0.0173 | 0.0274 | −0.6864 | −0.7927 | 2.6653 | 0.0192 | 0.0244 |
| 3.5595 | 1.0538 | 2.6607 | 0.0018 | 0.0260 | 2.3271 | 0.5117 | 2.6576 | 0.0111 | 0.0268 |
| 1.4890 | 1.5426 | 2.6444 | 0.0038 | 0.0281 | 3.4678 | −0.5160 | 2.6312 | 0.0219 | 0.0271 |
| 1.6431 | 1.5211 | 2.6623 | 0.0003 | 0.0280 | 4.0844 | 0.3381 | 2.6414 | 0.0235 | 0.0272 |
| 7.0789 | 1.5869 | 2.6375 | 0.0109 | 0.0280 | 1.7332 | 1.4703 | 2.6545 | 0.0288 | 0.0274 |
| 0.4056 | 1.1337 | 2.6308 | −0.0004 | 0.0281 | 1.5435 | 0.2032 | 2.6426 | 0.0270 | 0.0284 |
| 1.9508 | 0.1685 | 2.6672 | −0.0080 | 0.0283 | 3.6030 | 0.1524 | 2.6446 | 0.0250 | 0.0288 |
| 3.5263 | 0.7111 | 2.6749 | −0.0015 | 0.0298 | 2.3926 | 1.0664 | 2.6427 | 0.0253 | 0.0271 |
| 2.9074 | 0.8124 | 2.6472 | 0.0074 | 0.0296 | 3.3148 | 0.8710 | 2.6512 | 0.0206 | 0.0288 |
| 4.3008 | 1.1020 | 2.6594 | 0.0050 | 0.0303 | 5.5580 | 2.5570 | 2.6410 | 0.0170 | 0.0290 |
| 4.5186 | 3.1189 | 2.6580 | 0.0053 | 0.0301 | 6.5631 | 1.3390 | 2.6522 | 0.0251 | 0.0279 |
| 4.4749 | 0.9265 | 2.6566 | 0.0101 | 0.0285 | 4.9646 | 0.7019 | 2.6284 | 0.0204 | 0.0259 |
| 3.9182 | 0.3658 | 2.6546 | 0.0183 | 0.0267 | 2.8412 | 0.1108 | 2.6576 | 0.0219 | 0.0262 |
| 1.9300 | 0.0746 | 2.6647 | 0.0062 | 0.0265 | 2.0493 | 0.7615 | 2.6695 | 0.0191 | 0.0286 |
| 0.2646 | −0.0234 | 2.6416 | 0.0095 | 0.0263 | 1.0309 | −0.2066 | 2.6537 | 0.0152 | 0.0287 |
| −0.4509 | 0.1115 | 2.6648 | 0.0076 | 0.0270 | 1.8359 | −0.4614 | 2.6623 | 0.0172 | 0.0274 |
| −0.1518 | 0.3614 | 2.6626 | 0.0069 | 0.0270 | 2.7884 | 1.0948 | 2.6535 | 0.0106 | 0.0274 |
| 0.6836 | 0.4393 | 2.6526 | 0.0102 | 0.0265 | 3.1118 | −1.2587 | 2.6532 | 0.0106 | 0.0278 |
| −1.7740 | 0.1456 | 2.6445 | 0.0045 | 0.0268 | 4.5918 | −0.6839 | 2.6432 | 0.0137 | 0.0275 |
| −3.6034 | 1.1210 | 2.6592 | 0.0065 | 0.0283 | 0.5702 | −0.2243 | 2.6595 | 0.0052 | 0.0261 |
| 0.3268 | 1.3207 | 2.6515 | 0.0038 | 0.0266 | 1.8162 | 0.8339 | 2.6661 | 0.0017 | 0.0264 |
| 3.5586 | 1.0948 | 2.6293 | 0.0035 | 0.0265 | 3.7247 | 1.3633 | 2.6557 | 0.0142 | 0.0277 |
| 4.4315 | 1.1170 | 2.6597 | 0.0019 | 0.0260 | 1.0224 | −0.0986 | 2.6554 | 0.0144 | 0.0295 |
| 3.1592 | 1.7409 | 2.6691 | −0.0002 | 0.0274 | 4.8915 | −0.8357 | 2.6505 | 0.0091 | 0.0292 |
| 0.5839 | 1.3312 | 2.6584 | 0.0071 | 0.0279 | 3.8756 | −0.2202 | 2.6538 | 0.0028 | 0.0285 |
| 3.6199 | 0.4896 | 2.6590 | 0.0105 | 0.0270 | 2.5612 | 1.5678 | 2.6451 | 0.0192 | 0.0286 |
| 0.9424 | 1.1979 | 2.6426 | 0.0083 | 0.0263 | 5.1084 | 1.3565 | 2.6446 | 0.0236 | 0.0288 |
| 0.5843 | 1.2535 | 2.6618 | 0.0160 | 0.0260 | 2.8938 | 1.7622 | 2.6685 | 0.0200 | 0.0290 |
| 1.9951 | 2.0845 | 2.6624 | 0.0143 | 0.0247 | 2.9189 | 1.0361 | 2.6562 | 0.0087 | 0.0269 |
| 1.2262 | −0.0298 | 2.6513 | 0.0124 | 0.0275 | 0.3924 | 2.1663 | 2.6554 | 0.0071 | 0.0287 |
| 0.6420 | −0.2706 | 2.6393 | 0.0102 | 0.0285 | 4.5414 | 0.8863 | 2.6598 | 0.0014 | 0.0275 |
| −0.8042 | −0.4390 | 2.6416 | 0.0064 | 0.0280 | 1.0753 | −0.1298 | 2.6423 | 0.0020 | 0.0292 |
| 1.4448 | 0.0099 | 2.6592 | 0.0127 | 0.0267 | 0.8121 | −0.5827 | 2.6658 | 0.0047 | 0.0296 |
| 1.8841 | 0.3502 | 2.6514 | 0.0135 | 0.0272 | 1.4015 | −0.1371 | 2.6499 | 0.0160 | 0.0283 |
| −0.2486 | 0.5802 | 2.6519 | 0.0035 | 0.0266 | 2.1710 | 0.0892 | 2.6521 | 0.0098 | 0.0285 |
| 1.1293 | 0.1072 | 2.6474 | 0.0032 | 0.0276 | 0.1990 | 0.2120 | 2.6614 | 0.0033 | 0.0280 |
| −1.0104 | 0.4067 | 2.6515 | 0.0089 | 0.0276 | 2.2428 | −0.1115 | 2.6398 | 0.0193 | 0.0271 |
| 2.0688 | 0.3041 | 2.6280 | 0.0114 | 0.0278 | 1.5548 | 0.3439 | 2.6594 | 0.0093 | 0.0255 |
| 2.7238 | 0.4195 | 2.6678 | 0.0069 | 0.0280 | 0.2581 | −0.2724 | 2.6442 | 0.0102 | 0.0264 |
| 0.4229 | 0.3570 | 2.6406 | 0.0147 | 0.0266 | 3.2040 | 0.6067 | 2.6419 | 0.0085 | 0.0265 |
| −0.9443 | 0.8134 | 2.6451 | 0.0007 | 0.0266 | 3.3994 | −0.9342 | 2.6442 | 0.0216 | 0.0268 |
| 0.3128 | 2.4965 | 2.6588 | 0.0149 | 0.0267 | 3.2037 | 0.0887 | 2.6376 | 0.0171 | 0.0282 |
| 1.1257 | 1.1640 | 2.6530 | 0.0108 | 0.0274 | 3.0981 | 1.3866 | 2.6370 | 0.0256 | 0.0276 |
| 4.0244 | 1.2582 | 2.6627 | 0.0151 | 0.0270 | 1.9120 | −0.1101 | 2.6397 | 0.0207 | 0.0279 |
| 1.8541 | 0.3421 | 2.6470 | 0.0110 | 0.0263 | 3.3069 | 0.5651 | 2.6455 | 0.0108 | 0.0288 |
| 0.4366 | 0.1956 | 2.6421 | 0.0091 | 0.0261 | 3.8852 | 0.2353 | 2.6817 | 0.0094 | 0.0268 |
| 1.9781 | −0.6378 | 2.6464 | 0.0124 | 0.0256 | 2.2380 | −0.3964 | 2.6630 | 0.0206 | 0.0274 |
| 3.8899 | 0.0540 | 2.6525 | 0.0134 | 0.0269 | 2.6375 | 0.0467 | 2.6463 | 0.0212 | 0.0262 |
| 5.1043 | −0.2189 | 2.6408 | 0.0063 | 0.0266 | 2.6117 | 0.7350 | 2.6554 | 0.0164 | 0.0263 |
| 4.1349 | −0.7842 | 2.6429 | −0.0021 | 0.0274 | 4.7098 | 0.2994 | 2.6426 | 0.0261 | 0.0273 |
| 3.1778 | 0.0280 | 2.6731 | −0.0007 | 0.0275 | 2.7484 | 0.3372 | 2.6469 | 0.0275 | 0.0282 |
| 3.0040 | −0.3277 | 2.6527 | −0.0001 | 0.0272 | 1.3111 | 1.4114 | 2.6481 | 0.0238 | 0.0289 |
| 2.4491 | 0.8047 | 2.6499 | 0.0136 | 0.0277 | 1.5063 | −0.3867 | 2.6476 | 0.0200 | 0.0283 |
| 3.6734 | 0.8520 | 2.6235 | 0.0235 | 0.0261 | 3.4101 | 0.3981 | 2.6491 | 0.0224 | 0.0287 |
| 4.0732 | 1.0147 | 2.6610 | 0.0172 | 0.0280 | 1.9477 | 0.7951 | 2.6304 | 0.0214 | 0.0280 |
| 2.4566 | −0.3133 | 2.6466 | 0.0150 | 0.0290 | 1.2475 | 0.8096 | 2.6447 | 0.0152 | 0.0295 |
| 2.3615 | −1.0314 | 2.6431 | 0.0171 | 0.0292 | 1.7750 | −0.4215 | 2.6451 | 0.0166 | 0.0288 |
| 2.7956 | 2.1782 | 2.6457 | 0.0113 | 0.0292 | 4.1949 | −0.4634 | 2.6538 | 0.0107 | 0.0282 |
| 3.8857 | 0.5837 | 2.6401 | 0.0047 | 0.0270 | 0.9383 | 0.3368 | 2.6471 | 0.0040 | 0.0286 |
| 0.3098 | 0.1682 | 2.6448 | 0.0018 | 0.0280 | 0.1038 | 1.2578 | 2.6753 | 0.0036 | 0.0283 |
| 1.4268 | 0.7145 | 2.6525 | 0.0032 | 0.0279 | 1.4740 | 0.5378 | 2.6521 | 0.0078 | 0.0287 |
| 5.0809 | 0.8639 | 2.6639 | 0.0027 | 0.0284 | 1.8098 | 0.9854 | 2.6506 | 0.0049 | 0.0283 |
| 2.7999 | 0.7697 | 2.6583 | 0.0129 | 0.0275 | 2.5242 | 0.8604 | 2.6420 | 0.0160 | 0.0282 |
| 2.4657 | 2.3038 | 2.6665 | 0.0170 | 0.0279 | −1.4269 | 0.5906 | 2.6524 | 0.0139 | 0.0270 |
| 1.3586 | 1.9390 | 2.6527 | 0.0117 | 0.0288 | −0.7576 | 0.9428 | 2.6161 | 0.0222 | 0.0260 |
| 0.4252 | 1.6008 | 2.6731 | 0.0086 | 0.0287 | 2.2445 | 0.5815 | 2.6567 | 0.0133 | 0.0279 |
| 3.2488 | −0.3095 | 2.6445 | 0.0080 | 0.0298 | 4.0496 | 0.3554 | 2.6583 | 0.0225 | 0.0283 |
| 3.4282 | 0.0413 | 2.6503 | 0.0036 | 0.0298 | 1.8331 | −0.1162 | 2.6575 | 0.0105 | 0.0282 |
| −0.1567 | 0.4306 | 2.6588 | 0.0028 | 0.0297 | 1.8228 | 0.6216 | 2.6499 | −0.0018 | 0.0283 |
| −0.3306 | −0.1996 | 2.6620 | 0.0146 | 0.0298 | 2.4639 | 1.4466 | 2.6479 | 0.0057 | 0.0300 |
| 3.1718 | −0.2588 | 2.6601 | 0.0075 | 0.0282 | 2.4224 | 0.4991 | 2.6380 | 0.0141 | 0.0305 |
| 4.5633 | −0.6224 | 2.6515 | 0.0121 | 0.0270 | 0.5228 | −0.2796 | 2.6530 | 0.0152 | 0.0295 |

TABLE 2-continued

| | | | | | | | | | |
|---|---|---|---|---|---|---|---|---|---|
| 2.3567 | −0.2019 | 2.6475 | 0.0081 | 0.0279 | 0.3318 | 0.7774 | 2.6590 | 0.0143 | 0.0288 |
| 2.9599 | −0.4544 | 2.6564 | 0.0159 | 0.0286 | 3.3861 | −0.8487 | 2.6456 | 0.0237 | 0.0266 |
| 0.1565 | −0.0316 | 2.6530 | 0.0139 | 0.0282 | 5.6970 | 0.9246 | 2.6469 | 0.0175 | 0.0264 |
| 1.0336 | 1.3844 | 2.6379 | 0.0228 | 0.0295 | 5.2257 | 0.7969 | 2.6423 | 0.0136 | 0.0267 |
| 3.2637 | 0.4233 | 2.6566 | 0.0179 | 0.0281 | 4.1179 | 0.8993 | 2.6331 | 0.0183 | 0.0276 |
| 4.9498 | 0.8442 | 2.6484 | 0.0291 | 0.0290 | 3.8998 | −0.5084 | 2.6355 | 0.0171 | 0.0274 |
| 2.8847 | −0.0839 | 2.6452 | 0.0121 | 0.0293 | 3.5508 | −0.4697 | 2.6595 | 0.0100 | 0.0272 |
| 3.6036 | 0.6884 | 2.6542 | 0.0091 | 0.0299 | 1.8113 | −0.0557 | 2.6595 | 0.0017 | 0.0263 |
| 3.7397 | −0.4237 | 2.6604 | 0.0070 | 0.0303 | 2.7113 | 0.1602 | 2.6347 | 0.0082 | 0.0279 |
| 5.6072 | 0.1001 | 2.6582 | 0.0180 | 0.0291 | 2.4072 | 1.7801 | 2.6561 | 0.0114 | 0.0287 |
| 3.9784 | −0.0682 | 2.6508 | 0.0125 | 0.0286 | 4.3130 | 0.1972 | 2.6514 | 0.0100 | 0.0290 |
| 3.6761 | −0.0185 | 2.6524 | 0.0138 | 0.0284 | 2.4398 | −0.2087 | 2.6449 | 0.0150 | 0.0290 |
| 2.2692 | 0.2765 | 2.6479 | 0.0191 | 0.0279 | 2.5890 | 0.5050 | 2.6553 | 0.0174 | 0.0286 |
| 0.0502 | 0.4871 | 2.6591 | 0.0216 | 0.0264 | 1.2731 | 2.1100 | 2.6455 | 0.0185 | 0.0288 |
| 0.8404 | 0.5158 | 2.6550 | 0.0173 | 0.0267 | 2.5884 | 0.8251 | 2.6630 | 0.0212 | 0.0287 |
| 2.1339 | 3.0670 | 2.6460 | 0.0156 | 0.0276 | 0.8515 | 1.2410 | 2.6491 | 0.0112 | 0.0278 |
| 0.0947 | 1.5087 | 2.6667 | 0.0107 | 0.0266 | 1.1706 | 1.4115 | 2.6599 | 0.0093 | 0.0285 |
| 1.3842 | 0.6537 | 2.6383 | 0.0050 | 0.0273 | 5.0791 | 2.2891 | 2.6597 | 0.0114 | 0.0293 |
| −0.3840 | 0.8243 | 2.6403 | 0.0152 | 0.0269 | 0.6228 | 0.5953 | 2.6490 | 0.0100 | 0.0291 |
| −1.6382 | −0.1082 | 2.6569 | 0.0097 | 0.0274 | 0.2148 | −0.8826 | 2.6350 | 0.0070 | 0.0287 |
| 0.8941 | 0.3400 | 2.6423 | 0.0102 | 0.0268 | 2.2044 | 0.4423 | 2.6377 | 0.0146 | 0.0283 |
| 2.7181 | −0.0054 | 2.6492 | 0.0293 | 0.0252 | 2.5474 | 1.0160 | 2.6441 | −0.0017 | 0.0290 |
| 1.0129 | 3.1164 | 2.6438 | 0.0253 | 0.0264 | 3.7621 | 1.0144 | 2.6504 | 0.0044 | 0.0273 |
| 0.9331 | 0.1955 | 2.6374 | 0.0204 | 0.0263 | 3.8919 | −0.0224 | 2.6381 | 0.0104 | 0.0264 |
| 0.6524 | 0.6338 | 2.6304 | 0.0176 | 0.0268 | −0.2702 | 1.2786 | 2.6654 | 0.0064 | 0.0279 |
| 2.3501 | 1.0547 | 2.6633 | 0.0141 | 0.0270 | −0.1055 | 1.1032 | 2.6311 | 0.0127 | 0.0275 |
| 2.0990 | 2.0117 | 2.6654 | 0.0094 | 0.0264 | −0.1303 | 0.4644 | 2.6320 | 0.0201 | 0.0286 |
| 2.7173 | 0.5939 | 2.6617 | 0.0123 | 0.0273 | 0.5568 | −0.1941 | 2.6359 | 0.0112 | 0.0277 |
| 3.1411 | −0.0243 | 2.6463 | 0.0157 | 0.0279 | 1.6020 | 0.7825 | 2.6504 | 0.0121 | 0.0294 |
| 3.5744 | 0.3333 | 2.6463 | 0.0060 | 0.0277 | 1.8143 | 0.5321 | 2.6609 | 0.0184 | 0.0307 |
| 1.3423 | 0.6023 | 2.6696 | 0.0075 | 0.0275 | 5.1196 | 1.7048 | 2.6547 | 0.0184 | 0.0302 |
| 2.4877 | 0.0307 | 2.6250 | 0.0078 | 0.0267 | 3.3711 | 0.3097 | 2.6604 | 0.0129 | 0.0300 |
| 2.3450 | 0.8141 | 2.6411 | 0.0070 | 0.0262 | 1.8721 | 0.6081 | 2.6505 | 0.0140 | 0.0289 |
| 1.0281 | 1.1227 | 2.6487 | 0.0115 | 0.0266 | 1.7909 | 0.7543 | 2.6382 | 0.0073 | 0.0241 |
| 1.6334 | 0.3851 | 2.6420 | 0.0113 | 0.0279 | 0.2996 | 2.0289 | 2.6432 | 0.0120 | 0.0268 |
| 2.3765 | 0.8552 | 2.6319 | 0.0131 | 0.0278 | −0.4868 | 0.8916 | 2.6765 | 0.0049 | 0.0267 |
| 0.5997 | 0.2045 | 2.6471 | 0.0146 | 0.0279 | −0.9695 | 1.4391 | 2.6457 | 0.0112 | 0.0272 |
| 2.3748 | 0.6919 | 2.6551 | 0.0134 | 0.0274 | 2.1807 | 1.3016 | 2.6471 | 0.0152 | 0.0272 |
| 4.1416 | −0.0590 | 2.6574 | 0.0124 | 0.0271 | 4.0239 | 1.8312 | 2.6445 | 0.0090 | 0.0272 |
| 0.7270 | −0.0817 | 2.6518 | 0.0099 | 0.0276 | 3.9373 | 1.1000 | 2.6570 | 0.0061 | 0.0284 |
| 0.8343 | 1.5377 | 2.6524 | 0.0033 | 0.0283 | 2.3175 | 1.5627 | 2.6611 | 0.0038 | 0.0276 |
| 0.0224 | 1.0780 | 2.6399 | 0.0011 | 0.0283 | 1.8356 | 2.0715 | 2.6623 | 0.0034 | 0.0269 |
| 0.1904 | 1.0444 | 2.6452 | −0.0005 | 0.0285 | −0.7619 | 0.2668 | 2.6391 | 0.0116 | 0.0278 |
| 1.7659 | 0.4891 | 2.6526 | 0.0062 | 0.0282 | 0.7556 | 0.5534 | 2.6620 | 0.0193 | 0.0284 |
| 1.9214 | 0.2044 | 2.6553 | 0.0063 | 0.0280 | 3.4047 | 0.4969 | 2.6287 | 0.0004 | 0.0298 |
| 4.2058 | 0.3407 | 2.6628 | 0.0036 | 0.0288 | 0.4053 | 1.4357 | 2.6665 | 0.0052 | 0.0303 |
| 5.2014 | 1.2805 | 2.6407 | 0.0106 | 0.0272 | 2.6414 | −0.1232 | 2.6460 | 0.0139 | 0.0299 |
| 4.9485 | 2.0509 | 2.6474 | 0.0103 | 0.0267 | 2.6530 | 0.4778 | 2.6615 | 0.0162 | 0.0287 |
| 2.5497 | 0.7552 | 2.6476 | 0.0114 | 0.0277 | 2.3225 | −0.6477 | 2.6452 | 0.0143 | 0.0290 |
| 2.4044 | −0.3853 | 2.6608 | 0.0061 | 0.0281 | 2.5458 | −0.5230 | 2.6639 | 0.0049 | 0.0241 |
| 2.3590 | −0.5616 | 2.6515 | 0.0018 | 0.0243 | 2.1681 | 0.4676 | 2.6568 | 0.0080 | 0.0264 |
| 2.8858 | −0.7616 | 2.6560 | 0.0011 | 0.0280 | 1.7262 | −0.3134 | 2.6617 | 0.0123 | 0.0263 |
| 4.6094 | −0.1198 | 2.6584 | 0.0077 | 0.0288 | 1.2232 | 0.0613 | 2.6690 | 0.0115 | 0.0257 |
| 1.6144 | −0.1473 | 2.6554 | 0.0136 | 0.0295 | 1.3961 | 0.7314 | 2.6646 | 0.0060 | 0.0263 |
| 2.1239 | −0.0402 | 2.6505 | 0.0074 | 0.0295 | 3.1541 | −1.2123 | 2.6644 | −0.0006 | 0.0272 |
| 1.9313 | 0.6639 | 2.6434 | 0.0209 | 0.0294 | 4.5294 | −0.3398 | 2.6704 | −0.0017 | 0.0282 |
| 0.9533 | 1.1370 | 2.6378 | 0.0154 | 0.0280 | 5.3214 | 0.3144 | 2.6411 | 0.0053 | 0.0286 |
| 1.5484 | 0.5190 | 2.6457 | 0.0110 | 0.0295 | 4.7477 | 0.3546 | 2.6264 | 0.0046 | 4.0290 |
| 5.2566 | 2.5140 | 2.6556 | 0.0111 | 0.0290 | 3.2063 | 1.7448 | 2.6459 | 0.0039 | 0.0306 |
| 0.4526 | 1.3544 | 2.6499 | 0.0126 | 0.0270 | −0.1790 | −0.2523 | 2.6463 | 0.0154 | 0.0317 |
| 0.5833 | 1.1994 | 2.6595 | 0.0094 | 0.0269 | 1.3701 | 0.9426 | 2.6622 | 0.0175 | 0.0315 |
| −1.3644 | 0.7704 | 2.6577 | 0.0095 | 0.0268 | 1.7797 | 0.5268 | 2.6547 | 0.0150 | 0.0303 |
| 1.2286 | 0.9597 | 2.6521 | 0.0054 | 0.0285 | 1.9769 | 0.8541 | 2.6612 | 0.0140 | 0.0299 |
| 1.5400 | 0.5103 | 2.6489 | 0.0072 | 0.0292 | 1.2695 | 0.2718 | 2.6516 | 0.0180 | 0.0297 |
| −0.2355 | −1.8067 | 2.6349 | 0.0104 | 0.0305 | 4.6910 | 0.3200 | 2.6446 | 0.0156 | 0.0301 |
| 0.3408 | 0.8896 | 2.6270 | 0.0132 | 0.0292 | 4.3224 | −0.2442 | 2.6515 | 0.0162 | 0.0306 |
| −1.3284 | 0.6715 | 2.6637 | 0.0154 | 0.0286 | 4.4644 | 0.0746 | 2.6687 | 0.0146 | 0.0297 |
| 0.0159 | 0.5726 | 2.6496 | 0.0180 | 0.0278 | −0.9428 | 0.1944 | 2.6583 | 0.0150 | 0.0283 |
| 1.7730 | 0.7545 | 2.6261 | 0.0239 | 0.0287 | 0.3166 | −0.0272 | 2.6718 | 0.0076 | 0.0244 |
| 0.8351 | 0.3129 | 2.6551 | 0.0190 | 0.0293 | 3.1396 | −0.0111 | 2.6564 | 0.0122 | 0.0247 |
| 0.6006 | 0.6993 | 2.6576 | 0.0094 | 0.0289 | 6.3271 | 1.0865 | 2.6439 | 0.0192 | 0.0277 |
| 2.0745 | 0.1167 | 2.6354 | 0.0012 | 0.0276 | 4.0370 | 1.2765 | 2.6696 | 0.0146 | 0.0279 |
| −0.9230 | 0.7843 | 2.6515 | 0.0010 | 0.0275 | 3.9099 | 1.6605 | 2.6420 | 0.0050 | 0.0279 |
| −0.5112 | 0.3836 | 2.6546 | 0.0100 | 0.0276 | 3.1395 | 0.9480 | 2.6378 | 0.0095 | 0.0241 |
| 3.8128 | 1.6595 | 2.6556 | 0.0142 | 0.0276 | 2.8466 | 0.1461 | 2.6525 | 0.0110 | 0.0240 |
| 2.5735 | 1.1601 | 2.6401 | 0.0150 | 0.0274 | 2.6217 | 0.2198 | 2.6538 | 0.0194 | 0.0277 |
| 2.8626 | 0.2179 | 2.6656 | 0.0130 | 0.0278 | 2.5450 | −0.2211 | 2.6546 | 0.0168 | 0.0275 |
| 0.7093 | 0.9848 | 2.6416 | −0.0015 | 0.0268 | 1.7734 | −0.4521 | 2.6690 | 0.0140 | 0.0269 |
| 0.3718 | −0.1843 | 2.6389 | −0.0081 | 0.0274 | 0.1994 | −0.1023 | 2.6459 | 0.0099 | 0.0264 |

TABLE 2-continued

| | | | | | | | | | |
|---|---|---|---|---|---|---|---|---|---|
| 4.0066 | −0.9938 | 2.6534 | −0.0085 | 0.0274 | −0.2664 | −0.3099 | 2.6442 | 0.0140 | 0.0259 |
| 3.1455 | −0.8543 | 2.6474 | 0.0000 | 0.0274 | 2.2020 | 0.6222 | 2.6534 | 0.0117 | 0.0251 |
| 1.1546 | 1.7899 | 2.6351 | 0.0047 | 0.0273 | 3.5288 | 0.3787 | 2.6603 | 0.0074 | 0.0261 |
| 3.0318 | 1.8146 | 2.6625 | 0.0127 | 0.0269 | 4.2905 | 0.5942 | 2.6524 | 0.0119 | 0.0269 |
| 2.2929 | 0.6435 | 2.6342 | 0.0220 | 0.0264 | 5.0716 | 0.1238 | 2.6551 | 0.0094 | 0.0264 |
| 1.2793 | 0.4002 | 2.6510 | 0.0064 | 0.0271 | 3.5944 | 0.0447 | 2.6452 | 0.0175 | 0.0268 |
| 2.7198 | −0.8388 | 2.6535 | 0.0038 | 0.0293 | 3.3508 | 1.1548 | 2.6703 | 0.0270 | 0.0259 |
| 3.8594 | −0.7633 | 2.6595 | 0.0018 | 0.0302 | 0.4701 | −0.3865 | 2.6434 | 0.0132 | 0.0266 |
| 0.4671 | 1.2976 | 2.6700 | 0.0058 | 0.0304 | 0.3436 | 0.4452 | 2.6521 | 0.0048 | 0.0267 |
| −0.1000 | 0.3067 | 2.6306 | 0.0140 | 0.0298 | 0.4613 | 1.3513 | 2.6386 | 0.0118 | 0.0265 |
| 2.1964 | −1.3313 | 2.6369 | 0.0097 | 0.0277 | 1.2653 | 0.8488 | 2.6543 | 0.0104 | 0.0270 |
| 1.0857 | −0.0743 | 2.6382 | 0.0082 | 0.0277 | 3.3631 | 0.6235 | 2.6569 | 0.0186 | 0.0293 |
| 3.9880 | 0.2847 | 2.6685 | 0.0066 | 0.0275 | 6.1945 | 0.3757 | 2.6429 | 0.0159 | 0.0299 |
| 2.8966 | −0.1400 | 2.6551 | 0.0176 | 0.0271 | 4.7537 | −0.4098 | 2.6342 | 0.0154 | 0.0285 |
| 2.3722 | −0.4042 | 2.6477 | 0.0175 | 0.0269 | 7.4002 | −0.5049 | 2.6490 | 0.0148 | 0.0297 |
| 0.4406 | 0.0403 | 2.6572 | 0.0119 | 0.0268 | 7.6175 | 0.0821 | 2.6471 | 0.0107 | 0.0286 |
| 2.5005 | 0.1795 | 2.6713 | 0.0089 | 0.0287 | 3.4082 | −0.5240 | 2.6322 | 0.0081 | 0.0286 |
| 2.5813 | −0.0620 | 2.6429 | 0.0216 | 0.0291 | 3.0721 | −0.9999 | 2.6675 | 0.0087 | 0.0280 |
| 2.0566 | 0.4226 | 2.6458 | 0.0176 | 0.0279 | 3.6894 | −1.0032 | 2.6547 | 0.0243 | 0.0281 |
| −0.4289 | 0.3795 | 2.6431 | 0.0192 | 0.0287 | 4.1259 | −0.1939 | 2.6438 | 0.0251 | 0.0269 |
| −0.3037 | 0.9158 | 2.6559 | 0.0217 | 0.0292 | 3.2361 | 0.4673 | 2.6397 | 0.0191 | 0.0267 |
| 3.9685 | 1.1807 | 2.6462 | 0.0181 | 0.0285 | 0.3932 | −0.0271 | 2.6346 | 0.0302 | 0.0263 |
| 4.4875 | 0.4040 | 2.6470 | 0.0110 | 0.0286 | 2.7631 | 0.1423 | 2.6263 | 0.0200 | 0.0280 |
| 5.4220 | −0.4790 | 2.6806 | 0.0051 | 0.0270 | 5.3865 | −0.2185 | 2.6418 | 0.0219 | 0.0271 |
| −0.2256 | −0.0803 | 2.6405 | 0.0175 | 0.0273 | 6.3875 | 0.7883 | 2.6635 | 0.0162 | 0.0283 |
| 1.7033 | −0.3566 | 2.6518 | 0.0124 | 0.0263 | 0.8251 | −0.1095 | 2.6573 | 0.0011 | 0.0284 |
| 0.8811 | −0.0025 | 2.6681 | 0.0203 | 0.0269 | 2.8821 | −0.1343 | 2.6544 | 0.0076 | 0.0292 |
| 1.9472 | 0.5734 | 2.6467 | 0.0219 | 0.0258 | 3.7535 | −0.7944 | 2.6549 | 0.0087 | 0.0279 |
| −0.6770 | 0.6509 | 2.6530 | 0.0191 | 0.0259 | 3.0660 | −0.2597 | 2.6505 | 0.0151 | 0.0286 |
| −1.3929 | 0.1215 | 2.6527 | 0.0139 | 0.0270 | 3.5204 | 0.8623 | 2.6360 | 0.0133 | 0.0294 |
| 0.3664 | −0.2283 | 2.6527 | 0.0045 | 0.0263 | 2.6422 | 2.3788 | 2.6371 | 0.0258 | 0.0300 |
| 3.9267 | 0.1890 | 2.6529 | 0.0011 | 0.0259 | 0.9362 | 1.3166 | 2.6518 | 0.0221 | 0.0286 |
| 3.6658 | 0.1507 | 2.6636 | 0.0015 | 0.0258 | 2.0142 | 0.4636 | 2.6392 | 0.0151 | 0.0284 |
| 3.6656 | 0.4529 | 2.6500 | 0.0067 | 0.0269 | 3.8841 | −0.8248 | 2.6407 | 0.0237 | 0.0269 |
| 3.9156 | 1.2501 | 2.6691 | 0.0054 | 0.0271 | 3.7192 | −0.8515 | 2.6417 | 0.0159 | 0.0265 |
| 0.3670 | 1.4592 | 2.6570 | 0.0117 | 0.0273 | 1.3832 | 0.1959 | 2.6409 | 0.0145 | 0.0283 |
| 0.8352 | 0.9254 | 2.6459 | 0.0034 | 0.0265 | −0.4132 | 1.0405 | 2.6359 | 0.0118 | 0.0270 |
| 0.0399 | 1.1958 | 2.6605 | 0.0077 | 0.0270 | 1.2472 | −0.8217 | 2.6503 | 0.0162 | 0.0270 |
| 0.2184 | 1.1788 | 2.6459 | 0.0116 | 0.0279 | 2.1729 | −0.4104 | 2.6391 | 0.0177 | 0.0287 |
| 1.5251 | 0.4561 | 2.6224 | 0.0180 | 0.0270 | 0.4111 | −0.5810 | 2.6548 | 0.0134 | 0.0273 |
| 1.1781 | 2.5312 | 2.6479 | 0.0221 | 0.0264 | −1.2347 | 0.2115 | 2.6650 | 0.0168 | 0.0266 |
| −0.2513 | 1.7074 | 2.6367 | 0.0194 | 0.0262 | 0.8757 | 1.2110 | 2.6541 | 0.0157 | 0.0266 |
| −1.0746 | 2.4387 | 2.6464 | 0.0130 | 0.0261 | 2.1248 | 0.5965 | 2.6675 | 0.0073 | 0.0286 |
| 2.1394 | 1.9493 | 2.6531 | 0.0069 | 0.0270 | 3.1057 | −0.4192 | 2.6631 | 0.0185 | 0.0277 |
| 3.1150 | 1.4250 | 2.6579 | 0.0012 | 0.0288 | 4.4524 | −0.3170 | 2.6552 | 0.0121 | 0.0276 |
| 3.2751 | −1.1959 | 2.6624 | 0.0027 | 0.0294 | 3.4603 | −0.2643 | 2.6422 | 0.0067 | 0.0276 |
| 1.4003 | 0.3451 | 2.6572 | −0.0052 | 0.0306 | 4.1996 | 1.5294 | 2.6578 | 0.0025 | 0.0278 |
| 0.4113 | 0.6007 | 2.6564 | −0.0104 | 0.0289 | 3.9469 | 0.4750 | 2.6492 | 0.0072 | 0.0281 |
| 3.9831 | −0.0673 | 2.6564 | −0.0046 | 0.0295 | 2.8056 | 0.8412 | 2.6631 | 0.0060 | 0.0291 |
| 3.3553 | 0.5001 | 2.6649 | −0.0054 | 0.0296 | 0.7569 | 0.0451 | 2.6563 | 0.0226 | 0.0287 |
| 4.3881 | 0.6024 | 2.6452 | −0.0030 | 0.0294 | 1.6724 | 0.5162 | 2.6526 | 0.0130 | 0.0287 |
| 5.3560 | 0.0170 | 2.6348 | 0.0025 | 0.0292 | 2.3075 | 0.4833 | 2.6493 | 0.0107 | 0.0281 |
| 4.3331 | 0.1299 | 2.6534 | −0.0017 | 0.0290 | 2.1919 | 0.4709 | 2.6400 | 0.0136 | 0.0277 |
| 3.0023 | −0.0297 | 2.6452 | −0.0130 | 0.0292 | 1.9579 | 1.0331 | 2.6439 | 0.0187 | 0.0266 |
| 4.5388 | 1.5081 | 2.6604 | −0.0015 | 0.0290 | −1.3853 | 0.1087 | 2.6609 | 0.0146 | 0.0266 |
| 1.6685 | 0.6378 | 2.6665 | 0.0010 | 0.0281 | −1.1403 | 0.5206 | 2.6548 | 0.0178 | 0.0275 |
| 3.6542 | 0.9829 | 2.6404 | 0.0136 | 0.0283 | −0.8831 | 0.0882 | 2.6488 | 0.0118 | 0.0265 |
| 3.8617 | 1.0914 | 2.6691 | 0.0103 | 0.0287 | 0.2476 | 1.5763 | 2.6691 | 0.0120 | 0.0268 |
| 4.1161 | 0.4701 | 2.6483 | 0.0067 | 0.0274 | 1.1874 | 0.0094 | 2.6779 | 0.0124 | 0.0266 |
| 3.4111 | 0.2771 | 2.6678 | 0.0126 | 0.0283 | 0.9082 | 0.3569 | 2.6316 | 0.0198 | 0.0259 |
| 3.7352 | 0.2541 | 2.6485 | 0.0121 | 0.0272 | 0.9223 | 0.1321 | 2.6427 | 0.0187 | 0.0277 |
| 2.7725 | −0.6144 | 2.6510 | 0.0017 | 0.0277 | 0.1546 | 0.1286 | 2.6423 | 0.0186 | 0.0263 |
| 2.0919 | 0.2541 | 2.6612 | −0.0007 | 0.0282 | −0.0506 | 0.3576 | 2.6472 | 0.0135 | 0.0269 |
| 1.4610 | 0.9165 | 2.6446 | 0.0084 | 0.0271 | 1.3947 | 0.3161 | 2.6536 | 0.0123 | 0.0272 |
| 0.5206 | 0.3015 | 2.6346 | 0.0040 | 0.0270 | 2.0053 | 0.4975 | 2.6200 | 0.0161 | 0.0292 |
| 2.7937 | 0.0902 | 2.6474 | 0.0069 | 0.0261 | 2.8223 | −0.3436 | 2.6468 | 0.0112 | 0.0296 |
| 1.1605 | 0.1573 | 2.6523 | 0.0120 | 0.0275 | 1.4941 | 0.0100 | 2.6540 | 0.0063 | 0.0316 |
| 0.4792 | 0.9393 | 2.6766 | −0.0024 | 0.0258 | 3.4509 | 0.1676 | 2.6434 | 0.0055 | 0.0295 |
| 1.2909 | 0.1712 | 2.6493 | 0.0026 | 0.0269 | 5.8147 | 0.8383 | 2.6595 | 0.0120 | 0.0291 |
| 0.0445 | 0.4291 | 2.6656 | 0.0019 | 0.0282 | 4.7016 | −0.0877 | 2.6156 | 0.0091 | 0.0297 |
| 4.2947 | 0.0015 | 2.6426 | 0.0078 | 0.0269 | 3.4672 | 0.1802 | 2.6562 | 0.0030 | 0.0286 |
| 3.6570 | −0.1946 | 2.6553 | 0.0022 | 0.0260 | 0.6926 | 1.0070 | 2.6504 | 0.0032 | 0.0281 |
| 2.0640 | −1.0652 | 2.6667 | 0.0000 | 0.0275 | −1.0279 | 1.6243 | 2.6679 | −0.0009 | 0.0280 |
| −0.7516 | 0.4895 | 2.6517 | 0.0082 | 0.0276 | 1.7556 | 1.6055 | 2.6504 | −0.0061 | 0.0271 |
| 0.4696 | 1.1510 | 2.6595 | 0.0149 | 0.0259 | 2.6656 | 1.1491 | 2.6465 | 0.0055 | 0.0268 |
| 2.6135 | 0.1354 | 2.6603 | 0.0198 | 0.0257 | 1.8804 | 0.0489 | 2.6578 | 0.0094 | 0.0269 |
| 2.2015 | 0.8717 | 2.6764 | 0.0234 | 0.0252 | 1.4364 | 2.4511 | 2.6424 | 0.0147 | 0.0274 |
| −1.5877 | 1.0282 | 2.6433 | 0.0265 | 0.0257 | −0.8869 | 0.3706 | 2.6553 | 0.0233 | 0.0270 |
| 1.0911 | 0.9549 | 2.6383 | 0.0156 | 0.0273 | 3.8185 | 1.4745 | 2.6374 | 0.0212 | 0.0270 |

TABLE 2-continued

| | | | | | | | | | |
|---|---|---|---|---|---|---|---|---|---|
| 0.6405 | 1.0707 | 2.6269 | 9.0109 | 0.0263 | 5.2580 | 1.9862 | 2.6505 | 0.0093 | 0.0262 |
| 2.9855 | −0.7376 | 2.6400 | 0.0163 | 0.0257 | 5.5363 | 2.1272 | 2.6450 | 0.0131 | 0.0280 |
| −0.0792 | 1.2066 | 2.6596 | 0.0127 | 0.0276 | 3.9680 | −0.8128 | 2.6595 | 0.0179 | 0.0283 |
| 1.5000 | 1.4515 | 2.6480 | 0.0080 | 0.0264 | 5.6487 | −0.0307 | 2.6388 | 0.0154 | 0.0272 |
| 2.0032 | 0.7530 | 2.6395 | 0.0168 | 0.0278 | 5.0248 | −0.0490 | 2.6583 | 0.0148 | 0.0274 |
| 1.9438 | 0.7470 | 2.6441 | 0.0142 | 0.0285 | 3.7343 | 0.2521 | 2.6457 | 0.0151 | 0.0266 |
| 1.7779 | 0.3329 | 2.6504 | 0.0194 | 0.0268 | 3.8525 | −0.5475 | 2.6409 | 0.0073 | 0.0257 |
| 0.9317 | 0.7055 | 2.6594 | 0.0105 | 0.0270 | 1.9750 | −0.3080 | 2.6590 | 0.0064 | 0.0262 |
| 1.1448 | −0.2698 | 2.6541 | 0.0151 | 0.0282 | 2.4254 | 1.0970 | 2.6212 | 0.0087 | 0.0260 |
| 1.2180 | 0.6105 | 2.6346 | 0.0179 | 0.0277 | 4.1537 | −0.6771 | 2.6481 | 0.0042 | 0.0261 |
| 2.7756 | 0.5979 | 2.6384 | 0.0193 | 0.0273 | 4.0032 | −0.2603 | 2.6420 | 0.0112 | 0.0273 |
| 2.5161 | 1.5493 | 2.6370 | 0.0229 | 0.0289 | 1.4932 | −0.1021 | 2.6441 | 0.0090 | 0.0269 |
| 2.0964 | 1.3332 | 2.6481 | 0.0182 | 0.0292 | 0.7664 | 0.8529 | 2.6720 | 0.0071 | 0.0257 |
| 3.3333 | 0.5501 | 2.6349 | 0.0138 | 0.0289 | −0.4797 | 0.5068 | 2.6669 | −0.0005 | 0.0255 |
| 1.7608 | −0.0067 | 2.6443 | 0.0091 | 0.0278 | 0.7154 | −0.3132 | 2.6348 | 0.0173 | 0.0257 |
| 3.1357 | 0.1307 | 2.6615 | 0.0069 | 0.0286 | 3.2984 | −0.3120 | 2.6519 | 0.0163 | 0.0269 |
| 3.8387 | −0.4405 | 2.6716 | 0.0088 | 0.0279 | 1.8484 | 0.4275 | 2.6477 | 0.0043 | 0.0255 |
| 1.3406 | −0.5397 | 2.6671 | 0.0016 | 0.0285 | 4.1122 | 0.6229 | 2.6526 | 0.0127 | 0.0267 |
| 2.2098 | 0.0681 | 2.6647 | −0.0018 | 0.0283 | 5.4264 | 0.5311 | 2.6629 | 0.0144 | 0.0270 |
| 3.0657 | 1.2731 | 2.6360 | 0.0077 | 0.0280 | 2.4485 | −0.1950 | 2.6318 | 0.0194 | 0.0271 |
| 1.6042 | 0.4607 | 2.6518 | 0.0135 | 0.0275 | 1.6210 | 0.0260 | 2.6433 | 0.0204 | 0.0264 |
| 1.3719 | −0.1883 | 2.6379 | 0.0151 | 0.0283 | 1.5463 | 0.5455 | 2.6639 | 0.0197 | 0.0271 |
| 1.7340 | −0.1611 | 2.6531 | 0.0091 | 0.0290 | −0.4220 | 1.5365 | 2.6584 | 0.0126 | 0.0266 |
| 3.6180 | 0.0326 | 2.6556 | 0.0086 | 0.0277 | 1.0062 | 0.8841 | 2.6742 | 0.0045 | 0.0269 |
| 2.8489 | −0.6367 | 2.6569 | 0.0108 | 0.0263 | 0.0555 | 2.7342 | 2.6609 | 0.0119 | 0.0281 |
| 3.1276 | −0.4529 | 2.6696 | 0.0063 | 0.0254 | 2.9193 | 0.9645 | 2.6589 | 0.0181 | 0.0283 |
| 2.6245 | 0.2364 | 2.6566 | −0.0013 | 0.0258 | 0.6911 | 1.4240 | 2.6691 | 0.0118 | 0.0290 |
| −0.5746 | 0.8892 | 2.6583 | 0.0066 | 0.0247 | 2.4935 | 1.7796 | 2.6704 | 0.0163 | 0.0289 |
| 0.9890 | 0.6048 | 2.6551 | 0.0090 | 0.0263 | 2.8286 | −0.3854 | 2.6436 | 0.0077 | 0.0280 |
| 0.9238 | 0.9183 | 2.6311 | 0.0160 | 0.0258 | 1.7800 | −0.7078 | 2.6339 | 0.0070 | 0.0282 |
| 0.7355 | 0.7216 | 2.6647 | 0.0058 | 0.0271 | 4.7955 | 0.0432 | 2.6554 | 0.0076 | 0.0273 |
| 1.4604 | −0.0277 | 2.6728 | 0.0017 | 0.0270 | 4.6393 | −0.1269 | 2.6395 | 0.0112 | 0.0280 |
| 2.7630 | −0.8205 | 2.6541 | 0.0125 | 0.0274 | 3.5125 | 0.6930 | 2.6470 | 0.0095 | 0.0285 |
| 0.6435 | 1.0916 | 2.6615 | 0.0099 | 0.0277 | 3.3619 | 0.9445 | 2.6362 | 0.0111 | 0.0267 |
| 0.2236 | 0.5965 | 2.6344 | 0.0089 | 0.0279 | 3.1334 | 0.1944 | 2.6714 | 0.0139 | 0.0266 |
| 5.1111 | −0.5296 | 2.6426 | 0.0100 | 0.0279 | 4.7833 | −0.0917 | 2.6557 | 0.0185 | 0.0269 |
| 3.4684 | −0.0110 | 2.6269 | 0.0209 | 0.0271 | 5.4401 | −0.2506 | 2.6651 | 0.0073 | 0.0269 |
| 2.9153 | 0.4338 | 2.6587 | 0.0023 | 0.0274 | 5.4735 | 2.8194 | 2.6573 | 0.0185 | 0.0264 |
| 4.3987 | −0.1074 | 2.6456 | 0.0091 | 0.0262 | 5.5550 | 1.5283 | 2.6546 | 0.0205 | 0.0274 |
| 5.6390 | 0.1259 | 2.6831 | −0.0002 | 0.0276 | 2.4647 | −0.4182 | 2.6326 | 0.0197 | 0.0264 |
| 4.6234 | −0.3685 | 2.6617 | 0.0139 | 0.0270 | 2.5947 | 0.4348 | 2.6398 | 0.0166 | 0.0257 |
| 3.2167 | 0.4303 | 2.6669 | 0.0149 | 0.0269 | 5.2601 | −0.8030 | 2.6339 | 0.0165 | 0.0259 |
| −0.9947 | 1.1790 | 2.6456 | 0.0254 | 0.0269 | 1.5620 | −0.3957 | 2.6557 | 0.0112 | 0.0267 |
| 0.0510 | −0.6717 | 2.6522 | 0.0140 | 0.0279 | 3.1886 | 0.6717 | 2.6597 | 0.0152 | 0.0269 |
| 1.5499 | 0.7653 | 2.6556 | 0.0064 | 0.0275 | 2.3172 | 0.3351 | 2.6519 | 0.0128 | 0.0279 |
| 2.7515 | 0.2621 | 2.6417 | 0.0159 | 0.0276 | 1.7145 | 0.2908 | 2.6705 | 0.0150 | 0.0264 |
| 2.1329 | 0.3001 | 2.6537 | 0.0118 | 0.0287 | 0.4832 | 0.8634 | 2.6331 | 0.0134 | 0.0268 |
| 0.1038 | −0.2650 | 2.6599 | 0.0121 | 0.0301 | 1.6046 | 0.6050 | 2.6525 | 0.0161 | 0.0263 |
| 0.5497 | −0.1902 | 2.6464 | 0.0126 | 0.0295 | 1.4801 | −0.4843 | 2.6308 | 0.0132 | 0.0272 |
| 4.5646 | 0.6390 | 2.6392 | 0.0122 | 0.0310 | 3.8580 | −0.1407 | 2.6456 | 0.0123 | 0.0272 |
| 4.6423 | −0.2855 | 2.6483 | 0.0051 | 0.0305 | 2.8298 | −0.3796 | 2.6697 | 0.0114 | 0.0280 |
| 0.9757 | 0.1570 | 2.6571 | 0.0010 | 0.0280 | 4.5972 | 0.1429 | 2.6608 | 0.0088 | 0.0270 |
| −0.1634 | 1.7612 | 2.6548 | 0.0040 | 0.0273 | 4.1364 | −1.1916 | 2.6492 | 0.0112 | 0.0274 |
| 5.7496 | −0.0144 | 2.6629 | 0.0036 | 0.0276 | 6.0897 | −0.3205 | 2.6577 | 0.0059 | 0.0277 |
| 4.0844 | 2.4526 | 2.6451 | 0.0139 | 0.0278 | 4.9552 | −0.4364 | 2.6544 | 0.0039 | 0.0267 |
| 1.5898 | 0.4142 | 2.6526 | 0.0097 | 0.0297 | 3.1637 | 1.1782 | 2.6379 | 0.0215 | 0.0278 |
| 5.8530 | −0.6858 | 2.6609 | 0.0158 | 0.0297 | 6.3351 | 0.0659 | 2.6617 | 0.0043 | 0.0278 |
| 1.4526 | −0.0266 | 2.6490 | 0.0165 | 0.0294 | 3.5044 | −0.1156 | 2.6606 | 0.0094 | 0.0281 |
| 4.8247 | −0.4467 | 2.6727 | 0.0086 | 0.0285 | 4.9274 | 0.1780 | 2.6799 | 0.0167 | 0.0274 |
| 2.2071 | 0.7735 | 2.6637 | 0.0101 | 0.0280 | 2.8589 | 0.0766 | 2.6408 | 0.0165 | 0.0268 |
| 2.7602 | −1.1441 | 2.6728 | 0.0041 | 0.0277 | 7.0296 | 1.2237 | 3.6407 | 0.0180 | 0.0279 |
| 4.7296 | −0.3192 | 2.6857 | 0.0073 | 0.0269 | 6.1476 | −0.6054 | 2.6320 | 0.0229 | 0.0284 |
| 3.9752 | −0.0634 | 2.6399 | 0.0117 | 0.0286 | 0.0807 | 0.5775 | 2.6322 | 0.0250 | 0.0270 |
| 3.9231 | −0.6048 | 2.6313 | 0.0151 | 0.0275 | −0.4210 | 2.3943 | 2.6508 | 0.0167 | 0.0278 |
| 0.1038 | 1.8569 | 2.6337 | 0.0168 | 0.0276 | 0.8421 | 0.9277 | 2.6254 | 0.0179 | 0.0275 |
| −0.3743 | 0.0590 | 2.6449 | 0.0156 | 0.0284 | 0.2053 | 0.7711 | 2.6525 | 0.0160 | 0.0275 |
| 1.3266 | 0.9062 | 2.6504 | 0.0048 | 0.0291 | 1.5198 | 0.1395 | 2.6589 | 0.0171 | 0.0280 |
| 0.4070 | 1.0268 | 2.6473 | 0.0026 | 0.0300 | 4.5912 | 0.1663 | 2.6604 | 0.0181 | 0.0266 |
| 5.6739 | 0.4286 | 2.6676 | −0.0078 | 0.0288 | −0.4122 | 0.9031 | 2.6257 | 0.0116 | 0.0264 |
| 3.1987 | −0.5687 | 2.6523 | 0.0017 | 0.0294 | 0.1565 | 0.8077 | 2.6332 | 0.0139 | 0.0257 |
| 3.6794 | 0.0599 | 2.6551 | 0.0038 | 0.0303 | 3.3031 | 0.3603 | 2.6571 | 0.0053 | 0.0264 |
| 1.2408 | −0.3776 | 2.6497 | 0.0119 | 0.0278 | 0.6351 | 0.1792 | 2.6524 | 0.0166 | 0.0270 |
| −0.9869 | 0.4009 | 2.6605 | 0.0054 | 0.0288 | 3.6102 | 0.2737 | 2.6501 | 0.0126 | 0.0283 |
| 0.6435 | 0.2305 | 2.6629 | 0.0201 | 0.0309 | 0.5728 | 0.6886 | 2.6348 | 0.0062 | 0.0272 |
| 5.0394 | −0.2060 | 2.6576 | 0.0221 | 0.0287 | 3.9223 | 1.4700 | 2.6556 | 0.0097 | 0.0267 |
| 1.1285 | −0.2338 | 2.6583 | 0.0239 | 0.0293 | 2.5091 | 0.2165 | 2.6402 | 0.0126 | 0.0280 |
| 0.1576 | 0.2951 | 2.6702 | 0.0187 | 0.0294 | 1.3408 | −0.1985 | 2.6570 | 0.0134 | 0.0282 |
| 1.2466 | −0.8176 | 2.6792 | 0.0064 | 0.0278 | 1.6198 | 0.1106 | 2.6468 | 0.0109 | 0.0302 |
| 2.4576 | −0.0801 | 2.6384 | 0.0149 | 0.0279 | 0.7543 | 1.4660 | 2.6470 | 0.0075 | 0.0293 |

TABLE 2-continued

| | | | | | | | | | |
|---|---|---|---|---|---|---|---|---|---|
| 1.4351 | 0.4720 | 2.6417 | 0.0074 | 0.0276 | −0.4623 | 1.3366 | 2.6568 | 0.0090 | 0.0282 |
| 2.1705 | 0.7970 | 2.6685 | 0.0061 | 0.0272 | 2.2284 | 0.1388 | 2.6479 | 0.0115 | 0.0295 |
| 1.9753 | 0.9815 | 2.6747 | −0.0042 | 0.0279 | 2.4779 | −0.0747 | 2.6465 | 0.0072 | 0.0287 |
| 1.6634 | 1.7689 | 2.6589 | −0.0032 | 0.0279 | 2.8892 | −0.1678 | 2.6614 | 0.0001 | 0.0298 |
| 1.8753 | 0.2988 | 2.6652 | −0.0010 | 0.0290 | 1.9326 | 0.4626 | 2.6585 | 0.0060 | 0.0297 |
| 2.2568 | 0.4001 | 2.6539 | 0.0113 | 0.0285 | 1.7998 | −0.1421 | 2.6406 | 0.0114 | 0.0291 |
| 1.0899 | 0.8312 | 2.6361 | 0.0214 | 0.0292 | 5.3151 | 1.3082 | 2.6542 | 0.0167 | 0.0312 |
| 1.3405 | 0.4510 | 2.6207 | 0.0219 | 0.0285 | 3.7844 | 0.7163 | 2.6363 | 0.0140 | 0.0300 |
| 2.2616 | 1.2187 | 2.6580 | 0.0217 | 0.0275 | 3.9901 | −0.2761 | 2.6304 | 0.0121 | 0.0301 |
| 2.4213 | 0.2571 | 2.6402 | 0.0222 | 0.0268 | 3.8605 | 0.0214 | 2.6637 | 0.0103 | 0.0292 |
| 1.8040 | 0.0648 | 2.6410 | 0.0242 | 0.0271 | 3.0661 | 0.5508 | 2.6379 | 0.0164 | 0.0295 |
| 3.1152 | 0.5659 | 2.6365 | 0.0180 | 0.0265 | 2.7208 | −0.0203 | 2.6344 | 0.0212 | 0.0282 |
| 2.0584 | −0.3071 | 2.6531 | 0.0144 | 0.0269 | 0.9973 | −0.4140 | 2.6360 | 0.0146 | 0.0284 |
| 2.4829 | 0.1583 | 2.6540 | 0.0133 | 0.0280 | 0.7763 | −0.3762 | 2.6833 | 0.0106 | 0.0276 |
| 3.0716 | 0.3409 | 2.6455 | 0.0271 | 0.0273 | 1.0342 | −0.5092 | 2.6487 | 0.0195 | 0.0277 |
| 2.2086 | −0.0405 | 2.6562 | 0.0186 | 0.0279 | 4.2957 | 0.5439 | 2.6624 | 0.0202 | 0.0280 |
| 1.2647 | −0.2818 | 2.6556 | 0.0214 | 0.0276 | 1.7571 | 0.0614 | 2.6254 | 0.0325 | 0.0282 |
| −0.3120 | 0.3237 | 2.6677 | 0.0245 | 0.0289 | 1.9995 | 0.0862 | 2.6187 | 0.0271 | 0.0269 |
| 1.1265 | −0.4772 | 2.6579 | 0.0230 | 0.0290 | 2.8816 | −0.2495 | 2.6516 | 0.0252 | 0.0258 |
| 6.2250 | −0.6330 | 2.6542 | 0.0210 | 0.0287 | 3.3942 | 0.9311 | 2.6274 | 0.0290 | 0.0268 |
| 3.4051 | −0.4863 | 2.6628 | 0.0152 | 0.0292 | 5.1002 | 2.1636 | 2.6527 | 0.0221 | 0.0277 |
| 5.6163 | −1.0273 | 2.6541 | 0.0062 | 0.0287 | 3.3126 | 1.0240 | 2.6503 | 0.0151 | 0.0279 |
| 3.9738 | −0.9201 | 2.6504 | 0.0116 | 0.0286 | 5.0856 | 0.7651 | 2.6439 | 0.0074 | 0.0278 |
| 3.5216 | −0.1981 | 2.6332 | 0.0123 | 0.0282 | 2.6226 | 0.2481 | 2.6559 | 0.0038 | 0.0278 |
| 3.8687 | 0.2983 | 2.6756 | 0.0079 | 0.0291 | 2.4993 | −0.8425 | 2.6341 | 0.0149 | 0.0279 |
| 2.7837 | 0.1007 | 2.6690 | 0.0009 | 0.0275 | 2.3059 | −0.1236 | 2.6576 | 0.0082 | 0.0277 |
| 3.7486 | −0.1015 | 2.6623 | 0.0039 | 0.0269 | 1.9314 | 1.1583 | 2.6462 | 0.9043 | 0.0272 |
| 4.4130 | −0.0950 | 2.6493 | 0.0039 | 0.0284 | 4.1432 | 1.4166 | 2.6461 | 0.0101 | 0.0275 |
| 3.3456 | 1.0716 | 2.6524 | 0.0088 | 0.0275 | 1.4722 | 0.7197 | 2.6469 | 0.0095 | 0.0275 |
| 5.7458 | 2.1661 | 2.6535 | 0.0124 | 0.0292 | 1.7396 | 1.1944 | 2.6630 | −0.0031 | 0.0276 |
| 3.6741 | 1.4704 | 2.6537 | 0.0095 | 0.0265 | 0.5433 | 1.1531 | 2.6608 | 0.0088 | 0.0273 |
| 4.6054 | −1.1951 | 2.6563 | 0.0055 | 0.0261 | 1.1114 | 0.7466 | 2.6562 | 0.0065 | 0.0272 |
| 0.7481 | 0.0589 | 2.6654 | 0.0098 | 0.0279 | 2.3006 | −0.3401 | 2.6557 | 0.0064 | 0.0290 |
| 2.4971 | 0.2204 | 2.6502 | 0.0065 | 0.0283 | 1.5934 | −0.4329 | 2.6604 | 0.0098 | 0.0282 |
| 5.1444 | 0.9360 | 2.6723 | 0.0049 | 0.0285 | 3.9484 | 0.7024 | 2.6592 | 0.0119 | 0.0291 |
| 1.0513 | 0.2423 | 2.6576 | 0.0113 | 0.0273 | 1.7271 | 0.2438 | 2.6493 | 0.0153 | 0.0297 |
| 3.5246 | −1.2707 | 2.6480 | 0.0076 | 0.0270 | 1.3154 | 0.4531 | 2.6514 | 0.0165 | 0.0300 |
| 2.0580 | −0.7626 | 2.6468 | 0.0014 | 0.0277 | 0.7342 | −0.3904 | 2.6370 | 0.0187 | 0.0303 |
| 5.3037 | 0.9284 | 2.6547 | 0.0049 | 0.0271 | 4.0921 | 0.9674 | 2.6481 | 0.0129 | 0.0295 |
| 1.6737 | −1.8800 | 2.6520 | 0.0104 | 0.0276 | 2.0202 | 0.5530 | 2.6550 | 0.0187 | 0.0301 |
| 1.6756 | −0.2589 | 2.6692 | 0.0122 | 0.0251 | 5.0239 | 1.2197 | 2.6395 | 0.0243 | 0.0273 |
| 1.8537 | 0.2308 | 2.6348 | 0.0042 | 0.0259 | 1.9182 | 2.1497 | 2.6625 | 0.0193 | 0.0298 |
| 2.7548 | 0.7253 | 2.6493 | 0.0049 | 0.0261 | 1.5489 | −0.0431 | 2.6333 | 0.0167 | 0.0281 |
| 7.3168 | 1.7221 | 2.6681 | 0.0062 | 0.0271 | 2.8078 | 0.4778 | 2.6564 | 0.0168 | 0.0277 |
| 1.0909 | −0.7174 | 2.6533 | −0.0025 | 0.0287 | 2.4542 | 1.6889 | 2.6469 | 0.0178 | 0.0278 |
| 3.4638 | 0.7847 | 2.6681 | 0.0004 | 0.0290 | 5.4741 | 0.6723 | 2.6520 | 0.0125 | 0.0292 |
| 1.1741 | 0.0114 | 2.6588 | −0.0001 | 0.0286 | 4.4518 | 0.4794 | 2.6424 | 0.0144 | 0.0280 |
| 0.1926 | 0.6597 | 2.6373 | 0.0062 | 0.0282 | 0.4142 | 0.5643 | 2.6588 | 0.0126 | 0.0273 |
| 0.2074 | −0.4174 | 2.6659 | −0.0013 | 0.0276 | 1.2884 | −0.7911 | 2.6616 | 0.0128 | 0.0269 |
| 0.7082 | 0.3006 | 2.6438 | 0.0066 | 0.0271 | 2.9510 | 0.8399 | 2.6462 | 0.0138 | 0.0280 |
| 2.1632 | 0.8803 | 2.6584 | 0.0134 | 0.0264 | 5.2756 | 0.3397 | 2.6589 | 0.0197 | 0.0269 |
| 1.6452 | 0.4779 | 2.6495 | 0.0122 | 0.0273 | 5.1139 | −0.1901 | 2.6353 | 0.0131 | 0.0269 |
| 2.5861 | 0.5153 | 2.6494 | 0.0133 | 0.0274 | 5.4041 | 0.1544 | 2.6249 | 0.0121 | 0.0270 |
| 0.5588 | 0.6602 | 2.6316 | 0.0112 | 0.0287 | 2.8549 | 0.2004 | 2.6529 | 0.0146 | 0.0276 |
| 1.1702 | 0.3383 | 2.6569 | 0.0036 | 0.0290 | 2.4040 | 0.0839 | 2.6491 | 0.0166 | 0.0282 |
| 1.8428 | −0.6746 | 2.6294 | 0.0147 | 0.0293 | 0.9641 | 0.0309 | 2.6671 | 0.0032 | 0.0272 |
| 1.2379 | −0.5478 | 2.6402 | 0.0103 | 0.0271 | 2.1573 | 0.2211 | 2.6359 | −0.0003 | 0.0273 |
| 2.7566 | 0.1735 | 2.6431 | 0.0125 | 0.0263 | 2.4766 | −0.6345 | 2.6505 | 0.0095 | 0.0284 |
| 5.2023 | −0.2589 | 2.6506 | 0.0105 | 0.0269 | 2.3514 | 0.4033 | 2.6646 | 0.0150 | 0.0281 |
| 1.4437 | 0.3557 | 2.6452 | 0.0104 | 0.0274 | 0.4769 | −0.2424 | 2.6387 | 0.0035 | 0.0260 |
| 3.2293 | 0.3061 | 2.6765 | 0.0059 | 0.0268 | 1.3173 | −0.7170 | 2.6517 | 0.0106 | 0.0271 |
| 0.3389 | 0.6234 | 2.6455 | 0.0093 | 0.0292 | 2.4949 | 1.0255 | 2.6577 | 0.0097 | 0.0288 |
| −0.6021 | 0.7865 | 2.6506 | 0.0058 | 0.0290 | 0.3930 | 2.1710 | 2.6455 | 0.0148 | 0.0290 |
| 0.2341 | 0.4654 | 2.6628 | 0.0084 | 0.0288 | 2.8404 | −0.1583 | 2.6599 | 0.0060 | 0.0278 |
| −1.6390 | −0.2941 | 2.6570 | 0.0105 | 0.0290 | 0.6899 | 1.1045 | 2.6533 | 0.0058 | 0.0284 |
| 1.6630 | 0.4140 | 2.6576 | 0.0163 | 0.0282 | 1.8179 | −0.5589 | 2.6658 | 0.0091 | 0.0276 |
| −1.4057 | 0.9888 | 2.6432 | 0.0159 | 0.0266 | 2.6599 | −0.8348 | 2.6673 | 0.0088 | 0.0274 |
| −0.0411 | 1.4645 | 2.6661 | 0.0093 | 0.0277 | 4.4094 | 0.0391 | 2.6685 | 0.0073 | 0.0259 |
| 2.9795 | 0.5006 | 2.6626 | 0.0131 | 0.0273 | 3.1961 | 0.8577 | 2.6224 | 0.0120 | 0.0280 |
| 5.5393 | 1.7395 | 2.6454 | 0.0186 | 0.0272 | 2.5163 | 0.5533 | 2.6263 | 0.0197 | 0.0293 |
| 4.1986 | −1.2595 | 2.6344 | 0.0184 | 0.0262 | 2.3859 | 1.0875 | 2.6658 | 0.0086 | 0.0283 |
| 3.7823 | −0.6545 | 2.6596 | 0.0133 | 0.0273 | 1.4727 | 1.2611 | 2.6517 | 0.0034 | 0.0267 |
| 1.6472 | −0.6402 | 2.6404 | 0.0239 | 0.0279 | 3.2515 | 0.9088 | 2.6442 | 0.0182 | 0.0267 |
| 6.5593 | 1.1958 | 2.6463 | 0.0222 | 0.0284 | 4.5539 | 1.0301 | 2.6465 | 0.0206 | 0.0276 |
| 3.6094 | 1.5731 | 2.6440 | 0.0096 | 0.0295 | 5.9524 | 0.4144 | 2.6449 | 0.0184 | 0.0277 |
| 3.7812 | 2.1883 | 2.6481 | 0.0044 | 0.0290 | 6.1258 | 0.3042 | 2.6620 | 0.0122 | 0.0286 |
| 4.4263 | 1.8294 | 2.6459 | 0.0057 | 0.0283 | 6.6355 | −0.5733 | 2.6144 | 0.8196 | 0.0271 |
| 4.9112 | 3.0428 | 2.6458 | 0.0099 | 0.0288 | 4.4364 | −0.0096 | 2.6472 | 0.0195 | 0.0265 |
| 2.7827 | 2.6269 | 2.6308 | 0.0190 | 0.0294 | 3.3822 | 0.4706 | 2.6532 | 0.0124 | 0.0280 |

TABLE 2-continued

| | | | | | | | | | |
|---|---|---|---|---|---|---|---|---|---|
| 4.1157 | −0.2270 | 2.6573 | 0.0071 | 0.0274 | −0.5750 | 0.4658 | 2.6536 | 0.0122 | 0.0280 |
| 2.5359 | 1.6700 | 2.6441 | 0.0143 | 0.0281 | −1.4322 | 1.2392 | 2.6708 | 0.0037 | 0.0274 |
| 2.4012 | 0.1917 | 2.6431 | 0.0034 | 0.0267 | 2.1764 | 1.1806 | 2.6670 | 0.0032 | 0.0276 |
| 4.8764 | −0.6363 | 2.6352 | 0.0048 | 0.0273 | 0.4389 | 0.9985 | 2.6450 | 0.0080 | 0.0276 |
| 1.0126 | −0.3540 | 2.6516 | −0.0053 | 0.0272 | −2.3457 | 0.7739 | 2.6617 | 0.0074 | 0.0269 |
| 1.3119 | −0.6050 | 2.6786 | −0.0028 | 0.0277 | −0.2867 | 0.4845 | 2.6613 | −0.0071 | 0.0279 |
| 2.5003 | −0.4723 | 2.6399 | 0.0055 | 0.0280 | −0.3643 | 0.5095 | 2.6407 | −0.0178 | 0.0273 |
| 2.0027 | 0.3019 | 2.6597 | 0.0087 | 0.0282 | −0.0560 | 0.3752 | 2.6588 | 0.0007 | 0.0283 |
| 1.4444 | −0.0958 | 2.6602 | 0.0109 | 0.0278 | 3.9491 | 0.1921 | 2.6622 | 0.0067 | 0.0278 |
| 4.5706 | 0.6752 | 2.6332 | 0.0218 | 0.0269 | 3.4450 | 0.4169 | 2.6443 | 0.0027 | 0.0276 |
| 1.4238 | 0.3784 | 2.6345 | 0.0229 | 0.0284 | 3.6594 | −0.1030 | 2.6640 | 0.0167 | 0.0278 |
| 2.6803 | −0.4080 | 2.6470 | 0.0205 | 0.0303 | 3.6901 | 0.7143 | 2.6462 | 0.0137 | 0.0266 |
| 3.2681 | 0.3190 | 2.6302 | 0.0234 | 0.0280 | 3.5109 | 1.1141 | 2.6585 | 0.0083 | 0.0262 |
| 4.4241 | 0.9761 | 2.6497 | 0.0220 | 0.0271 | 3.2343 | 0.7636 | 2.6690 | 0.0129 | 0.0266 |
| 6.9269 | 1.2038 | 2.6470 | 0.0137 | 0.0263 | 1.9397 | 0.4829 | 2.6602 | 0.0111 | 0.0275 |
| 4.7181 | 0.7996 | 2.6314 | 0.0177 | 0.0274 | 2.2792 | 0.3657 | 2.6454 | 0.0152 | 0.0272 |
| 3.6084 | −0.2809 | 2.6387 | 0.0123 | 0.0286 | 2.3775 | −0.5988 | 2.6671 | 0.0178 | 0.0275 |
| 0.9427 | 0.1676 | 2.6629 | 0.0082 | 0.0274 | 2.0547 | −0.0878 | 2.6387 | 0.0192 | 0.0282 |
| 2.4099 | 0.4064 | 2.6317 | 0.0104 | 0.0270 | 1.0545 | 0.0378 | 2.6475 | 0.0141 | 0.0292 |
| 1.0040 | 0.2873 | 2.6521 | 0.0081 | 0.0271 | 1.3411 | 0.1699 | 2.6475 | 0.0165 | 0.0281 |
| 0.5834 | 0.3950 | 2.6499 | 0.0027 | 0.0285 | 2.6481 | −0.4131 | 2.6468 | 0.0163 | 0.0272 |
| 1.6207 | −0.1592 | 2.6608 | 0.0076 | 0.0288 | 4.6923 | 0.4920 | 2.6248 | 0.0195 | 0.0260 |
| 4.0428 | −0.3196 | 2.6460 | 0.0045 | 0.0289 | 3.1451 | 0.2122 | 2.6667 | 0.0130 | 0.0261 |
| 2.1667 | −0.4218 | 2.6241 | 0.0025 | 0.0286 | 3.8535 | 2.6115 | 2.6649 | 0.0093 | 0.0253 |
| 3.6067 | 0.4782 | 2.6547 | 0.0041 | 0.0278 | 4.1541 | −0.0261 | 2.6542 | 0.0079 | 0.0262 |
| 1.9123 | 0.3994 | 2.6453 | 0.0121 | 0.0283 | 4.0195 | 1.1967 | 2.6624 | 0.0104 | 0.0279 |
| 3.8838 | −0.4143 | 2.6584 | 0.0088 | 0.0286 | 2.2126 | 0.7001 | 2.6676 | 0.0150 | 0.0280 |
| 2.1482 | −0.3200 | 2.6503 | 0.0193 | 0.0294 | 1.4314 | −0.3612 | 2.6465 | 0.0129 | 0.0275 |
| 2.7011 | −0.1556 | 2.6488 | 0.0186 | 0.0288 | 0.2025 | 1.5073 | 2.6473 | 0.0084 | 0.0277 |
| 3.0142 | 1.7930 | 2.6649 | 0.0125 | 0.0269 | 1.5765 | −0.4884 | 2.6270 | 0.0167 | 0.0266 |
| 2.0626 | −0.2325 | 2.6486 | 0.0145 | 0.0266 | 2.6630 | −0.3758 | 2.6378 | 0.0156 | 0.0270 |
| 1.3075 | 0.0367 | 2.6419 | 0.0203 | 0.0275 | 5.1488 | −0.1241 | 2.6533 | 0.0221 | 0.0280 |
| 3.2476 | −0.5700 | 2.6382 | 0.0236 | 0.0277 | 5.6596 | −0.3814 | 2.6444 | 0.0216 | 0.0278 |
| 4.8414 | −0.4105 | 2.6651 | 0.0172 | 0.0284 | 5.4980 | −0.6379 | 2.6626 | 0.0199 | 0.0283 |
| 2.1621 | 0.0915 | 2.6599 | 0.0131 | 0.0282 | 3.0443 | 0.5816 | 2.6492 | 0.0168 | 0.0281 |
| 3.9532 | 0.3748 | 2.6817 | 0.0049 | 0.0277 | 2.6895 | −0.1860 | 2.6437 | 0.0183 | 0.0270 |
| 1.9418 | −0.0814 | 2.6667 | 0.0076 | 0.0281 | 1.7831 | −0.9372 | 2.6652 | 0.0115 | 0.0261 |
| 2.6563 | 0.5933 | 2.6197 | 0.0131 | 0.0274 | 3.8252 | 0.2824 | 2.6552 | 0.0180 | 0.0262 |
| 2.8363 | 0.2643 | 2.6462 | 0.0183 | 0.0268 | 2.9598 | 0.2530 | 2.6620 | 0.0123 | 0.0260 |
| 0.5135 | 0.5905 | 2.6694 | 0.0127 | 0.0277 | 1.8252 | 0.6973 | 2.6502 | 0.0085 | 0.0263 |
| 5.2928 | 0.6642 | 2.6624 | 0.0111 | 0.0272 | 2.4287 | 0.6812 | 2.6900 | 0.0063 | 0.0264 |
| 1.7432 | 0.2334 | 2.6577 | 0.0169 | 0.0273 | 5.0761 | 1.8561 | 2.6568 | 0.0159 | 0.0272 |
| 3.4760 | 0.6209 | 2.6478 | 0.0132 | 0.0282 | 0.4468 | 0.3913 | 2.6383 | 0.0281 | 0.0277 |
| 0.7206 | 0.6170 | 2.6557 | 0.0170 | 0.0272 | 2.9688 | 0.5846 | 2.6603 | 0.0165 | 0.0283 |
| −0.2979 | 0.0385 | 2.6415 | 0.0174 | 0.0275 | 3.9400 | 1.4588 | 2.6787 | 0.0112 | 0.0268 |
| 2.6450 | 0.3160 | 2.6622 | 0.0165 | 0.0276 | 2.4346 | 1.2917 | 2.6565 | 0.0122 | 0.0269 |
| 3.0699 | 0.4915 | 2.6527 | 0.0214 | 0.0270 | 1.5787 | 1.0159 | 2.6455 | 0.0093 | 0.0270 |
| 2.4165 | 0.4811 | 2.6536 | 0.0196 | 0.0291 | −0.5695 | 1.0801 | 2.6330 | 0.0252 | 0.0274 |
| 1.8736 | 1.5841 | 2.6406 | 0.0131 | 0.0288 | −0.3294 | 1.0115 | 2.6532 | 0.0284 | 0.0268 |
| 3.6034 | 2.0621 | 2.6645 | 0.0154 | 0.0278 | 3.3528 | 2.7957 | 2.6434 | 0.0316 | 0.0264 |
| 4.2998 | −0.0787 | 2.6480 | 0.0200 | 0.0276 | −0.0093 | 0.8596 | 2.6430 | 0.0164 | 0.0256 |
| 3.9555 | −0.1884 | 2.6409 | 0.0226 | 0.0292 | 2.0246 | 0.6432 | 2.6418 | 0.0099 | 0.0266 |
| 0.9139 | −0.5540 | 2.6455 | 0.0180 | 0.0284 | 4.5836 | 1.4561 | 2.6522 | 0.0088 | 0.0285 |
| 2.1694 | 0.1378 | 2.6475 | 0.0088 | 0.0272 | 3.2806 | −0.2098 | 2.6533 | 0.0053 | 0.0275 |
| 1.7707 | −0.2607 | 2.6234 | 0.0071 | 0.0279 | 2.7829 | 0.0721 | 2.6382 | 0.0068 | 0.0286 |
| 0.9334 | 0.2441 | 2.6775 | 0.0052 | 0.0298 | 1.6528 | 1.0183 | 2.6706 | 0.0065 | 0.0295 |
| 3.6275 | 0.5285 | 2.6454 | 0.0178 | 0.0289 | 4.1942 | −0.8104 | 2.6520 | 0.0119 | 0.0315 |
| 1.4500 | 0.1172 | 2.6353 | 0.0211 | 0.0277 | 2.0121 | −0.4914 | 2.6409 | −0.0008 | 0.0304 |
| 1.4600 | 0.4299 | 2.6527 | 0.0177 | 0.0269 | 2.4689 | −0.0827 | 2.6340 | 0.0046 | 0.0300 |
| 4.9627 | 0.1185 | 2.6516 | 0.0168 | 0.0263 | 2.3457 | 0.1073 | 2.6686 | 0.0115 | 0.0302 |
| 0.9015 | 0.9547 | 2.6692 | 0.0163 | 0.0265 | 1.6948 | 0.0577 | 2.6593 | 0.0117 | 0.0303 |
| 2.8402 | 0.2038 | 2.6636 | 0.0211 | 0.0268 | 2.1291 | 0.1984 | 2.6471 | 0.0138 | 0.0289 |
| 1.1254 | −0.7338 | 2.6458 | 0.0200 | 0.0269 | 2.2774 | 0.0914 | 2.6572 | −0.0024 | 0.0288 |
| 1.3064 | −0.6939 | 2.6454 | 0.0168 | 0.0269 | 2.7512 | 1.2060 | 2.6759 | 0.0016 | 0.0279 |
| 1.8746 | −0.0730 | 2.6520 | 0.0175 | 0.0269 | 1.8297 | 3.3518 | 2.6525 | 0.0217 | 0.0290 |
| 2.3129 | 0.1293 | 2.6475 | 0.0139 | 0.0273 | 5.7326 | −0.4421 | 2.6488 | 0.0238 | 0.0280 |
| 6.1266 | −0.1203 | 2.6247 | 0.0163 | 0.0283 | 3.9727 | 0.3677 | 2.6347 | 0.0191 | 0.0297 |
| −0.0478 | 0.3266 | 2.6509 | 0.0221 | 0.0273 | 2.5277 | 0.8634 | 2.6439 | 0.0163 | 0.0301 |
| −0.8435 | 0.1195 | 2.6629 | 0.0188 | 0.0277 | 0.0264 | −0.6821 | 2.6406 | 0.0108 | 0.0310 |
| 1.1221 | −0.0635 | 2.6473 | 0.0159 | 0.0278 | 1.0718 | 1.5789 | 2.6484 | 0.0127 | 0.0298 |
| 1.1601 | −1.3225 | 2.6767 | 0.0035 | 0.0276 | 5.5419 | 0.7405 | 2.6412 | 0.0198 | 0.0295 |
| 1.5515 | 0.4051 | 2.6584 | 0.0124 | 0.0266 | 3.1541 | 0.8144 | 2.6338 | 0.0177 | 0.0287 |
| 5.4314 | 0.5667 | 2.6316 | 0.0144 | 0.0268 | 2.5033 | 0.8817 | 2.6274 | 0.0187 | 0.0294 |
| 6.4706 | 0.7109 | 2.6748 | 0.0160 | 0.0276 | 4.0518 | −0.0335 | 2.6594 | 0.0183 | 0.0284 |
| 5.6930 | 1.3410 | 2.6381 | 0.0182 | 0.0278 | 3.9070 | 0.3701 | 2.6492 | 0.0207 | 0.0279 |
| 4.0447 | −0.3637 | 2.6544 | 0.0117 | 0.0299 | 3.8873 | −0.3868 | 2.6391 | 0.0194 | 0.0276 |
| 2.4545 | −0.0489 | 2.6662 | 0.0071 | 0.0296 | −2.2341 | 1.6680 | 2.6553 | 0.0147 | 0.0262 |
| 1.2373 | 0.6740 | 2.6491 | 0.0172 | 0.0292 | 1.7356 | 0.2896 | 2.6477 | 0.0157 | 0.0273 |
| 2.0195 | −0.5999 | 2.6366 | 0.0181 | 0.0294 | 1.4002 | 0.8415 | 2.6297 | 0.0208 | 0.0282 |

TABLE 2-continued

| | | | | | | | | | |
|---|---|---|---|---|---|---|---|---|---|
| 0.0648 | −0.1082 | 2.6527 | 0.0120 | 0.0286 | 3.6738 | 1.3182 | 2.6398 | 0.0117 | 0.0274 |
| −1.1825 | −0.1007 | 2.6473 | 0.0103 | 0.0275 | 2.9344 | 0.0889 | 2.6308 | 0.0115 | 0.0287 |
| −0.1409 | 0.7261 | 2.6265 | 0.0055 | 0.0282 | 0.5870 | 0.0361 | 2.6712 | 0.0100 | 0.0277 |
| 1.0857 | 0.2146 | 2.6571 | 0.0051 | 0.0266 | 5.1135 | 1.5940 | 2.6726 | 0.0002 | 0.0271 |
| 0.2192 | 0.5772 | 2.6316 | 0.0193 | 0.0284 | 1.3554 | 0.4734 | 2.6490 | 0.0081 | 0.0257 |
| 1.2993 | 1.0382 | 2.6388 | 0.0217 | 0.0275 | 2.0719 | 0.2522 | 2.6608 | 0.0155 | 0.0257 |
| 0.6346 | 1.4641 | 2.6587 | 0.0164 | 0.0272 | 1.9363 | −0.2471 | 2.6596 | 0.0073 | 0.0265 |
| 1.3008 | 1.7269 | 2.6524 | 0.0092 | 0.0262 | 0.0539 | −0.4363 | 2.6492 | 0.0176 | 0.0287 |
| 3.0064 | 1.5901 | 2.6622 | 0.0198 | 0.0273 | 0.5551 | −0.1603 | 2.6342 | 0.0189 | 0.0277 |
| 1.4510 | 1.4926 | 2.6516 | 0.0084 | 0.0278 | 3.5215 | 0.6926 | 2.6343 | 0.0172 | 0.0278 |
| 1.9123 | 0.3994 | 2.6453 | 0.0121 | 0.0283 | 4.0195 | 1.1967 | 2.6624 | 0.0104 | 0.0279 |
| 3.8838 | −0.4143 | 2.6584 | 0.0088 | 0.0286 | 2.2126 | 0.7001 | 2.6676 | 0.0150 | 0.0280 |
| 2.1482 | −0.3200 | 2.6503 | 0.0193 | 0.0294 | 1.4314 | −0.3612 | 2.6465 | 0.0129 | 0.0275 |
| 2.7011 | −0.1556 | 2.6488 | 0.0186 | 0.0288 | 0.2025 | 1.5073 | 2.6473 | 0.0084 | 0.0277 |
| 3.0142 | 1.7930 | 2.6649 | 0.0125 | 0.0269 | 1.5765 | −0.4884 | 2.6270 | 0.0167 | 0.0266 |
| 2.0626 | −0.2325 | 2.6486 | 0.0145 | 0.0266 | 2.6630 | −0.3758 | 2.6378 | 0.0156 | 0.0270 |
| 1.3075 | 0.0367 | 2.6419 | 0.0203 | 0.0275 | 5.1488 | −0.1241 | 2.6533 | 0.0221 | 0.0280 |
| 3.2476 | 0.5700 | 2.6382 | 0.0236 | 0.0277 | 5.6596 | −0.3814 | 2.6444 | 0.0216 | 0.0278 |
| 4.8414 | −0.4105 | 2.6651 | 0.0172 | 0.0284 | 5.4980 | −0.6379 | 2.6626 | 0.0199 | 0.0283 |
| 2.1621 | 0.0915 | 2.6599 | 0.0131 | 0.0282 | 3.0443 | 0.5816 | 2.6492 | 0.0168 | 0.0281 |
| 3.9532 | 0.3748 | 2.6817 | 0.0049 | 0.0277 | 2.6895 | −0.1860 | 2.6437 | 0.0183 | 0.0270 |
| 1.9418 | −0.0814 | 2.6667 | 0.0076 | 0.0281 | 1.7831 | −0.9372 | 2.6652 | 0.0118 | 0.0261 |
| 2.6563 | 0.5933 | 2.6197 | 0.0131 | 0.0274 | 3.8252 | 0.2824 | 2.6552 | 0.0180 | 0.0262 |
| 2.8363 | 0.2643 | 2.6462 | 0.0183 | 0.0268 | 2.9598 | 0.2530 | 2.6620 | 0.0123 | 0.0260 |
| 0.5135 | 0.5905 | 2.6694 | 0.0127 | 0.0277 | 1.8252 | 0.6973 | 2.6502 | 0.0085 | 0.0263 |
| 5.2928 | 0.6642 | 2.6624 | 0.0111 | 0.0272 | 2.4287 | 0.6812 | 2.6900 | 0.0063 | 0.0264 |
| 1.7432 | 0.2334 | 2.6577 | 0.0169 | 0.0273 | 5.0761 | 1.8561 | 2.6568 | 0.0159 | 0.0272 |
| 3.4760 | 0.6209 | 2.6478 | 0.0132 | 0.0282 | 0.4468 | 0.3913 | 2.6383 | 0.0281 | 0.0277 |
| 0.7206 | 0.6170 | 2.6557 | 0.0170 | 0.0272 | 2.9688 | 0.5846 | 2.6603 | 0.0165 | 0.0293 |
| −0.2979 | 0.0385 | 2.6415 | 0.0174 | 0.0275 | 3.9400 | 1.4588 | 2.6787 | 0.0112 | 0.0268 |
| 2.6450 | 0.3160 | 2.6622 | 0.0165 | 0.0276 | 2.4346 | 1.2917 | 2.6565 | 0.0122 | 0.0269 |
| 3.0699 | 0.4915 | 2.6527 | 0.0214 | 0.0270 | 1.5787 | 1.0159 | 2.6455 | 0.0093 | 0.0270 |
| 2.4165 | 0.4811 | 2.6536 | 0.0196 | 0.0291 | −0.5695 | 1.0801 | 2.6330 | 0.0252 | 0.0274 |
| 1.8736 | 1.5841 | 2.6406 | 0.0131 | 0.0288 | −0.3294 | 1.0115 | 2.6532 | 0.0284 | 0.0268 |
| 3.6034 | 2.0621 | 2.6645 | 0.0154 | 0.0278 | 3.3528 | 2.7957 | 2.6434 | 0.0316 | 0.0264 |
| 4.2998 | −0.0787 | 2.6480 | 0.0200 | 0.0276 | −0.0093 | 0.8596 | 2.6430 | 0.0164 | 0.0256 |
| 3.9555 | −0.1884 | 2.6409 | 0.0226 | 0.0292 | 2.0246 | 0.6432 | 2.6418 | 0.0099 | 0.0266 |
| 0.8139 | −0.5540 | 2.6455 | 0.0180 | 0.0284 | 4.5836 | 1.4561 | 2.6522 | 0.0088 | 0.0285 |
| 2.1694 | 0.1378 | 2.6475 | 0.0088 | 0.0272 | 3.2806 | −0.2098 | 2.6533 | 0.0053 | 0.0275 |
| 1.7707 | −0.2607 | 2.6234 | 0.0071 | 0.0279 | 2.7829 | 0.0721 | 2.6382 | 0.0068 | 0.0286 |
| 0.9334 | 0.2441 | 2.6775 | 0.0052 | 0.0298 | 1.6528 | 1.0183 | 2.6706 | 0.0065 | 0.0295 |
| 3.6275 | 0.5285 | 2.6454 | 0.0178 | 0.0289 | 4.1942 | −0.8104 | 2.6520 | 0.0119 | 0.0315 |
| 1.4500 | 0.1172 | 2.6353 | 0.0211 | 0.0277 | 2.0121 | −0.4914 | 2.6409 | −0.0008 | 0.0304 |
| 1.4600 | 0.4299 | 2.6527 | 0.0177 | 0.0269 | 2.4689 | −0.0827 | 2.6340 | 0.0046 | 0.0300 |
| 4.9627 | 0.1185 | 2.6516 | 0.0168 | 0.0263 | 2.3457 | 0.1073 | 2.6686 | 0.0115 | 0.0302 |
| 0.9015 | 0.9547 | 2.6692 | 0.0163 | 0.0265 | 1.6948 | 0.0577 | 2.6593 | 0.0117 | 0.0303 |
| 2.8402 | 0.2038 | 2.6636 | 0.0211 | 0.0268 | 2.1291 | −0.1984 | 2.6471 | 0.0138 | 0.0289 |
| 1.1254 | −0.7338 | 2.6458 | 0.0200 | 0.0269 | 2.2774 | 0.0914 | 2.6572 | −0.0024 | 0.0288 |
| 1.3064 | −0.6939 | 2.6454 | 0.0168 | 0.0269 | 2.7512 | 1.2060 | 2.6759 | 0.0016 | 0.0279 |
| 1.8746 | −0.0730 | 2.6520 | 0.0175 | 0.0269 | 1.6297 | 3.3518 | 2.6525 | 0.0217 | 0.0290 |
| 2.3129 | 0.1293 | 2.6475 | 0.0139 | 0.0273 | 5.7326 | −0.4421 | 2.6488 | 0.0238 | 0.0280 |
| 6.1266 | −0.1203 | 2.6247 | 0.0163 | 0.0283 | 3.9727 | 0.3677 | 2.6347 | 0.0191 | 0.0297 |
| −0.0478 | 0.3266 | 2.6509 | 0.0221 | 0.0273 | 2.5277 | 0.8634 | 2.6439 | 0.0163 | 0.0301 |
| −0.8435 | 0.1195 | 2.6629 | 0.0199 | 0.0277 | 0.0264 | 0.6821 | 2.6406 | 0.0109 | 0.0310 |
| 1.1221 | −0.0635 | 2.6473 | 0.0159 | 0.0278 | 1.0718 | 1.5789 | 2.6484 | 0.0127 | 0.0298 |
| 1.1601 | −1.3225 | 2.6767 | 0.0035 | 0.0276 | 5.5419 | 0.7405 | 2.6412 | 0.0198 | 0.0295 |
| 1.5515 | 0.4051 | 2.6584 | 0.0124 | 0.0266 | 3.1541 | 0.8144 | 2.6338 | 0.0177 | 0.0287 |
| 5.4314 | 0.5687 | 2.6316 | 0.0144 | 0.0268 | 2.5033 | 0.8817 | 2.6274 | 0.0187 | 0.0294 |
| 6.4706 | 0.7109 | 2.6748 | 0.0160 | 0.0276 | 4.0518 | −0.0335 | 2.6594 | 0.0183 | 0.0284 |
| 5.6930 | 1.3410 | 2.6381 | 0.0182 | 0.0278 | 3.9070 | 0.3701 | 2.6492 | 0.0207 | 0.0279 |
| 4.0447 | −0.3637 | 2.6544 | 0.0117 | 0.0299 | 3.8873 | −0.3868 | 2.6391 | 0.0194 | 0.0276 |
| 2.4545 | −0.0489 | 2.6662 | 0.0071 | 0.0296 | −2.2341 | 1.6680 | 2.6553 | 0.0147 | 0.0262 |
| 1.2373 | 0.6740 | 2.6491 | 0.0172 | 0.0292 | 1.7356 | 0.2896 | 2.6477 | 0.0157 | 0.0273 |
| 2.0195 | −0.5999 | 2.6366 | 0.0181 | 0.0294 | 1.4002 | 0.8415 | 2.6297 | 0.0208 | 0.0282 |
| 0.0648 | −0.1082 | 2.6527 | 0.0120 | 0.0286 | 3.6738 | 1.3182 | 2.6398 | 0.0117 | 0.0274 |
| −1.1925 | −0.1007 | 2.6473 | 0.0103 | 0.0275 | 2.9344 | 0.0899 | 2.6308 | 0.0115 | 0.0287 |
| −0.1409 | 0.7261 | 2.6265 | 0.0055 | 0.0282 | 0.5870 | 0.0361 | 2.6712 | 0.0100 | 0.0277 |
| 1.0857 | 0.2146 | 2.6571 | 0.0051 | 0.0266 | 5.1135 | 1.5940 | 2.6726 | 0.0002 | 0.0271 |
| 0.2192 | 0.5772 | 2.6316 | 0.0193 | 0.0284 | 1.3554 | 0.4734 | 2.6490 | 0.0091 | 0.0257 |
| 1.2993 | 1.0382 | 2.6389 | 0.0217 | 0.0275 | 2.0718 | 0.2522 | 2.6608 | 0.0155 | 0.0257 |
| 0.6346 | 1.4641 | 2.6587 | 0.0164 | 0.0272 | 1.9363 | −0.2471 | 2.6596 | 0.0073 | 0.0265 |
| 1.3008 | 1.7269 | 2.6524 | 0.0092 | 0.0262 | 0.0539 | −0.4363 | 2.6492 | 0.0176 | 0.0287 |
| 3.0064 | 1.5901 | 2.6622 | 0.0198 | 0.0273 | 0.5551 | −0.1603 | 2.6342 | 0.0189 | 0.0277 |
| 1.4510 | 1.4926 | 2.6516 | 0.0084 | 0.0278 | 3.5215 | 0.6926 | 2.6343 | 0.0172 | 0.0278 |
| | | | | | 3.9613 | −0.1382 | 2.6665 | 0.0137 | 0.0283 |
| | | | | | 3.7216 | 0.3433 | 2.6561 | 0.0097 | 0.0271 |
| | | | | | 0.3863 | 0.7137 | 2.6480 | 0.0106 | 0.0270 |
| | | | | | 1.7291 | 1.5199 | 2.6464 | 0.0089 | 0.0276 |
| | | | | | 5.8988 | 1.5338 | 2.6524 | 0.0108 | 0.0286 |

TABLE 2-continued

| | | | | |
|---|---|---|---|---|
| −0.0662 | 0.3417 | 2.6596 | 0.0214 | 0.0293 |
| 3.2610 | −0.9585 | 2.6446 | 0.0203 | 0.0290 |
| 0.9132 | 1.0255 | 2.6486 | 0.0242 | 0.0284 |

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. Memory storing a program for execution on a data processing system comprising:

means for receiving signals representative of levels of a marker for disease from an individual;

means for computing a risk of disease from one or more levels of a marker;

means for comparing the computed risk to thresholds to triage the individual into one of normal, borderline and elevated risk groups; and means for storing the marker levels for subsequent computations of risk of disease.

2. Memory as claimed in claim 1 further comprising means for outputting a test interval value which is inversely related to the computed risk, to identify the interval at which an individual should again be test to determine the level of the marker to disease.

3. Memory as claimed in claim 2 wherein the risk of disease is again computed using a marker level obtained at the test interval.

4. Memory as claimed in claim 1 further comprising means for creating a bar graph display indicating the computed risk, the display being green when the risk is less than the normal threshold, the display being yellow when the risk is between the borderline thresholds, and the display being red when the risk is greater than the elevated threshold.

5. Memory as claimed in claim 1 wherein risk of disease is computed form a statistical analysis of marker level distributions for tested normal and diseased populations.

6. Memory as claimed in claim 5 wherein risk of disease is computed from multivariate distributions.

7. Memory as claimed in claim 6 wherein the marker level changes exponentially over time for diseased individuals and the multivariate distributions are determined from the slope and intercept of the log of detected marker levels over time for individuals within normal and diseased populations.

8. Memory as claimed in claim 7 wherein random draws are used to compute average densities from the normal and disease populations given the marker level for the individual.

9. Memory as claimed in claim 8 wherein risk of disease is computed as a product of an odds factor and an estimate of prior odds, wherein the odds factor is the ratio of the average density from the disease population to the average density from the normal population.

10. Memory as claimed in claim 8 wherein a time correlation component is included in a linear regression model of marker levels to compute risk of disease.

11. A computer comprising:

an input device for receiving marker levels;

a display for displaying risk of disease and courses of action, based upon the risk of disease; and memory comprising means for receiving signals representative of levels of a marker for disease; means for computing risk of disease from one or more levels of the marker; means for comparing the computed risk to thresholds to triage the individual into one of normal, borderline and elevated risk groups; and means for storing the marker levels for subsequent computations of risk of disease.

12. A computer system as claimed in claim 11, wherein the display is a bar graph display indicating the computed risk, the bar graph display being green when the risk is less than the normal threshold, the bar graph display being yellow when the risk is between the borderline thresholds, and the bar graph display being red when the risk is greater than the elevated threshold.

13. A computer system as claimed in claim 11 wherein the risk of disease is again computed using a marker level obtained at the test interval.

14. A computer system as claimed in claim 11 wherein risk of disease is computed from a statistical analysis of marker level distributions for tested normal and diseased populations.

15. A computer system as claimed in claim 14 wherein risk of disease is computed from multivariate distributions.

16. A computer system as claimed in claim 15 wherein the marker level changes exponentially over time for diseased individuals and the multivariate distributions are determined from the slope and intercept of the log of detected marker levels over time for individuals within normal and diseased populations.

17. A computer system as claimed in claim 16 wherein random draws are used to compute average densities from the normal and disease populations given the marker level for the individual.

18. A computer system as claimed in claim 17 wherein risk of disease is computed as a product of an odds factor and an estimate of prior odds, wherein the odds factor is the ratio of the average density from the disease population to the average density from the normal population.

19. A computer system as claimed in claim 17 wherein a time correlation component is included in a linear regression model of marker levels to compute risk of disease.

* * * * *